(12) United States Patent
Gershoni et al.

(10) Patent No.: US 11,311,460 B1
(45) Date of Patent: Apr. 26, 2022

(54) METHOD AND APPARATUS OF SECURE STORAGE FOR DISPENSING OF OPIOIDS (SSDO)

(71) Applicant: Telemedicine Health, Inc., Weston, FL (US)

(72) Inventors: Daniel Gershoni, Weston, FL (US); Farhad David Nosrati, Encino, CA (US)

(*) Notice: Subject to any disclaimer, the term of this patent is extended or adjusted under 35 U.S.C. 154(b) by 185 days.

(21) Appl. No.: 16/530,022

(22) Filed: Aug. 2, 2019

Related U.S. Application Data

(60) Provisional application No. 62/715,930, filed on Aug. 8, 2018.

(51) Int. Cl.
| | |
|---|---|
| *A61J 7/04* | (2006.01) |
| *A61J 7/00* | (2006.01) |
| *A61J 1/03* | (2006.01) |
| *G16H 20/13* | (2018.01) |

(52) U.S. Cl.
CPC .......... *A61J 7/0481* (2013.01); *A61J 1/035* (2013.01); *A61J 7/0076* (2013.01); *A61J 7/0418* (2015.05); *A61J 7/0436* (2015.05); *G16H 20/13* (2018.01); *A61J 2200/30* (2013.01); *A61J 2200/70* (2013.01); *A61J 2205/50* (2013.01); *A61J 2205/60* (2013.01); *A61J 2205/70* (2013.01)

(58) Field of Classification Search
CPC ...... A61J 7/0481; A61J 7/0418; A61J 7/0436; A61J 7/0076; A61J 1/035; A61J 2205/60; A61J 2205/70; A61J 2205/50; A61J 2200/30; A61J 2200/70; G16H 20/13
See application file for complete search history.

(56) References Cited

U.S. PATENT DOCUMENTS

| | | | | |
|---|---|---|---|---|
| 4,953,745 | A * | 9/1990 | Rowlett, Jr. | G06Q 20/342 221/5 |
| 5,507,277 | A | 4/1996 | Rubsamen et al. | |
| 5,522,525 | A * | 6/1996 | McLaughlin | A61J 7/0481 221/4 |
| 6,439,422 | B1 | 8/2002 | Papp et al. | |
| 6,848,593 | B2 | 2/2005 | Papp | |
| 7,080,755 | B2 * | 7/2006 | Handfield | A61J 7/0076 221/13 |

(Continued)

FOREIGN PATENT DOCUMENTS

| | | |
|---|---|---|
| WO | WO2002011778 A1 | 2/2002 |
| WO | WO2002094234 A1 | 11/2002 |

*Primary Examiner* — Michael Collins
(74) *Attorney, Agent, or Firm* — Allen D. Hertz, P.A.; Allen D. Hertz

(57) ABSTRACT

A method and apparatus for Secure Storage and Dispensing of Opioid (SSDO) or other controlled substances while providing remote assistance and monitoring. In one embodiment, the apparatus comprises a motorized medication tray for automatic dispensing of pills with optional blister pack containing sealed medication. The device further comprises of a secure tamper resistant housing mechanism, plurality of sensors along with a wireless communication module to notify the remote operators in case of illegal and unauthorized access. The current invention can be configured into multiple embodiments including but not limited to a mobile wearable device capable of attaching to a person's wrist, arm, foot and other body parts.

28 Claims, 43 Drawing Sheets

(56) References Cited

U.S. PATENT DOCUMENTS

| | | | |
|---|---|---|---|
| 7,735,680 B2* | 6/2010 | Godlewski | G07F 11/54 221/122 |
| 7,844,362 B2* | 11/2010 | Handfield | G07F 11/44 700/237 |
| 7,952,315 B2* | 5/2011 | Park, IV | G07F 11/54 318/578 |
| 8,060,249 B2 | 11/2011 | Bear et al. | |
| 8,548,623 B2 | 10/2013 | Poutiatine et al. | |
| 9,361,431 B2 | 6/2016 | Fauci | |
| 9,953,140 B2 | 4/2018 | McLean et al. | |
| 10,181,013 B2 | 1/2019 | Alleckson et al. | |
| 10,182,970 B1 | 1/2019 | Hassani et al. | |
| 10,296,719 B2* | 5/2019 | Ekin | G07F 17/0092 |
| 2003/0052787 A1* | 3/2003 | Zerhusen | A61G 7/0513 340/573.1 |
| 2006/0058724 A1* | 3/2006 | Handfield | A61J 7/0076 604/20 |
| 2006/0157491 A1 | 7/2006 | Whittle et al. | |
| 2007/0260491 A1 | 11/2007 | Palmer et al. | |
| 2008/0283542 A1* | 11/2008 | Lanka | G07F 17/0092 221/6 |
| 2010/0305749 A1* | 12/2010 | Coe | G07F 11/62 700/231 |
| 2013/0284755 A1* | 10/2013 | Yuyama | B65D 83/04 221/13 |
| 2017/0231870 A1* | 8/2017 | Stachler | A61J 7/0084 222/28 |
| 2018/0028408 A1 | 2/2018 | Li et al. | |
| 2018/0110939 A1 | 4/2018 | Lanzkowsky | |

\* cited by examiner

METHOD AND APPARATUS OF SECURE STORAGE FOR DISPENSING OF OPIOIDS (SSDO)

CROSS-REFERENCE TO RELATED APPLICATIONS

This application takes priority from provisional application Ser. No. 62/715,930, filed on Aug. 8, 2018, which is incorporated herein in its entirety.

BACKGROUND OF INVENTION

Field of the Invention

The invention is related to a device and its methods of use for a remote monitored, software assisted automated device used for delivering and monitoring the Opioids and/or other drugs. The device provides a storage and dispensing mechanism which is tamper resistant in order to protect against illegal access to the Opioids contents. Plurality of motorized medication trays are being utilized in a synchronized motion in order to deliver Opioids and supplement medicine from a manually loaded medication tray as well as a sealed blister pack containing the Opioids and other drugs.

Description of Prior Art

Each year, roughly 30,000 people die from Opioid overdose. In 2014, there were more Opioid overdose deaths compared to any other year. Until recently, the administration of this medication was reserved for use by only highly and qualified professionals such as doctors, nurses and other emergency personnel. However, in the last decade, there has been a significant push to having nonmedical individuals administer it to Opioid users in need and with good results.

Presently, there are various delivery methods available to patients to aid in decreasing the risk of Opioid overdose. The medication is administered by the conventional route which includes oral, intravenous, sublingual, etc. while audio instructions are provided on appropriate technique.

For instance, International Patent Application WO 2002011778 A1 to Wermeling describes an invention which relates to pharmaceutical drug compositions and preparations that are narcotic antagonists and analgesics, specifically Opioids. This invention also relates to pharmaceutical drug delivery devices, specifically to devices for the intranasal administration of drugs classified as controlled substances. Further, US Pre-Grant Publication 2018/0110939 A1 to Lanzkowsky also describes a method, system and apparatus for administering various medicaments including those for treating pain and substance dependency. The apparatus is a unit for heat activation of a morphine opiate liquid concentrate mixed with a carrier substance to produce inhaled gas. The method includes inhaling the heat activated gaseous vapor concentrate for pain relief, to treat substance dependency or administration of other medicaments.

Furthermore, International Patent Application WO 2002094234 A1 to Rabinowitz also describes an invention which relates to the delivery of Opioids through an inhalation route. Specifically, it relates to aerosols containing Opioids that are used in inhalation therapy. Moreover, US Pre-Grant Publication 2006/0157491 A1 to Whittle also describes an invention which relates to novel formulations, dosage forms and modes of delivery for treating patients addicted to a group of drugs which can result in dependencies and misuse.

Meanwhile, monitoring and control of the storage and dispensing device for Opioids and other drugs were also presented in various inventions.

For instance, U.S. Pat. No. 10,182,970 B1 to Hassani describes a secured and programmable medical dispenser which is configured to distribute medicine according to a schedule. The secured and programmable medical dispenser has a dispenser body mechanically coupled to a dispenser lid with a locking solenoid. A pill tube is arranged within the dispenser body and further has an open pill tube proximal end and a pill tube distal end. A microcontroller is attached to the dispenser lid, communicatively coupled to the pill release rotary solenoid and the liquid release rotary solenoid.

Another invention, described in U.S. Pat. No. 10,296,719 B2 to Ekin also describes an invention related to a smart pill dispenser which is used in a household, on a desktop, by keeping the different types of medication along with different dosages inside the container, which provides information to the user in order for the user to take his/her medication in time and in correct doses and which can inform the user interactively thru the use of smart devices such as cell phones, and smart watches.

U.S. Pat. No. 10,181,013 B2 to Portney also describes a pill dispensing system which includes an electronic mobile communication device with a wireless transmitter and receiver. A pill cartridge has a cartridge body storing a plurality of pills, where the cartridge body includes an electronic tag storing data. A pill cartridge dispenser is configured to receive at least one of the pill cartridges and configured to electromechanically control dispensing of the plurality of pills from the cartridge body, where the pill cartridge dispenser is configured to be in wireless communication with the electronic mobile communication device.

US Pre-Grant Publication 2018/0028408 A1 to Li describes in one embodiment, a medication dispensing device of a system for controlling and monitoring medicine dispensation includes means for securely containing a medication to be dispensed to a specific patient, confirm the identity of the patient, and to determine whether or not the patient is eligible to receive a dose of the medication at the time the dose is requested, only if the patient's identity is confirmed and the patient is eligible to receive the dose.

Further, U.S. Pat. No. 8,060,249 B2 to Bear also describes devices, systems, and methods for remote visualization of the storage compartments in a medication dispenser device, to monitor a patient's compliance with a medication dosage schedule and for verifying the proper loading of medication into the patient's medication dispenser device. The device may include a plurality of storage compartments, each having an interior space for storing at least one medication or medication reminder marker; an image capturing device (e.g., a camera) which can be positioned to capture an image of the interior space of each storage compartment; and a communications module for electronically transmitting the captured image to a central monitoring station.

Furthermore, U.S. Pat. No. 5,507,277 A to Rubsamen also describes a method of controlling access to a drug in an aerosol drug delivery device by an electronic lock and key means is disclosed. Access is limited to the intended user by providing the intended user with a uniquely coded, machine readable key means that matches the unique code of the lock means. Contacting matching lock and key means signals a controlling means to allow use of the device.

Additionally, US Pre-Grant Publication 2007/0260491 A1 to Palmer also describes a system for delivery and monitoring the administration of controlled substances which includes one or more databases including a national database of controlled substance users, a database including physician/pharmacy information, a controlled substance delivery device and a docking station for use together with a network and software for communication between the various components of the system.

In other important aspect in this field of invention, there are also patents which presented secure storage and dispensing drug device.

An example is U.S. Pat. No. 9,361,431 B2 to Fauci describes embodiments of the invention to provide safe, secure and accurate point-to-point delivery of prescription and non-prescription drugs in the long-term home care or ambulatory care environment. More specifically, embodiments of the present invention provide for a low-cost, easy-to-use system comprised of a secure drug dispensing unit and medication enclosure combined with wireless connectivity and software based on smart mobile phone technology. Such systems and methods, referred to herein as a Secure, Control, and Enhance Medication Adherence (SCEMA) system, can mitigate the aforementioned risks associated with the use of prescription and non-prescription drugs.

Another patent, U.S. Pat. No. 9,953,140 B2 to McLean, also describes a system, method, and apparatus for securely dispensing one or more prescribed substances at a given time and/or date. In certain embodiments, a pill dispensing device may include a generally tamper-proof portable housing. A replaceable cartridge may be configured to be disposed within the portable housing. The replaceable cartridge also may be generally tamper-proof. The portable housing and/or the replaceable cartridge may be operable to dispense a predefined amount of a prescribed substance at a given time and/or date.

Another example is disclosed in US Pre-Grant Publication 2017/0231870 A1 to Stachler, which discloses a medication storage and dispensing device having a biometric sensor to restrict access to the medication stored within. The device is locked to prevent access and includes tamper resistance features to prevent unauthorized access to the medication stored within. The device has wireless connection features that allow monitoring by medical professionals.

Also, U.S. Pat. No. 8,548,623 B2 to Poutiatine describes a dispensing devices and systems for oral transmucosal administration of small volume drug dosage forms to the oral mucosa. The dispensing device may be a single dose applicator (SDA), or an electromechanical device comprising a means for patient identification such as a wrist worn RFID tag and annular bidirectional antenna together with a lock-out feature.

Treatments of Opioids drugs are effective and needed continuous monitoring of the patient and their dosing time. Upon review of available patents presented earlier, there is no device providing continuous/intermittent administering, storage as well as monitoring of the patient. Further, the traditional method needs the presence of a conscious and caring bystander and physician. Continuous or near-continuous monitoring is necessary as it would allow the incidence of overdose or for remembering the dosing time, thereby increasing the odds of successful intervention. Unfortunately, these important features were not presented in currently available patents.

To solve the complex problem of prescription Opioid and heroin abuse in this country, one can recognize a need to control the prescribed Opioids from the moment of dispensing by the pharmacy to monitoring the use by the patient in real-time, to the reclamation and proper disposal of the unused pills by the dispensing pharmacy. It will also be advantageous to manage the safety of the Opioids while in the position of the users in such a way that unauthorized use, theft and inability to account for the prescribed Opioid will always be eliminated. It would be beneficial to provide a device and a method of use that impacts the Opioid problem that could be measured clinically, socially and environmentally in a way never done before.

It would also be beneficial to provide a device and a method of using the device which will be specially designed for people who are regularly on prescribed narcotics. It would be preferred that the device include a tamper-resistant casing with advanced software and video reporting technology, whereby the device will proactively monitor, record, and report narcotic usage. Further, it would be beneficial to provide a device that is wearable with an easy module, software assisted, automated with monitoring with audio and video facility for assistance by caregiver and physician.

SUMMARY OF THE INVENTION

It is one object of the present invention to provide a remote monitored, software assisted narcotic dispensing device and methods of use for delivering and monitoring the Opioids and/or other drugs. Throughout the specification, the term Opioids is synonymous with the term Narcotics.

The narcotic dispensing device further includes a tamper resistant medication storage and dispensing mechanism to protect against illegal access to the Opioids contents.

The narcotic dispensing device additionally includes dual motorized medication trays that are synchronized in order to simultaneously deliver Opioids and other drugs including supplement medicine from the plurality of medication trays.

In one configuration of the narcotic dispensing device, Opioids and other drugs as well as supplemental medicine can be loaded into both medication trays manually and dispensed simultaneously.

In yet another configuration of the narcotic dispensing device, Opioids and other drugs and supplemental medicine can be loaded into both medication trays manually and dispensed with a time-offset from each other.

In yet another configuration of narcotic dispensing device, a sealed blister pack can be pre-loaded with Opioids and placed into one of the motorized trays, while other drugs and supplement medicine can be manually loaded into the second motorized medication tray. The two motorized medication trays can then be programmed to dispense medicine simultaneously or at a time-offset from each other.

Another feature of the narcotic dispensing device includes one or more sensors placed at a push out passage opening that can detect when an object such as human hand is placed under an exit compartment. When the object is placed under the exit compartment, the at least one sensor would trigger a motorized mechanism to rotate one or both of the motorized medication trays containing the Opioids and other drugs to position the next dosage of pills at the passage opening to be dispensed.

The narcotic dispensing device may further include at least one biometric sensor to detect and authenticate a presence of an authorized user before allowing for the medications to be dispensed. The at least one biometric sensor provided may include, but is not limited to, a fingerprint scanner, a retina scanner, a facial recognition system, and a voice recognition system.

The narcotic dispensing device may further include a wireless Near Field Communication (NFC) circuit to detect and authenticate a presence of the authorized user before allowing dispensing of the medications.

The narcotic dispensing device may further include a display unit that provides information related to the medications to be taken, including but not limited to: reminder messages, instructions on the medications and how to take them, as well as actual images of the medications related to each dose of medication.

The locking mechanism of the narcotic dispensing device may be additionally equipped with series of electronic sensors that detect tampering with the device. In case tampering occurs, the narcotic dispensing device will enter into a special, restricted alert mode and notify the user via audible alarms as well as notifying the remote operators and caregivers utilizing the built-in Wireless module.

The narcotic dispensing device may further include a camera, a microphone and speaker set to allow live audio and video communication with caregivers, physicians, and remote call-center operators, as well as for audio and video communication to operate the dispenser of the present invention.

The narcotic dispensing device further provides a unique and novel approach for monitoring and dispensing methods including a multi-layer authentication and validation of the authorized user prior to dispensing the Opioids.

The narcotic dispensing device additionally provides a novel punching mechanism that utilizes a dual punching process consisting of a linear motion followed by a rotational movement of an armature shaft to puncture the sealed blister pack and release the containing medicine.

The narcotic dispensing device may further include a weight scale for measuring and validating the amount of Opioids present in each compartment of the two medication trays.

In yet another configuration, the narcotic dispensing device can be made waterproof.

The narcotic dispensing device may further include a separate portable dispensing unit including but not limited to a wristband as well as an ankle bracelet to be used to dispense Opioids and other drugs when away from main dispensing device.

The portable dispensing unit of the present invention may further include one or more compartments for securely storing and dispensing Opioids.

Each of the portable dispenser device compartments can be remotely monitored and programmed to unlock and release medicine.

In one configuration, the portable dispensing unit can take the form of a wristband.

In one configuration, the portable dispensing unit can take the form of a bracelet.

In yet another configuration, the portable dispensing unit can take the form of an ankle bracelet.

The narcotic dispensing device may further include a docking compartment for the portable dispensing unit to mate with it and securely transfer one or more Opioid dosages from the main dispensing unit to the portable unit. The main, secure narcotic dispensing device, utilizes a series of wireless and wired sensors to authenticate the portable dispense unit mating with it and securely release Opioids and other drugs form one or both of the dispense trays into the portable dispense unit compartments.

The narcotic dispensing device addresses the problems in the art and advances the state of the relevant technology with a variety of new features and capabilities that innovate over and significantly enhance prior devices in new and novel ways. In one of the many preferable configurations, the present invention contemplates medication compliance, monitoring, and protection of device with illegal or unauthorized use that includes, among other features and elements a blister pack formed with unit dose compartments in device, which can be formed like the blister packs well-known to those skilled in the relevant arts. Several aspects of the present invention described herein reference Opioid drugs; however the present invention may also be used for drugs other than Opioid drugs and should not be limited to only Opioid drugs.

In the main aspect, a device is provided for administering, storing and monitoring of Opioid and other drugs includes a processor, a memory, a wireless transceiver, an interface display, a microphone, a speaker, multiple sensor mechanism, a motorized mechanism, a dispensing mechanism, a monitoring protocol, an accommodation for a blister-pack, a punching armature.

In one configuration, the device will further comprise a mobile device such as a smart phone or tablet computer to provide interactive assistance to the user while wirelessly notifying the remote operators of the status of the device and Opioid dispenses.

In the main aspect, the present invention relates to a self-programmable wireless device for administering, storage and monitoring system, including but not limited to a form of a bracelet for Opioid and other drugs. More specifically, the present invention relates to secure storage and dispensing of Opioids and other medications with a built-in intelligence and its capabilities to meet an individual patient's needs and monitoring.

In main aspect, a method for dispensing an Opioid or another drug comprises:
 a. In one configuration, the device is a stand-alone unit.
 b. In yet another configuration, the device is placed on the wrist, ankle or other parts of a human body.
 c. In yet another configuration the device includes a compartment for blister packs for Opioids and other drugs and capable of dispensing a plurality of pills from a pre-sealed container such as a blister pack to a collector at pre-programmed dispense time, a capability to record a date and time of each dispensed dosage and provide a system for tracking medication compliance.

In the main aspect, the device dispenses the Opioid and other drugs from a motorized tray contain manually inserted medication.

In yet another aspect, the device dispenses the Opioid and other drugs from a sealed container such as a Blister-Pack unit placed in the secondary motorized medication tray.

In yet another aspect, the device dispenses the Opioid and other drugs from both manual tray and a sealed blister-pack container simultaneously.

In yet another aspect, the device dispenses the Opioid and other drugs from both manual tray and a sealed blister-pack container with a pre-programmed time delay between the two medication dispensing. This novel concept allows users to have multiple medications at one or more intervals during each day.

In one aspect motorized mechanism is used for rotatable positioning of the blister pack stepwise relative to the part of the device including the push-out means. The optical sensor detects the presence of an object such as a person's hand at the passage opening and allows the Opioid and other drugs pills to be dispensed automatically.

In another aspect, the present device has an alarm with the ability to alert the prescriber, medical care providers, caregivers or other persons, to whom notification is desired of unauthorized access, dispensing of drugs, or security breach, Opioids (narcotics) or other drugs.

In another aspect, the device may further include a camera, a microphone, and a speaker set to allow live audio and video communication with caregivers, physicians and remote call-center operators, and for audio and video communication to operate the dispenser of the present invention.

In one aspect, the device comprises of a tamper proof casing with plurality of sensors as well as wireless communication module to notify if the device has unauthorized access or has been forced open. The communication module includes but are not limited to Wi-Fi, Cellular (3G, 4G, etc), and Bluetooth.

In one aspect, the tamper proof casing comprised of dual motorized locking mechanisms to ensure secure access to the plurality of medication tray access covers. A centralized locking mechanism is utilized to anchor the top housing cover for the inner medication tray containing the manually loaded medication, while a plurality of sliding shafts placed in the inner medication tray's access cover extend out into the matching openings in the outer medication tray access cover to securely lock the two rotary medication tray covers together.

In another aspect, the device has the capability for transmitting an alarm signal in case of unauthorized access, illegal dispensing of drugs, or security breach of the device to communicate, including but not limited to audio and or visual communication with a monitoring center, the user, caregiver, physician, and/or others via cellular communication.

In another aspect, the device communicates data, utilizing communication modules, including but not limited to Wi-Fi, Cellular (3G, 4G, and 5G), Bluetooth, wired communication, and other available means.

In another aspect, the present invention uses a biometric system for verifying the prescribed user, caregiver, physician, and other authorized users. The biometrics sensors used in the device including but are not limited to a fingerprint scanner, a retina scanner, and the like, for secure access to the device.

In another aspect, the device includes a Global Positioning System (GPS) locating capability allowing the location of the device to be sent out to remote monitoring centers as well as to the Emergency Medical Technician (EMT) service in case of emergency. In other embodiment, the device is also enabled with "Location Lock" e.g., a feature which identifies weather the device in a designated location has been moved and "Track Me" e.g., a feature which enables an interested party or person to locate the device and to notify if the device has been moved illegally without authorization.

In another aspect, the device also has built-in motion detection feature to notify caregiver and user if the device is moved, fallen, and damaged due to sudden movement or drops. The motion detection feature is utilized through use an accelerometer as well as other means.

In another aspect, the device has connectivity to a social networking support group for assistance, information access, and notification.

In another aspect, the device includes a display, a microphone, a speaker, and a camera for verification and remote care by a medical care provider, prior to administration of a urine test for taking the Opioid pills or other drugs. Remote caregivers or physician can interactively engage the user utilizing the display, microphone, speaker, and camera to ensure proper steps are taken prior to dispensing the Opioids or other drugs and to conduct proper diagnostics testing such as urine, electrocardiogram (ECG), blood pressure, etc.

In another aspect, the device is also utilized for real-time communication to provide assistance with caregiver, supervisor, and as well as rehabilitation personnel, mental health personnel, family support providers, and others.

In another aspect, the device may further include a built-in thermometer with user contact points for measuring body temperature. The display unit provides the temperature reading locally while the communication module transmits that information to remote operators, caregivers, physicians and family members. The means of communications includes but is not limited to Wi-Fi, Cellular (3G, 4G, and 5G), Bluetooth, wired communication, and other available means.

In another aspect, the device may further include a built-in electrocardiogram (ECG) sensor with user contact points for measuring the user's pulse and or other cardiovascular activities. The storage unit provides local storage for recorded electrocardiogram (ECG) waveforms. The electrocardiogram (ECG) recordings are shown on the display unit, while the communication module transmits that information to remote operators, caregivers, or others. The means of communications include but are not limited to Wi-Fi, Cellular (3G, 4G and 5G), Bluetooth, wired communication, and other available means.

In another aspect, the present invention may further include the feature of a code scanner, including but not limited to barcodes, for scanning medication labels to assist with the verification and adherence process. The code scanning process can also be achieved by connecting the device to an external code scanner via one of the available communication means, including but not limited to a Universal Serial Bus (USB) circuit, Bluetooth, or Wi-Fi.

In another aspect, the present invention utilizes a scale to monitor Opioids being dispensed. This may also be used to assure the return of all unused Opioids to the prescribing pharmacy for proper dispensing. This will further help against unused Opioids finding their way to the illegal Opioid market.

In another aspect, the device includes a unique "Check-On-Me" feature, that comprises a button that when pressed, will communicate wirelessly with outside computers, mobile devices and remote caregivers and operators by sending various electronic signals and messages to alert them of status of the user.

In another aspect, the present invention may include and employ a cabinet/docking station made up of tamper resistant materials including but not limited to heavy duty plastics and/or metal, a communication module, a battery backup alarm, a biometric sensors, a cabinet alarm, and a cabinet utilization logs. For improved connectivity the present invention may also include a cellular booster antenna. This embodiment is particularly useful for the identification, dispensing and storage of Opioid and other drugs in a rehabilitation centers, or other medical facilities with more than one patient. Further, the camera is useful for visual verification of the caregiver or other person assisting in the dispensing of the Opioids or other drugs, and for monitoring the user's ingestion of the Opioids and or other drugs.

In another aspect, the present invention includes a capability for validation and authentication of user ingesting Opioids and/or other drugs by utilizing an infrared camera as well as other comparable means, including but not limited to biometric sensors.

In another aspect, the present invention includes a capability for validating and monitoring whether Opioids and or other drugs were ingested by an authenticated user. This may be performed through the use of an infrared camera and wireless sensors placed on an edible housing for the "Opioid and/or other drugs".

In another aspect, the removable dispensing tray is automated to drop the Opioids and/or other drugs into the removable dispensing tray after biometric verification of the intended authorized users. The removable dispensing tray may further include a biometric sensor to release the Opioids and/or other drugs to the users.

In another aspect, one or more secure Opioid dispensers are stored in a storage cart with trays, shelves, and other storage compartments to house each Opioid dispenser. The trays, shelves, and/or other storage compartments of the Opioid dispensers may be identified by barcode scanning, RFID, Bluetooth, Wi-Fi, Wireless cellular technology, wired connection, such as USB connection, or other means.

In another aspect, one or more secure Opioid dispensers are stored in a storage docking station with one or more docking platforms for Opioids dispenser placement. The Opioids dispensers placed in the docking station may be identified by barcode scanning, RFID, Bluetooth, Wi-Fi, Wireless cellular technology, wired connection, such as USB connection, or other means.

In another aspect, the present invention includes a weight scale, wherein the weight scale is utilized for monitoring Opioids dispensing from the blister pack by constantly or periodically monitoring the weight of the blister pack and/or its contents placed inside the dispenser.

In another aspect, the present invention includes Optical Sensors, wherein the optical sensors are used for detecting the presence of Opioids in the blister pack. The Opioid dispenser will utilize sensors including but not limited to optical sensors and photo sensors to detect a presence of Opioids in each compartment of the blister pack. The blister pack is made up of transparent to partially transparent material with a reflective material used as a seal, wherein the reflective material may be, but is not limited to, aluminum foil. Sensors will be placed under one or more sealed storage compartments of the blister pack as placed in the Opioid dispenser. Once the Opioids are removed from one or more compartments of the Blister Pack, The sensors will detect and report that to an intended recipient, such as remote operators, caregivers, or others.

In another aspect, the present invention utilizes optical sensors to detect the presence of Opioids from a revolving medication storage tray inside the Opioid dispenser. The Opioids dispenser will utilize sensors including but not limited to optical sensors and photo sensors to detect the presence of Opioids in each compartment of the storage medication tray. Once the Opioids are removed from one or more compartment of the storage tray, the sensors will detect and report that to an intended recipient, such as a remote operator, a caregiver, or another intended party.

The following further describes the novel features of the invention:

The present invention, a Secure Storage and Dispensing of Opioids (SSDO) apparatus, provides for secure storage and dispensing of Opioids and other medications. The Secure Storage and Dispensing of Opioids (SSDO) apparatus also utilizes an access cover, which is tamper resistant, and uses one or more sensors to notify if the device has unauthorized access or has been forced open. The device is capable of verifying that medication is taken by the prescribed user via utilizing biometrics, including but not limited to, a retina scan process, a facial recognition process, and/or a fingerprint scanning process of the authenticate user.

Moreover, when a urine test is required prior to taking the Opioid, the Secure Storage and Dispensing of Opioids (SSDO) apparatus can provide verification by a care provider prior to the user's ability to ingest the Opioid. Remote caregivers can also interactively engage with the user utilizing the display, the microphone, the speaker, and/or the camera to ensure proper steps are taken prior to dispensing the Opioids. Also, the Secure Storage and Dispensing of Opioids (SSDO) apparatus can further provide verification that the Opioids are securely stored and are only accessible to the user via multiple authentication means including providing video images as well as various biometric methods, including but not limited to facial recognition, a fingerprint scan and/or a retina scan.

Also, the Secure Storage and Dispensing of Opioids (SSDO) apparatus can further provide information on the location of the medication in relation to the prescribed user for further security and validation of use by the prescribed user. The Secure Storage and Dispensing of Opioids (SSDO) apparatus can further provide ability for local and remote operators to be alerted, when unauthorized dispensing is attempted. The Secure Storage and Dispensing of Opioids (SSDO) apparatus has wireless communication modules including not limited to Wi-Fi, Cellular (3G, 4G, 5G), Bluetooth, and other available means, to alert remote operators, caregivers, law enforcements, and other intended recipients.

Furthermore, the Secure Storage and Dispensing of Opioids (SSDO) apparatus additionally includes an alarm system notifying of an attempt to extract the Opioids and or other drugs forcefully from the secure dispensing device. Various sensors are used to indicate any tampering with the device. It also provides the ability to alert the care providers or other intended parties of a security breach.

Meanwhile, the Secure Storage and Dispensing of Opioids (SSDO) apparatus further provides an ability to notify law enforcement of an attempt to steal Opioids and/or other drugs from the device. The Secure Storage and Dispensing of Opioids (SSDO) apparatus further provides the ability to provide care providers, law enforcement, an/or other persons a GPS location of the prescribed user and the dispensing device, so that an assumption can be made as to who is attempting to extract the Opioids and/or other drugs without authorization.

The Secure Storage and Dispensing of Opioids (SSDO) apparatus further provides an ability to transmit an alarm signal using various wireless communication methods. The means of communications includes but not limited to Wi-Fi, Cellular (3G, 4G and 5G), Bluetooth, wired communication, and other available means. Also, it provides the ability to sound an alarm on the device and/or remotely. The Secure Storage and Dispensing of Opioids (SSDO) apparatus further provides the ability to communicate with the user via cellular communication. The Secure Storage and Dispensing of Opioids (SSDO) apparatus can also communicate with the user via video.

Additionally, the Secure Storage and Dispensing of Opioids (SSDO) apparatus also provides the ability to use visual camera to verify that the user has taken the dispensed Opioids and or other drugs. The Secure Storage and Dispensing of Opioids (SSDO) apparatus also provides an ability to verify the return of all unused Opioids and/or other drugs to the prescribing pharmacy for proper dispensing (eliminating those unused Opioids from finding their way to the illegal Opioid market). Also, the Secure Storage and Dispensing of Opioids (SSDO) apparatus provides for secure access to the dispensing device by an authorized pharmacy only.

The Secure Storage and Dispensing of Opioids (SSDO) apparatus also provides support for sealed blister pack storage, dispensing, and reclamation. It also provides support for remote release of the Opioids and/or other drugs by an approved party or person, including but not limited to a healthcare provider. The Secure Storage and Dispensing of Opioids (SSDO) apparatus further provides support for real-time supervision utilizing cameras, two-way audio, and wireless technology. The Secure Storage and Dispensing of Opioids (SSDO) apparatus further provides support for real-time remote diagnostics testing such as urine, electrocardiogram (ECG), blood pressure etc. It also provides support for real-time communication through "Sally's Help Button" (panic button/PERS), in case the user needs safety and/or support assistance, with rehabilitation center, mental health providers, family support providers, and or other support systems, including but not limited to an emergency contact.

Moreover, SDDO also provides support for secure Biometric access to ensure proper identification, including but not limited to retina, fingerprint, facial, voice recognition, and/or other means. It further provides support for authentication for secondary access. The authentication may be performed through use of an RFID and/or other means. It also utilizes a scale and/or other sensor for monitoring the stored contents, including but not limited to an optical sensor. This can help to ensure that the proper medication amount was stored and dispensed. This also guards against unauthorized tampering and removal of contents.

The present invention further utilizes a touchpad for the electrocardiogram (ECG) and/or Thermometer sensors. It also utilizes GPS tracking for location monitoring.

a. On the wearable model, said GPS tracker will provide monitoring of the user and the device.

Furthermore, Secure Storage and Dispensing of Opioids (SSDO) apparatus provides "Location Lock" and "Track Me" features to notify if device has moved. It utilizes motion sensors including but not limited to an accelerometer to detect movement falls, and damages due to sudden movement or drops. It further provides Connectivity to social networking support group In another embodiment, Mobile Secure Storage and Dispensing of Opioids (MSSDO) device can be configured as a wearable device to store and dispense Opioids and or other drugs. The Mobile Secure Storage and Dispensing of Opioids (MSSDO) device may be configured to attach to a person's wrist, arm, foot, or other body parts. The Mobile Secure Storage and Dispensing of Opioids (MSSDO) device may further be configured as a Personal Opioids Emergency Response System (POERS) Mobile version of the Secure Storage and Dispensing of Opioids. The Mobile Secure Storage and Dispensing of Opioids (MSSDO) device may utilize a pulse and/or electrocardiogram (ECG) sensor. The Mobile Secure Storage and Dispensing of Opioids (MSSDO) device may further utilize a thermometer, motion sensor, panic button, and/or a biometric sensor, including but not limited to a fingerprint scanner.

BRIEF DESCRIPTION OF THE DRAWINGS

A clear understanding of the key features of the invention summarized above may be had by reference to the appended diagrams/flow charts, which illustrate the method and system of the invention, although it will be understood that such diagrams/flow charts depict preferred embodiments of the invention and, therefore, are not to be considered as limiting its scope with regard to other embodiments which the invention is capable of contemplating. Accordingly.

DETAILED DESCRIPTION OF THE PREFERRED EMBODIMENTS

Although specific embodiments of the present invention will now be described with reference to the drawings, it should be understood that such embodiments are by way of example only and merely illustrative of but a small number of the many possible specific embodiments which can represent applications of the principles of the present invention. Various changes and modifications obvious to one skilled in the art to which the present invention pertains are deemed to be within the spirit, scope and contemplation of the present invention.

It should be noted that references to "an," "one," or "various" embodiments in this disclosure are not necessarily to the same embodiment, and such references contemplate more than one embodiment.

The present invention disclosed herein is a contactless automatic pill dispenser configured to remind a user and to dispense medication to the user, and to provide a system for tracking medication compliance.

Unless otherwise defined, all terms of art, notations and other scientific terms or terminology used herein are intended to have the meanings commonly understood by those of skill in the art to which this invention pertains unless the context clearly indicates otherwise. In some cases, terms with commonly understood meanings are defined herein for clarity and/or for ready reference, and the inclusion of such definitions herein should not necessarily be construed to represent a substantial difference over what is generally understood in the art. Many of the techniques and procedures described or referenced herein are well understood and commonly employed using conventional methodology by those skilled in the art, such as, for example, the widely utilized current good manufacturing practice guidelines.

As used herein the term "computing device" includes a desktop, laptop or tablet computer, as well as a mobile device or any other functionally similar device.

As used herein, the terms "patient," "care giver," "user," and the like all refer to the person who is using the present invention and are meant to be interchangeable and non-limiting.

"Telemetry" refers to any wireless transmission and reception of measured quantities for the purpose of remotely monitoring environmental conditions or equipment parameters.

"Software Application" refers to all computer software that causes a computer to perform useful tasks beyond the running of the computer itself.

Disclosed herein and illustrated in FIGS. 1 through 43 is a Contactless Automatic Pill Dispenser Device 100 in accordance with the present invention.

Figure 1:
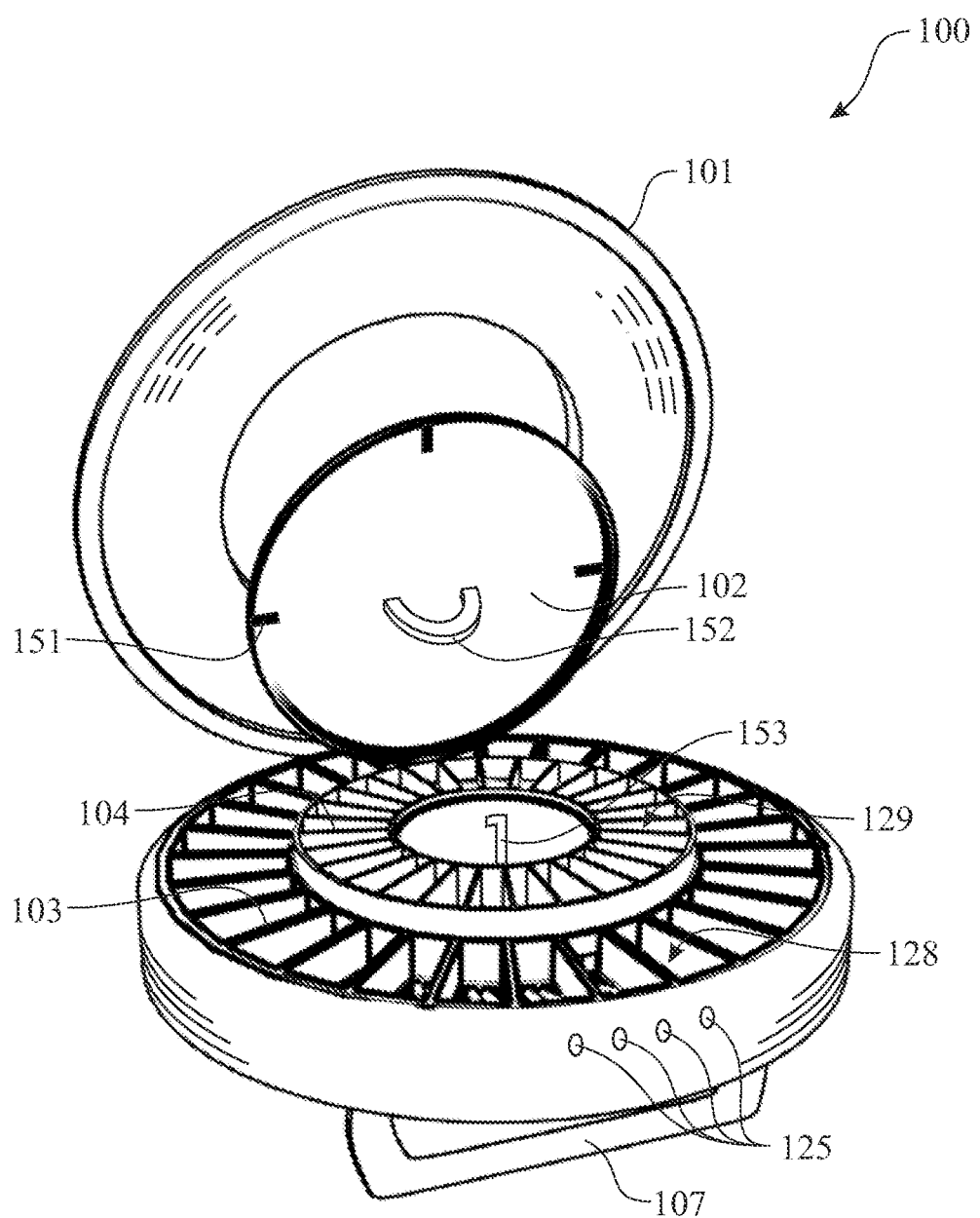
FIG. 1 presents a top, front right side, isometric view of an Opioid dispenser comprising two trays, the illustration presenting each of both trays open.
Figure 2:
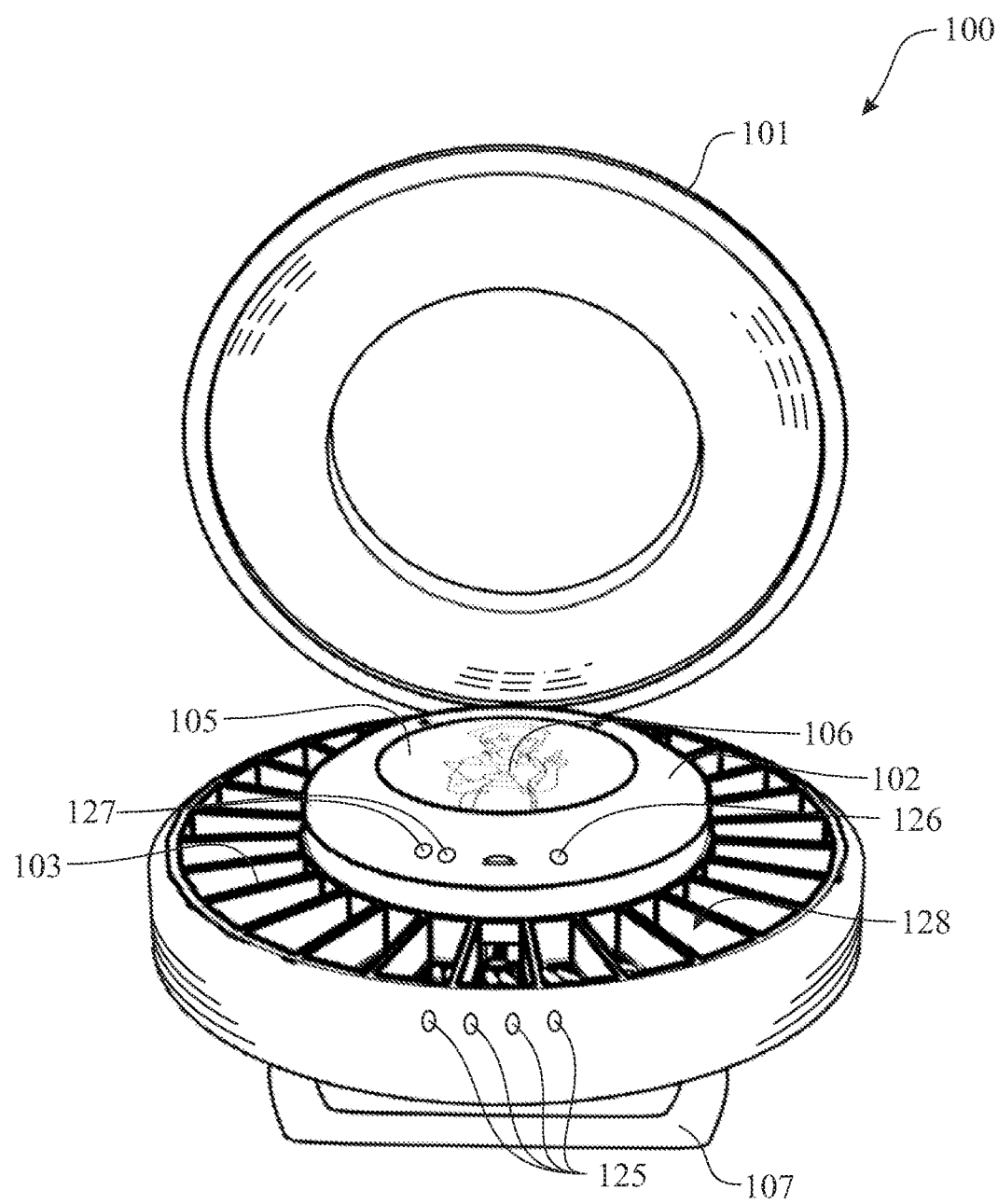
FIG. 2 presents a top, front isometric view of the Opioid dispenser, the illustration presenting the primary tray being the only open tray.
Figure 3:
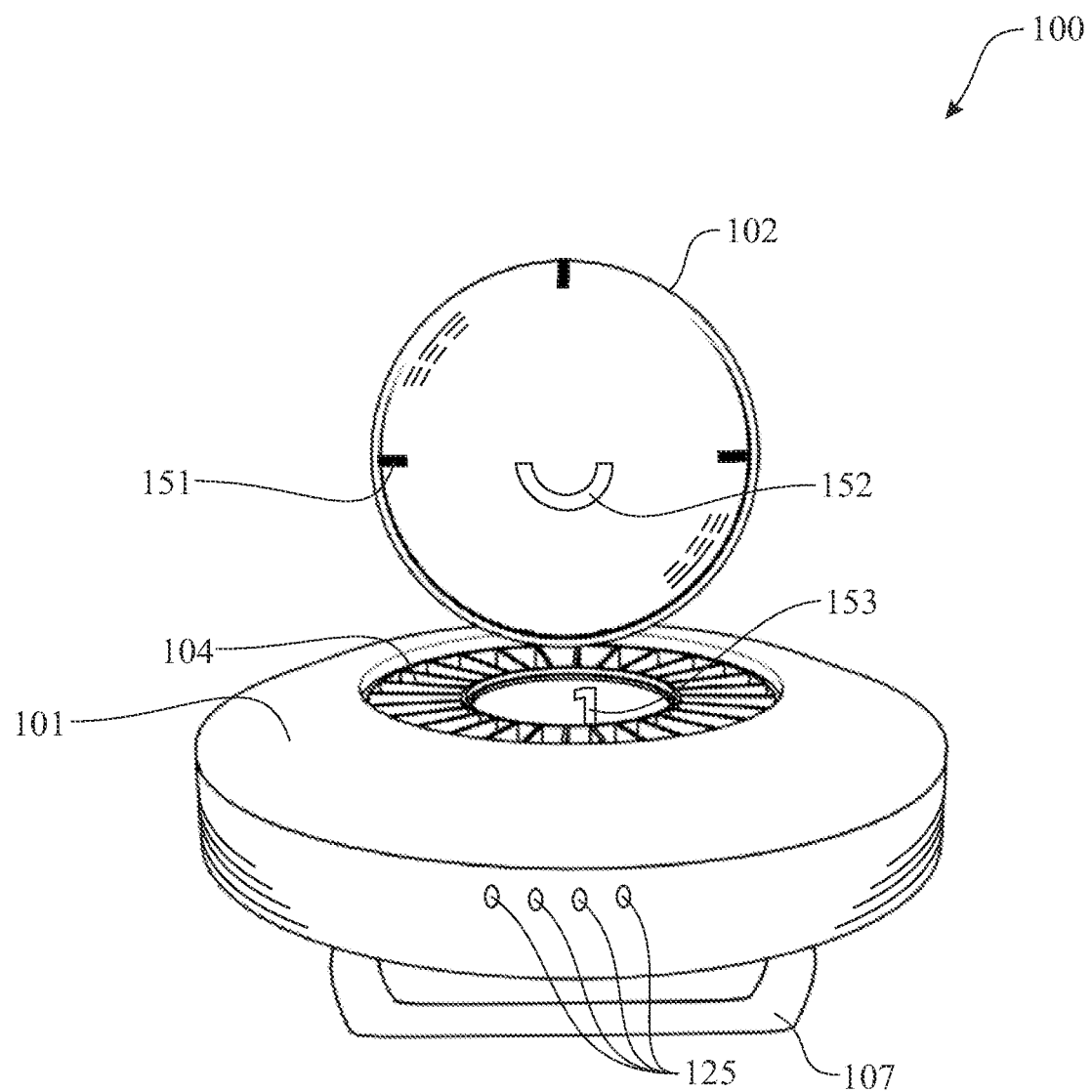
FIG. 3 presents a top, front isometric view of the Opioid dispenser, the illustration presenting the secondary tray being the only open tray, the illustration also presenting legs in an extended configuration.
Figure 4:
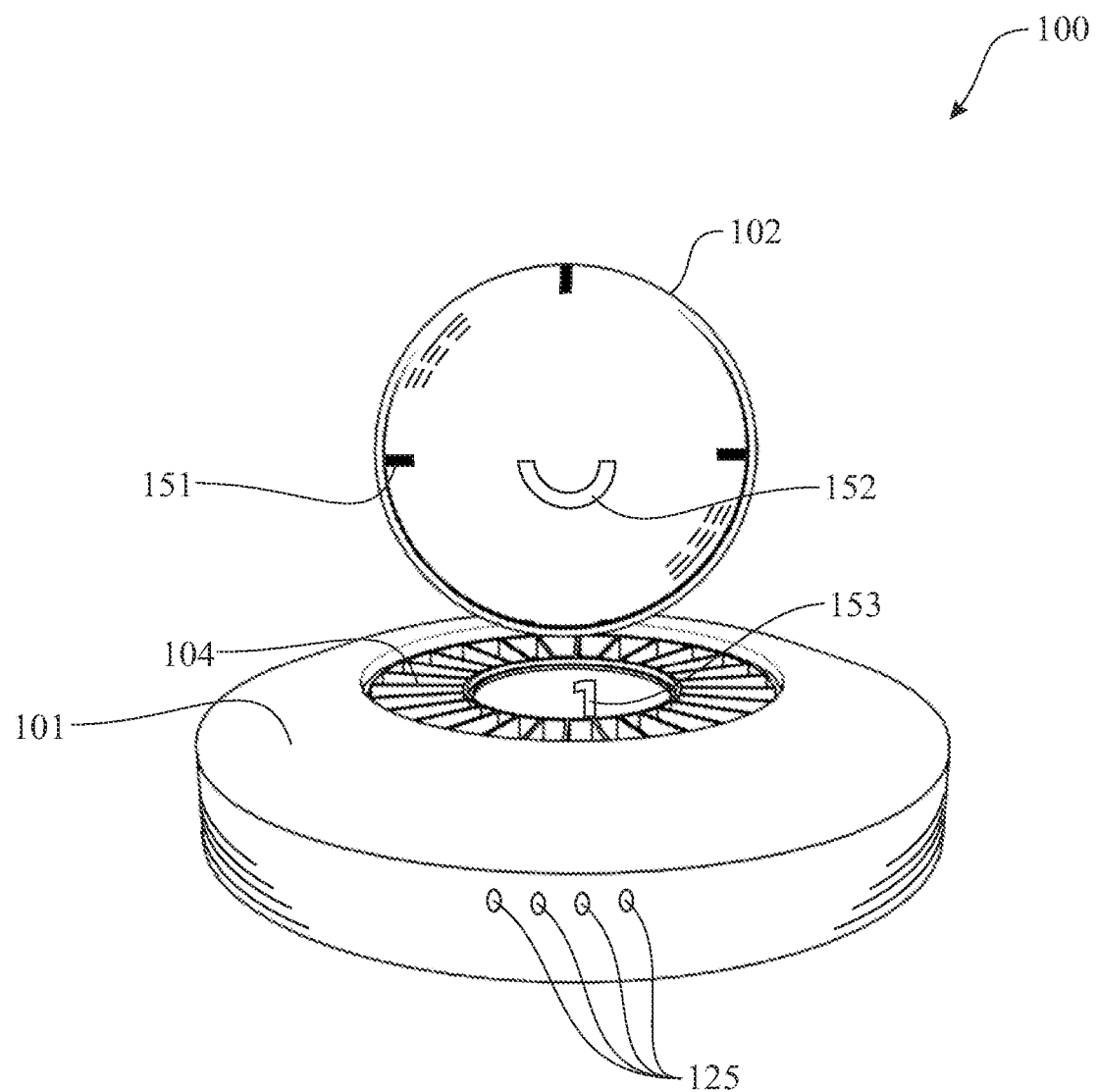
FIG. 4 presents a top, front isometric view of the Opioid dispenser, the illustration presenting the secondary tray being the only open tray, the illustration also presenting the legs in a closed configuration.
Figure 5:
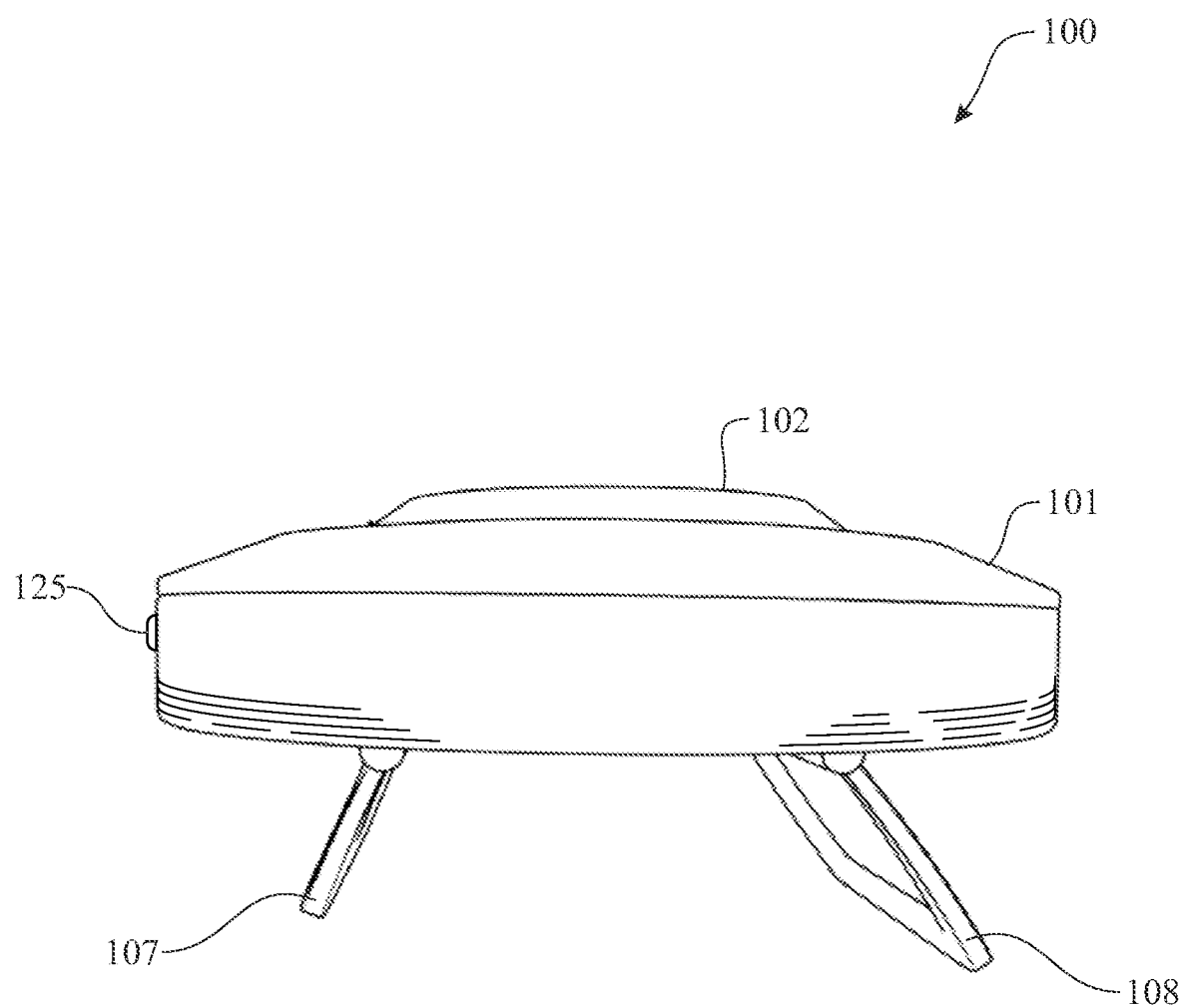
FIG. 5 presents a left side elevation view of the Opioid dispenser, the illustration presenting both trays closed and both legs in an extended configuration.
Figure 6:
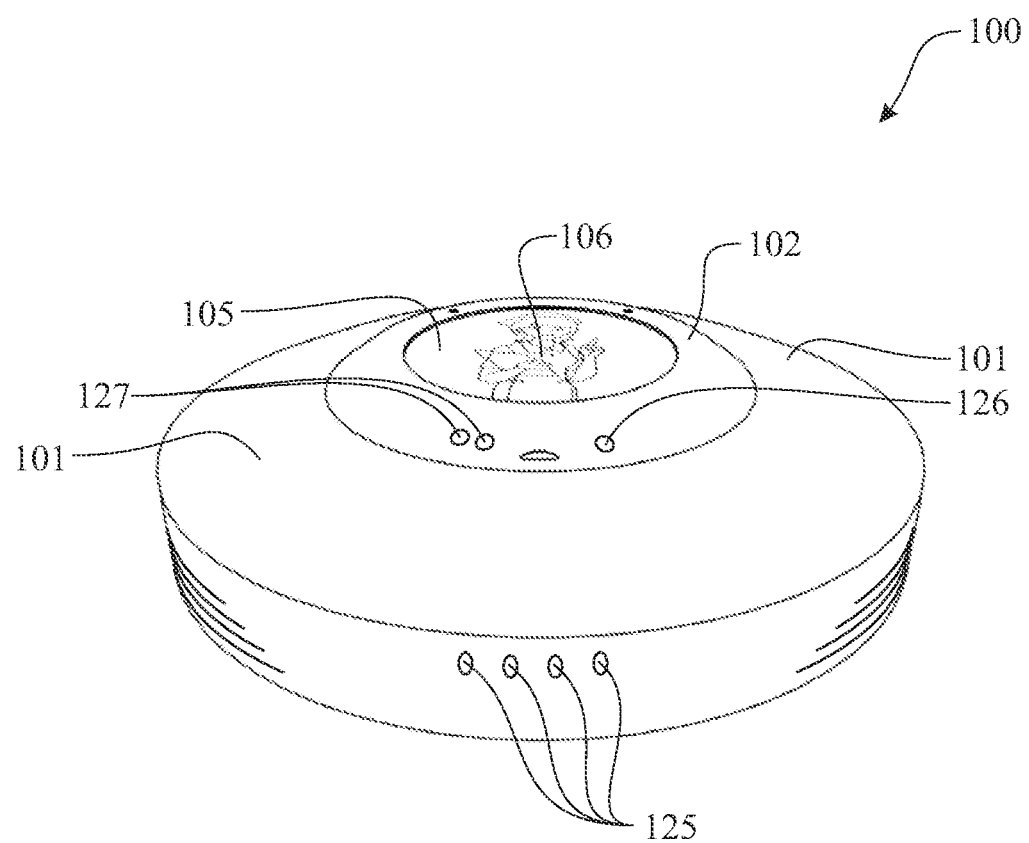
FIG. 6 presents a top, front isometric view of the Opioid dispenser, the illustration presenting=both trays closed and both legs in a retracted configuration.
Figure 7:
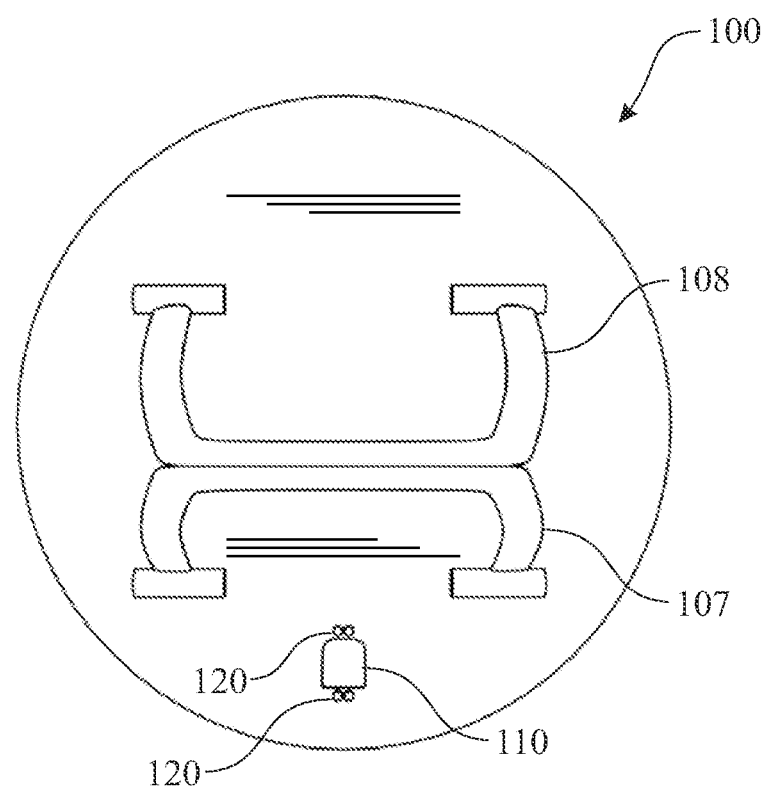
FIG. 7 presents a bottom view of the Opioid dispenser with legs closed.
Figure 8:
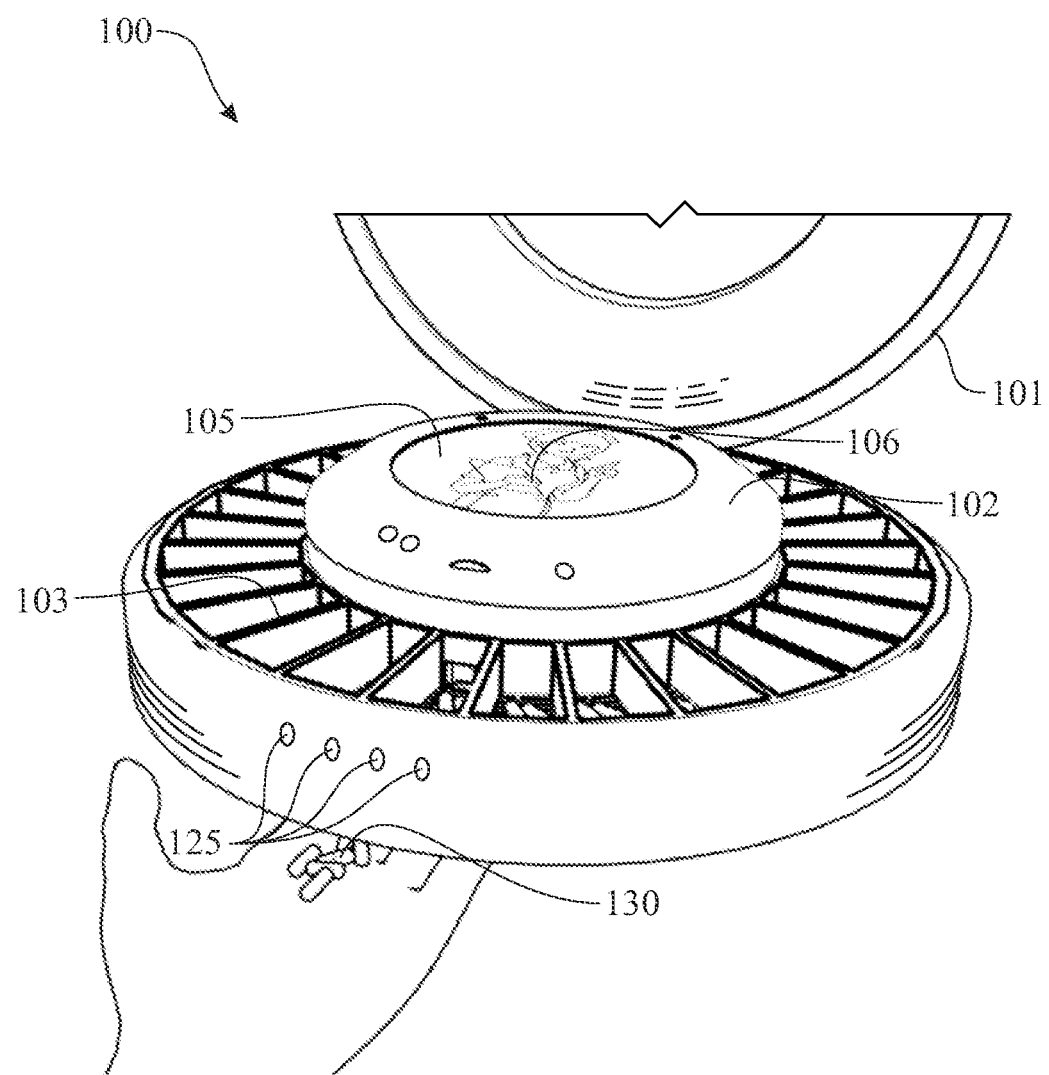
FIG. 8 presents a top, front, left side isometric view of the Opioid dispenser, the illustration presenting manually loaded pills being dispensed from the primary tray.

A Secure Storage for Dispensing of Opioids (SSDO) apparatus 100 is introduced in FIGS. 1 and 2. The shape of the Secure Storage for Dispensing of Opioids (SSDO) is generally circular and includes a round primary medication tray 103 and a similarly rounded secondary medication tray 104; each tray 103, 104 having a parallel rounded cover 101 and a secondary cover 102 respectively. The round primary medication tray 103 includes a primary tray medication compartment 128. The rounded secondary medication tray 104 includes a secondary tray medication compartment 129. The two compartments 128, 129 house the medication until the medication is dispensed.

Figure 15:
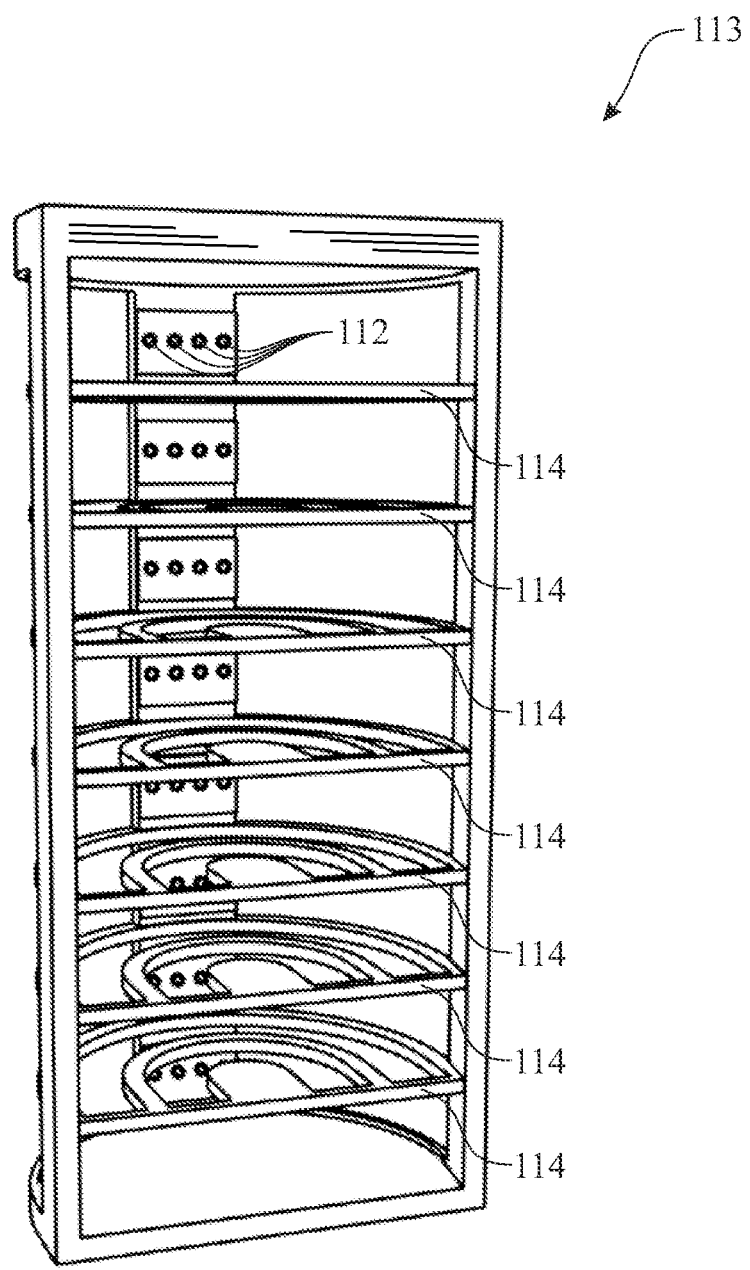
FIG. 15 presents a front, right side isometric view of an exemplary docking station, the docking station is shown in an empty configuration.
Figure 16:
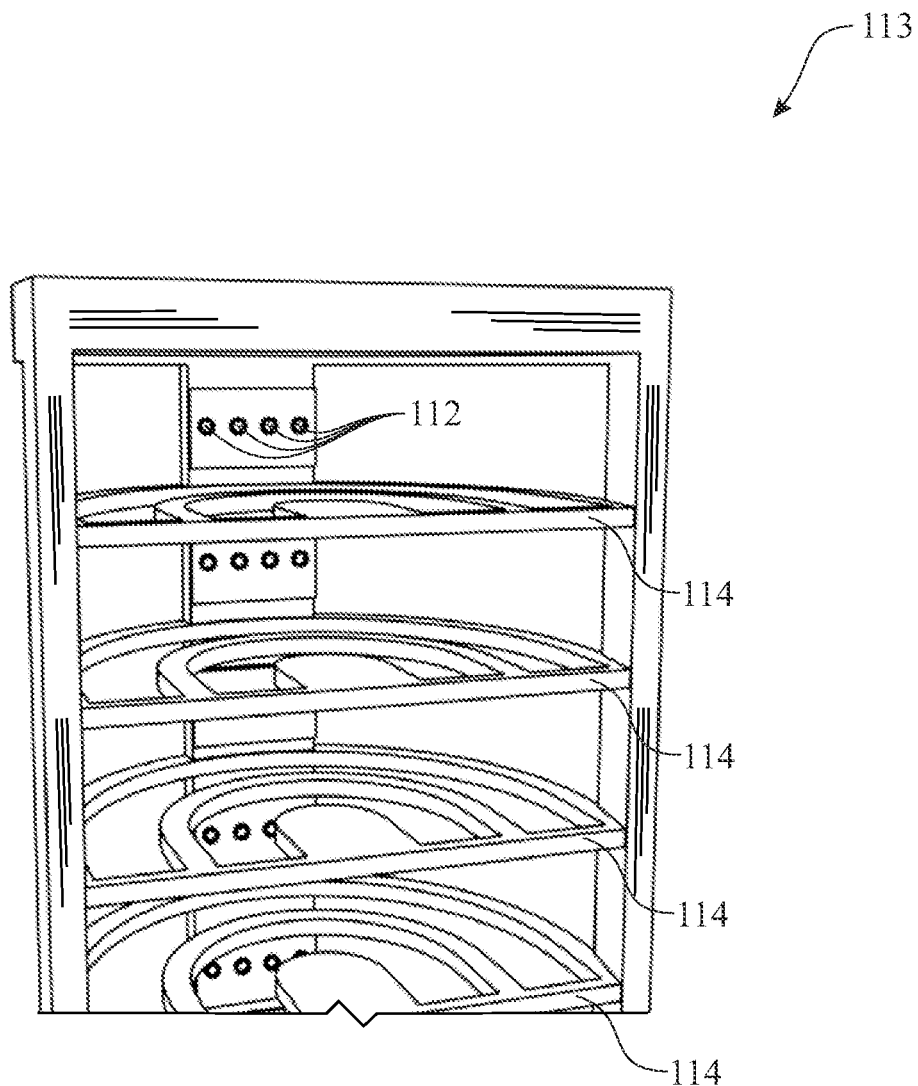
FIG. 16 presents an enlarged front, right side isometric view of the docking station originally introduced in FIG. 15.
Figure 17:
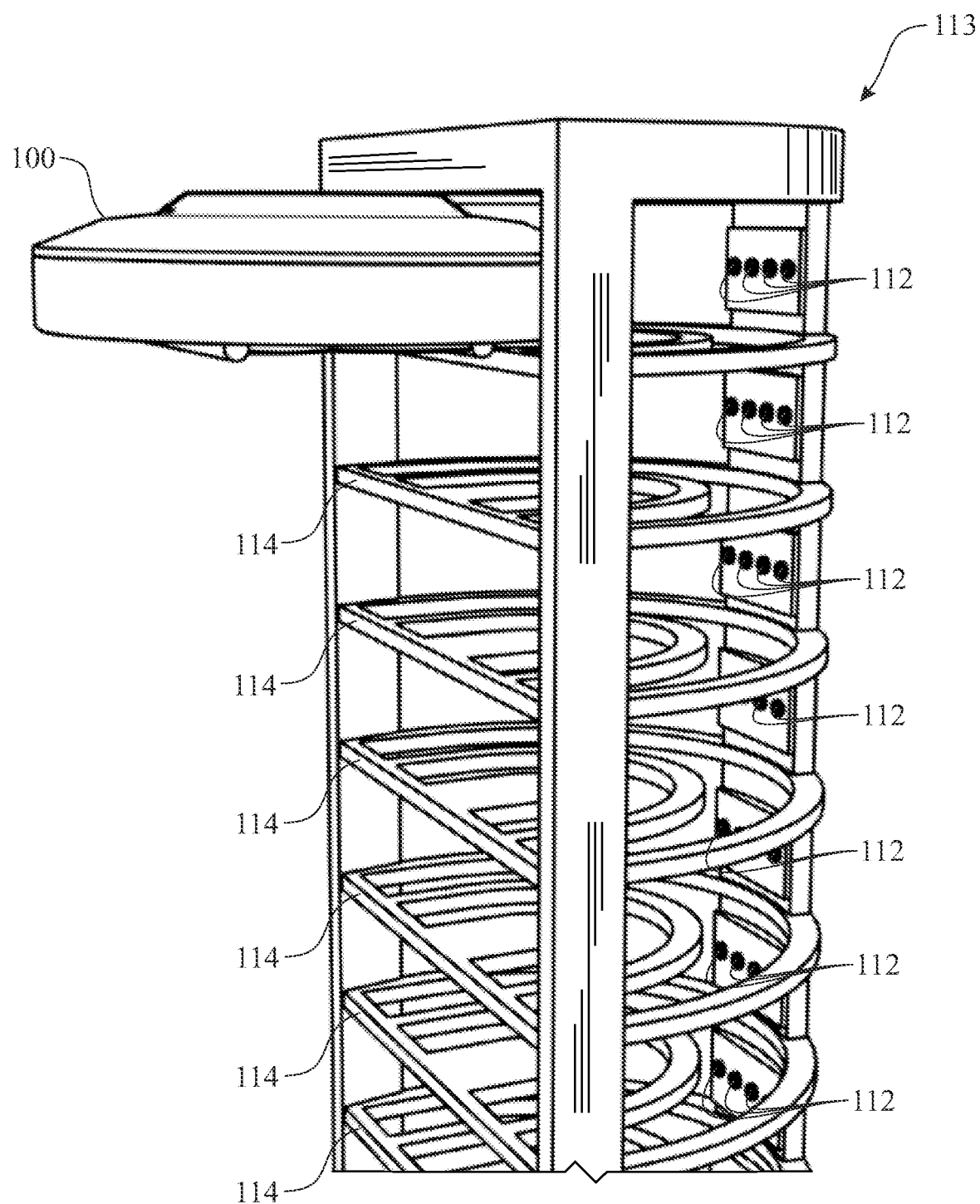
FIG. 17 presents a front, left side isometric view of the docking station, the illustration presenting one Opioids dispenser being partially inserted (docked) into the docking station.
Figure 18:
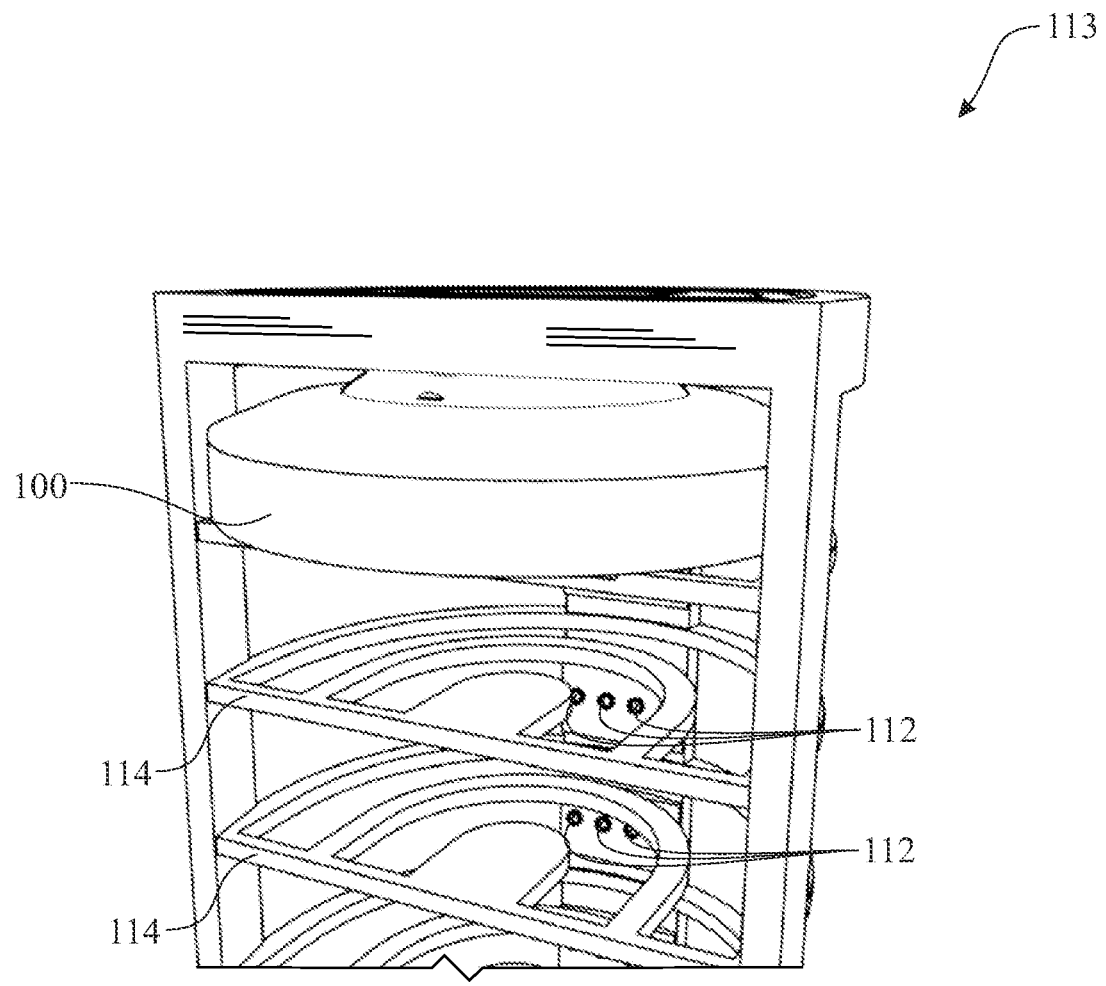
FIG. 18 presents an enlarged front, left side isometric view of the docking station, the illustration presenting one Opioids dispenser being fully inserted (docked) into the docking station.
Figure 19:
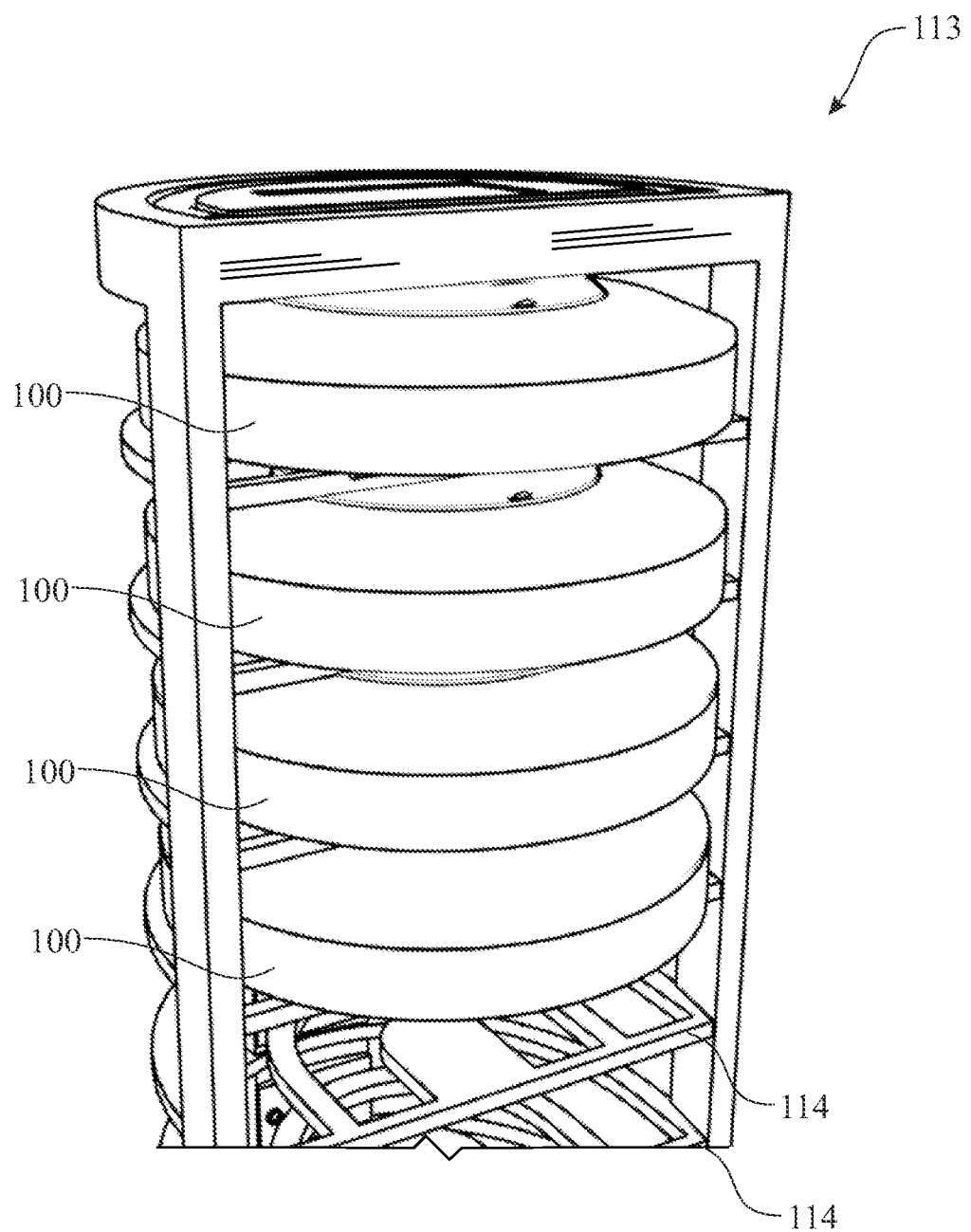
FIG. 19 presents an enlarged front, right side isometric view of the docking station, the illustration presenting multiple Opioids dispensers being fully inserted (docked) into the docking station.
Figure 20:
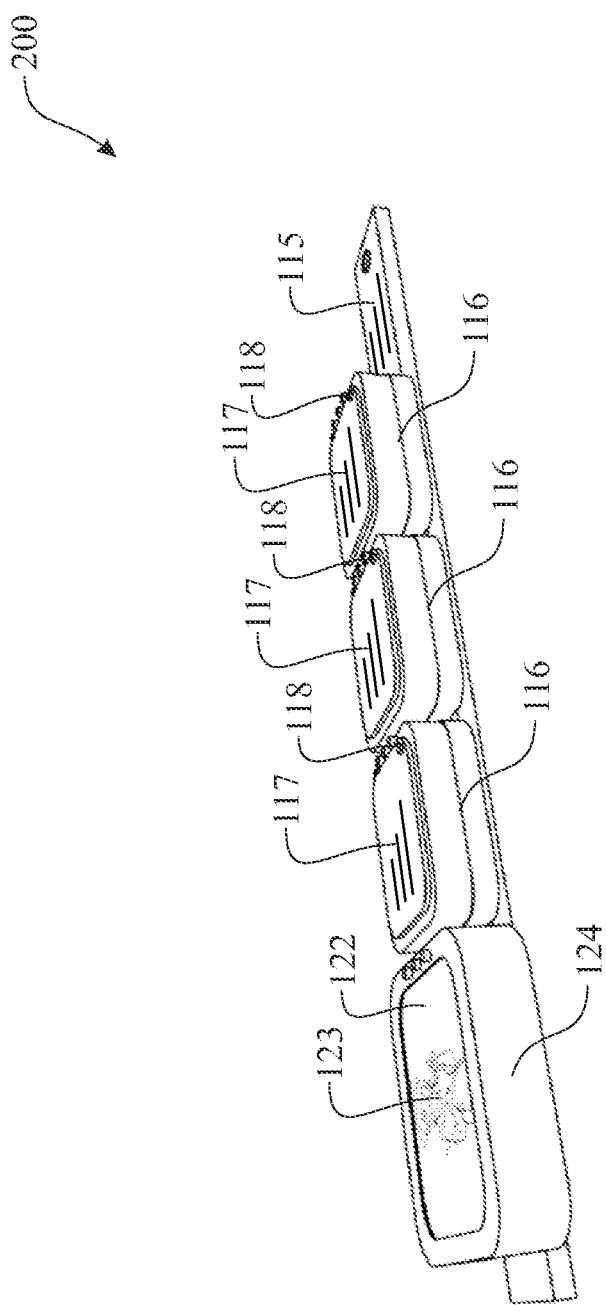
FIG. 20 presents a top, side perspective view of an exemplary wrist/ankle bracelet, the exemplary wrist/ankle bracelet comprising a display unit and three medication compartments.
Figure 21:
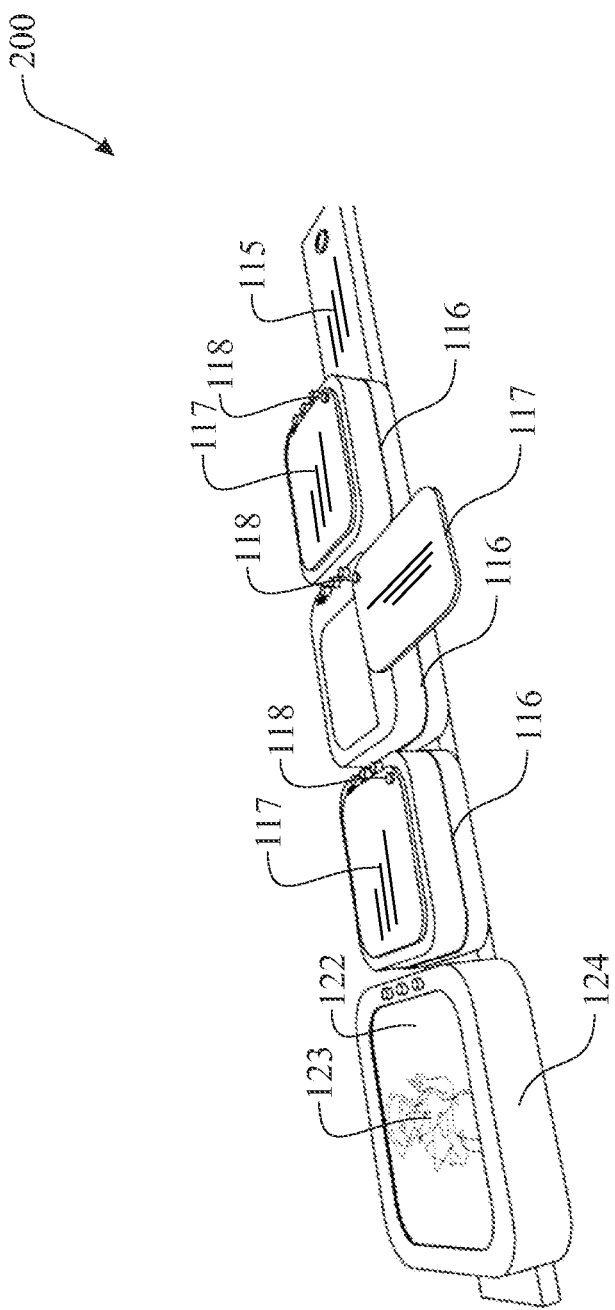
FIG. 21 presents a top, side perspective view of the exemplary wrist/ankle bracelet originally introduced in FIG. 20, the illustration presenting the middle medication compartment being shown in an open position.
Figure 22:
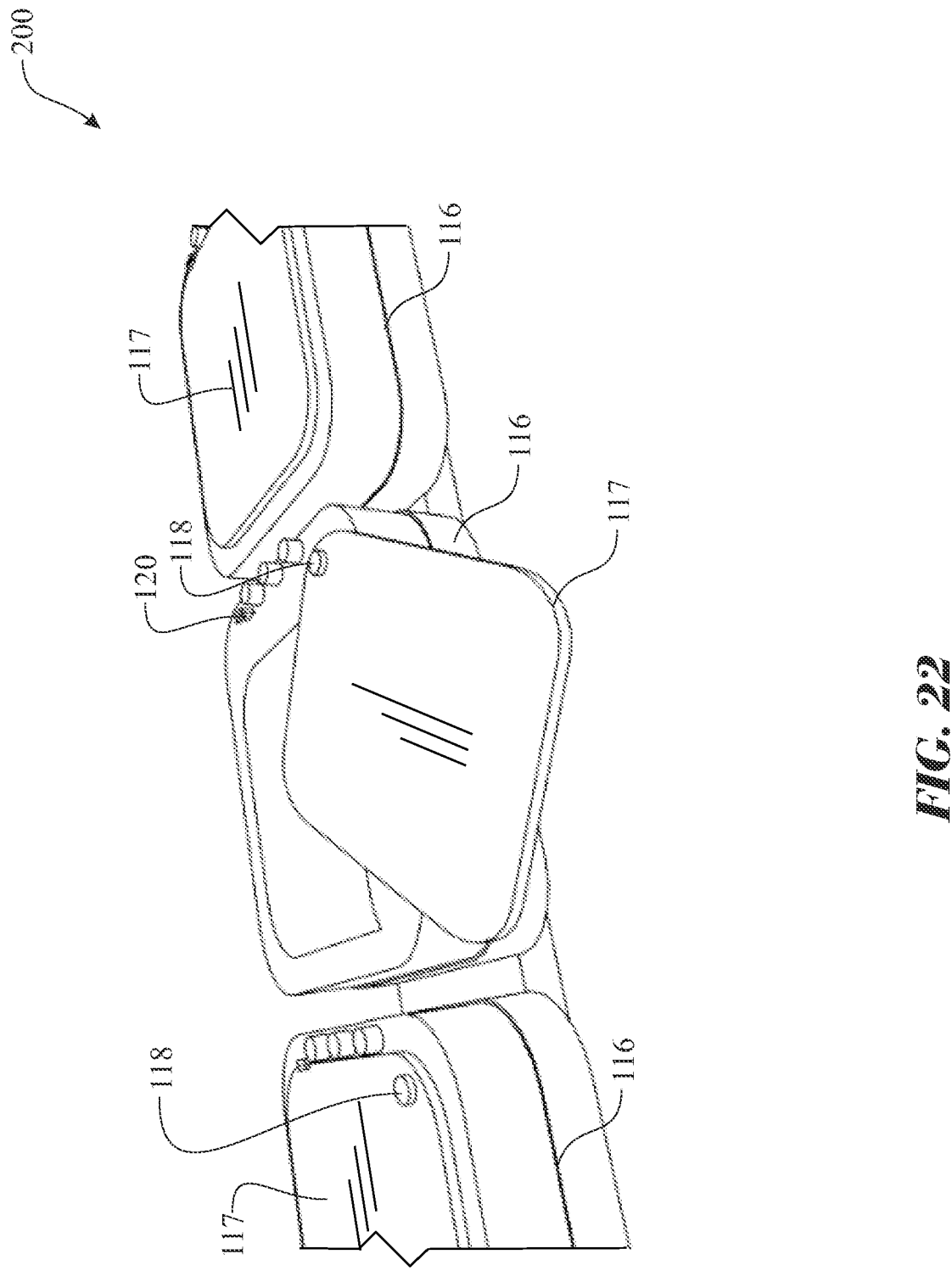
FIG. 22 presents an enlarged top, side perspective view of the exemplary wrist/ankle bracelet originally introduced in FIG. 20, the illustration presenting the middle medication compartment being shown in a partially open position.
Figure 23:
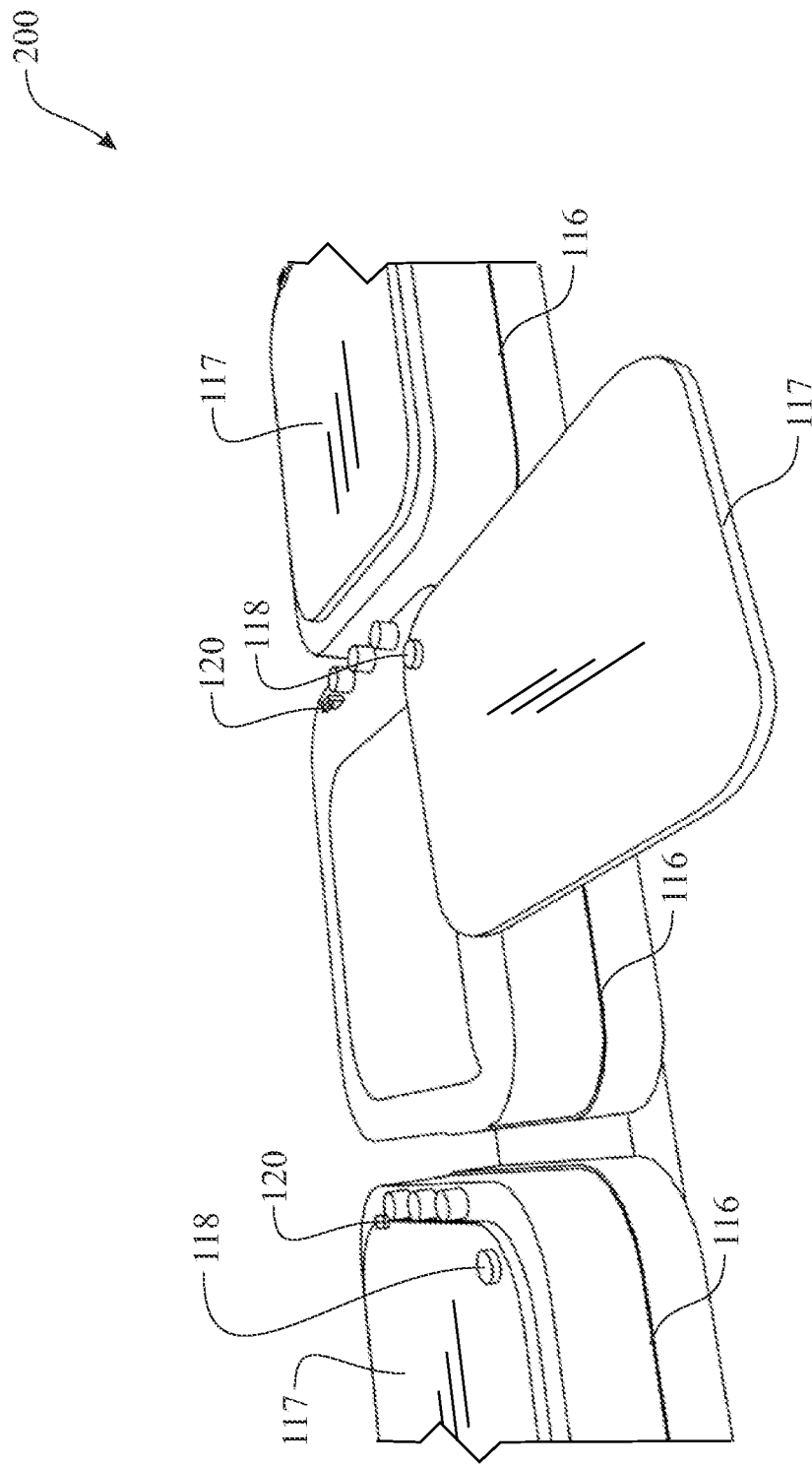
FIG. 23 presents an enlarged top, side perspective view of the exemplary wrist/ankle bracelet originally introduced in FIG. 20, the illustration presenting the middle medication compartment being shown in a fully open position.
Figure 24:
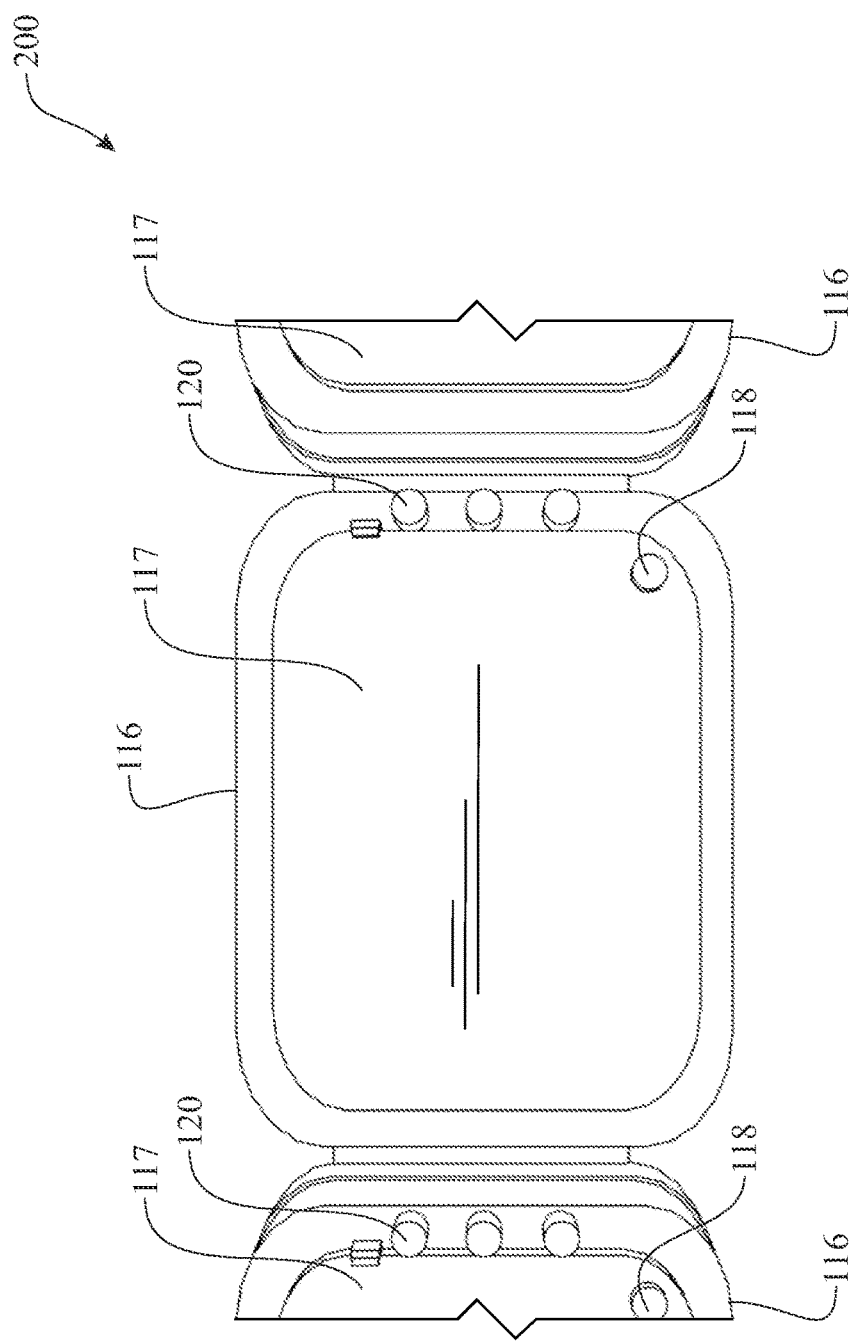
FIG. 24 presents an enlarged top view of the exemplary wrist/ankle bracelet originally introduced in FIG. 20, the illustration presenting the three medication compartments being shown in a closed position.
Figure 25:
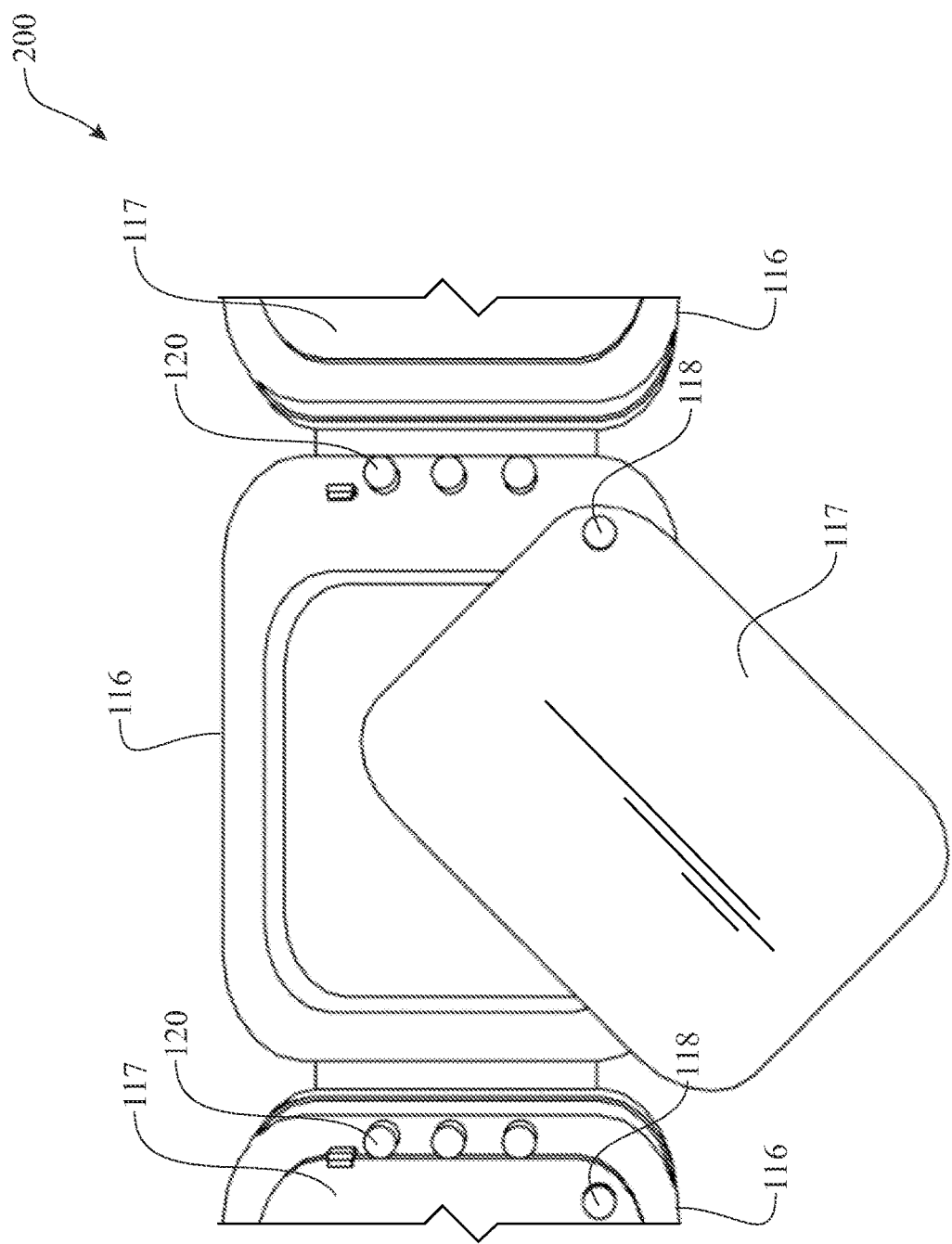
FIG. 25 presents an enlarged top view of the exemplary wrist/ankle bracelet originally introduced in FIG. 20, the illustration presenting the middle medication compartment being shown in a partially open position.
Figure 26:
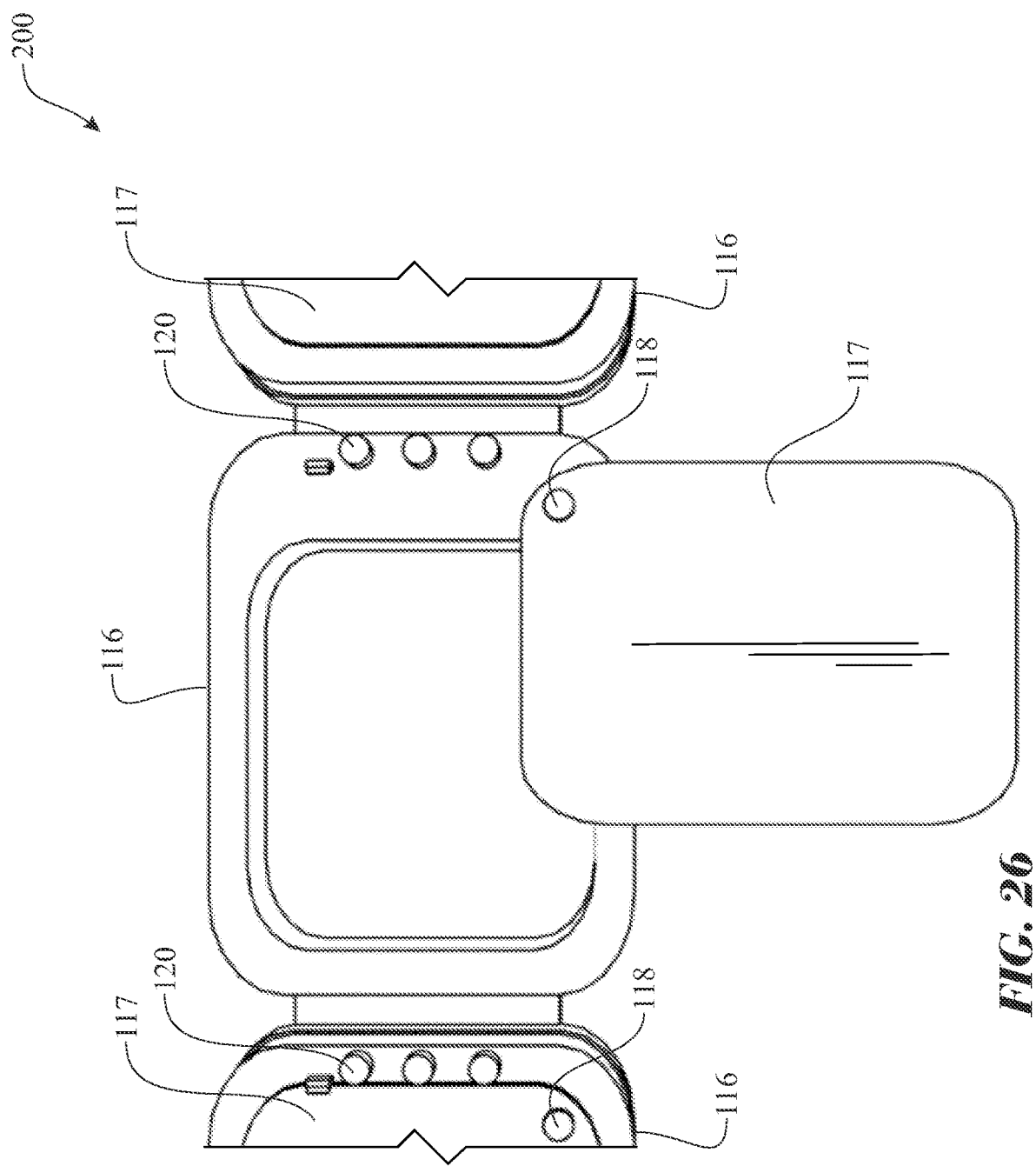
FIG. 26 presents an enlarged top view of the exemplary wrist/ankle bracelet originally introduced in FIG. 20, the illustration presenting the middle medication compartment being shown in an open position.
Figure 27:
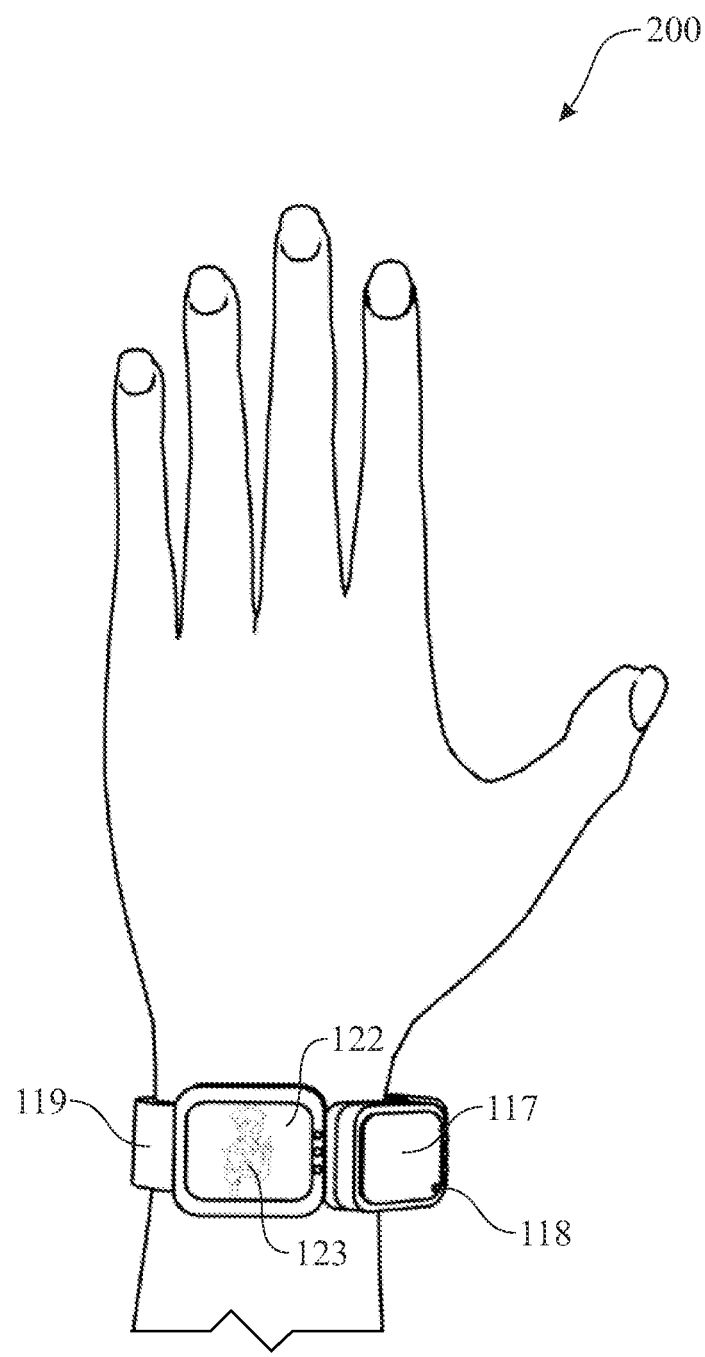
FIG. 27 presents a top view of the exemplary wrist/ankle bracelet originally introduced in FIG. 20, the illustration presenting the exemplary wrist/ankle bracelet shown being worn as a wrist bracelet.
Figure 28:
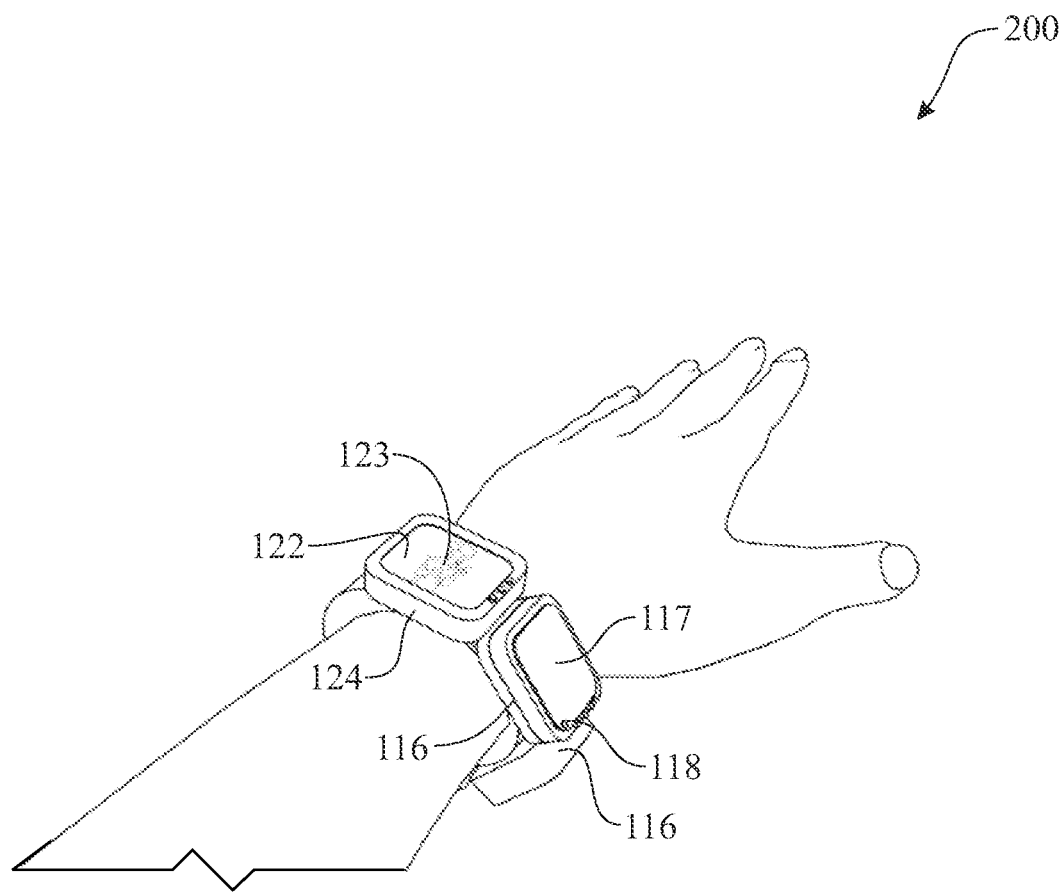
FIG. 28 presents a top, side, rear perspective view of the wrist bracelet as illustrated in FIG. 27.
Figure 29:
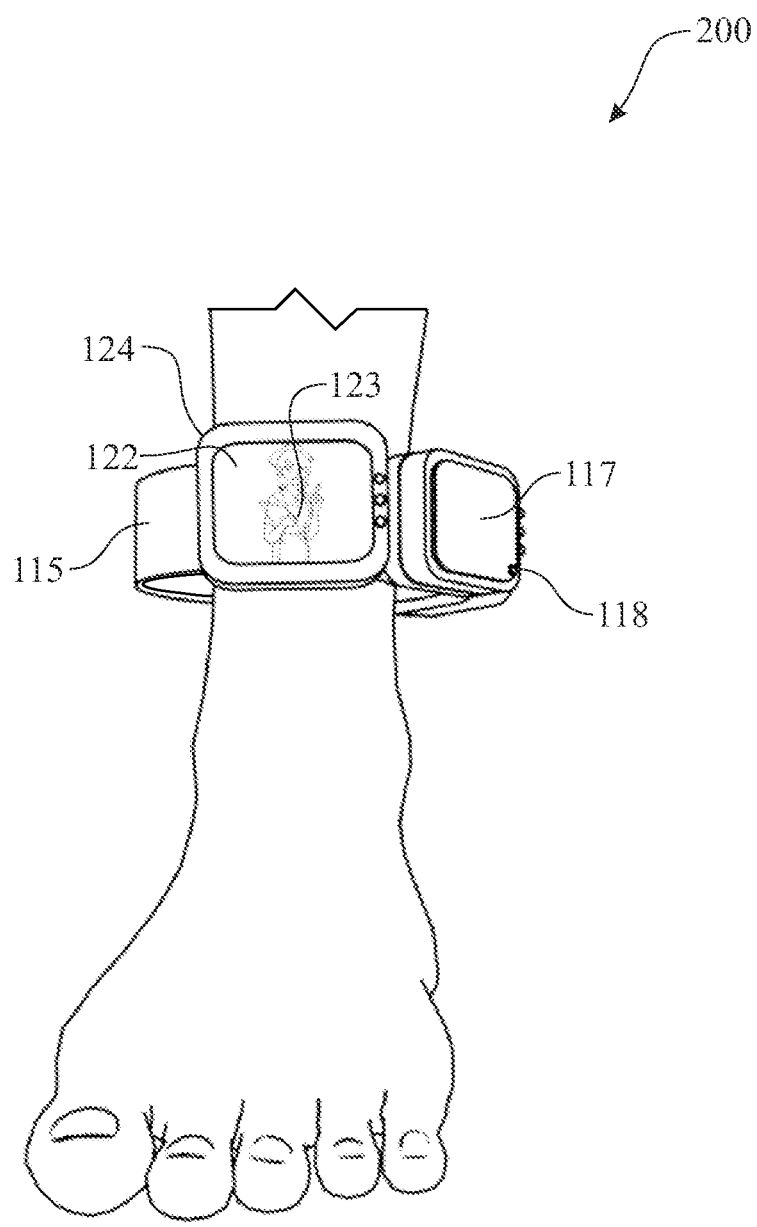
FIG. 29 presents a front view of the exemplary wrist/ankle bracelet originally introduced in FIG. 20, the illustration presenting the exemplary wrist/ankle bracelet shown being worn as an ankle bracelet, the illustration showing the display unit.
Figure 30:
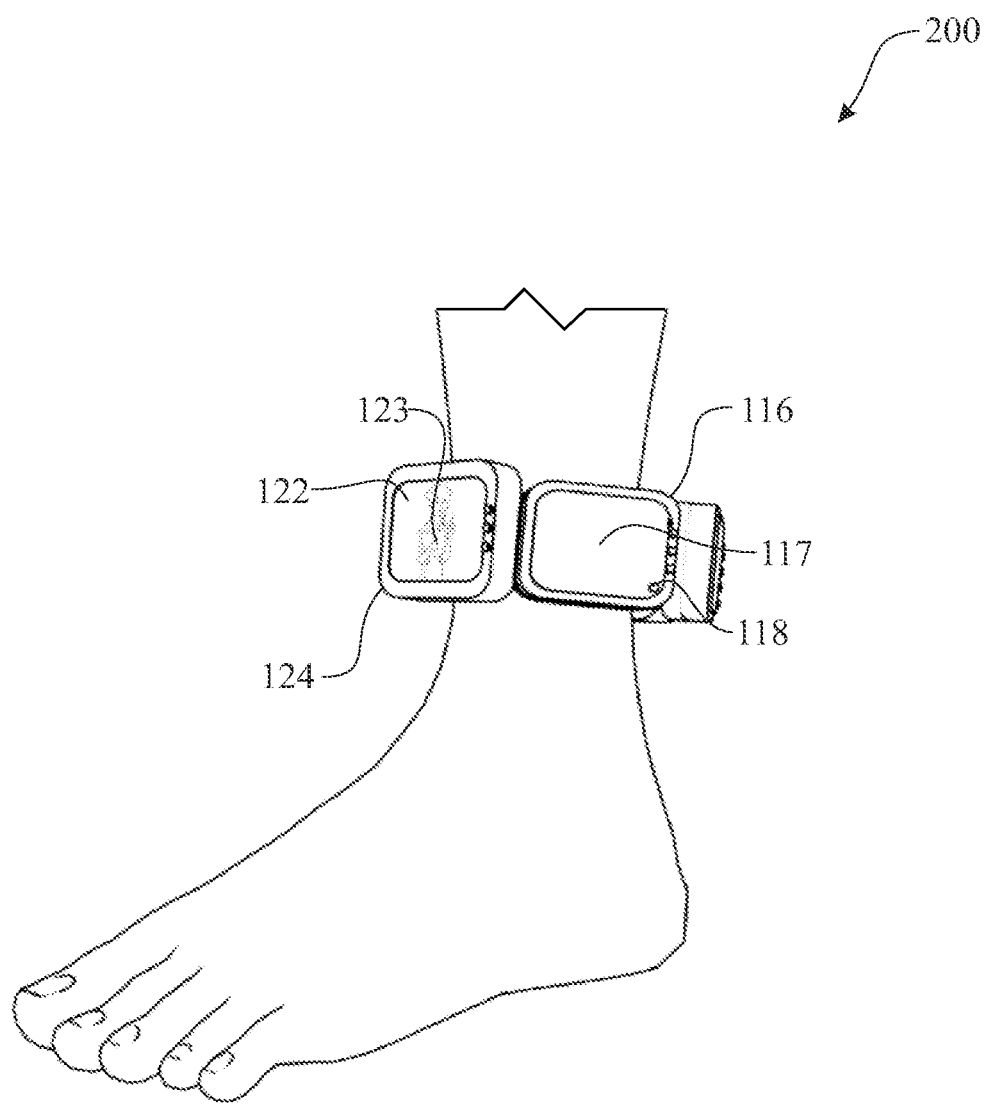
FIG. 30 presents a side view of the exemplary wrist/ankle bracelet originally introduced in FIG. 20, the illustration presenting the exemplary wrist/ankle bracelet shown being worn as an ankle bracelet, the illustration showing the display unit and an adjacent medicine compartment.
Figure 31:
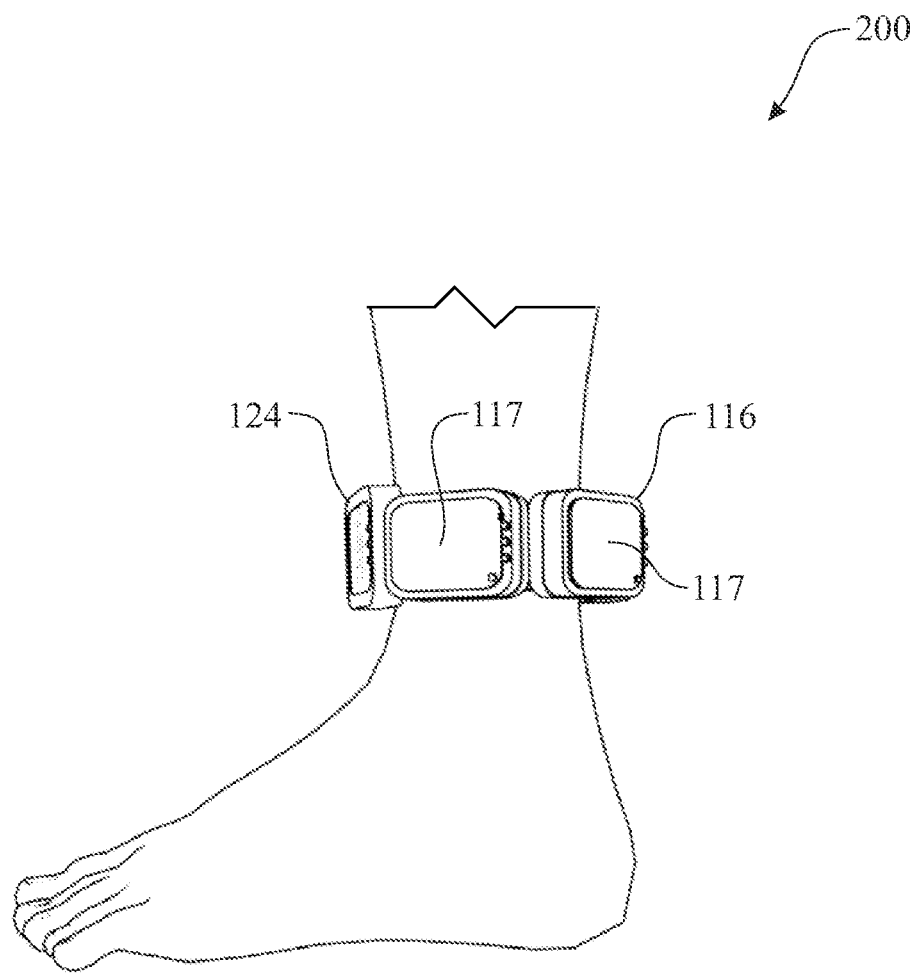
FIG. 31 presents a side view of the exemplary wrist/ankle bracelet originally introduced in FIG. 20, the illustration presenting the exemplary wrist/ankle bracelet shown being worn as an ankle bracelet, the illustration showing the display unit and two medication compartments.
Figure 32:
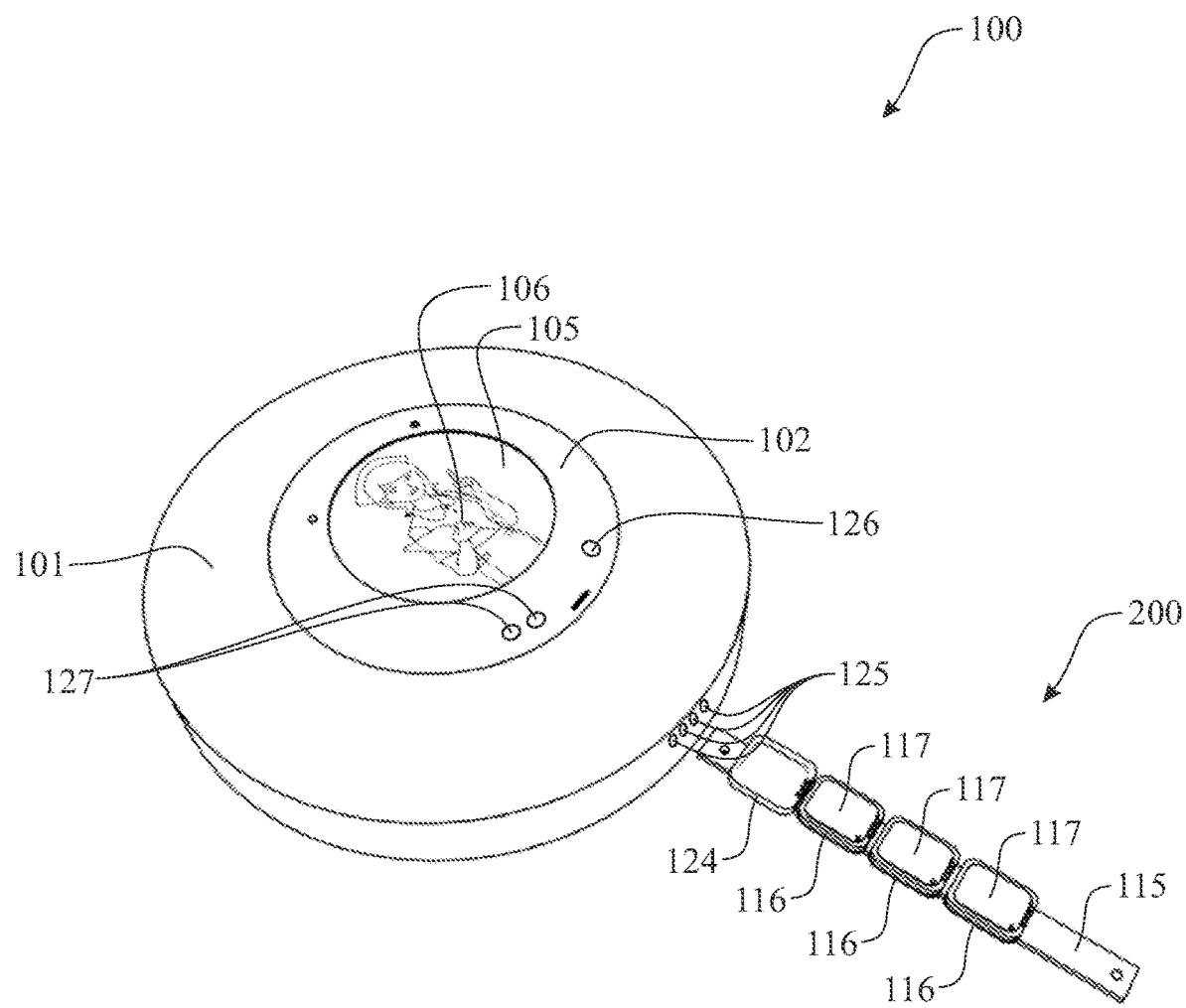
FIG. 32 presents a top, right side isometric view of the Opioids dispenser originally introduced in FIG. 1, the illustration presenting the exemplary wrist/ankle bracelet originally introduced in FIG. 20 being docked with the Opioids dispenser.
Figure 33:
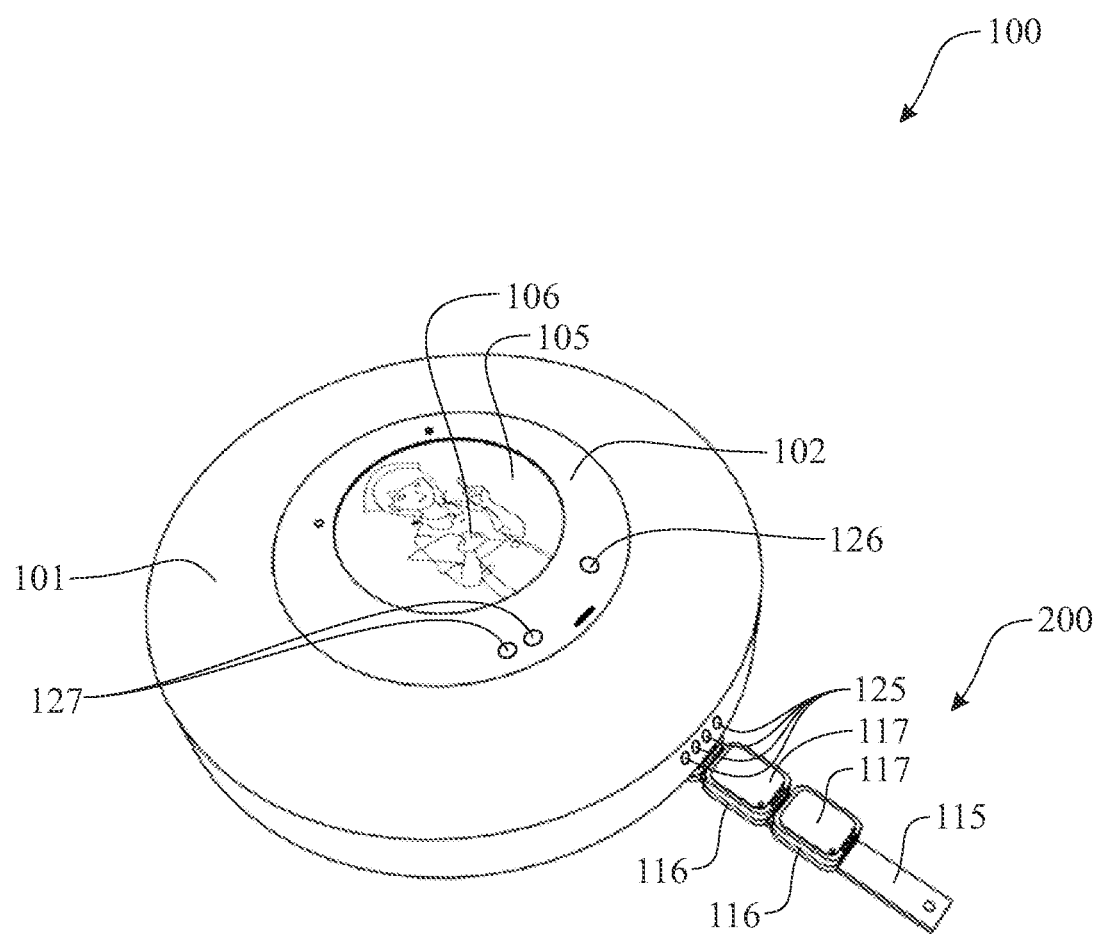
FIG. 33 a top, right side isometric view of the Opioids dispenser originally introduced in FIG. 1, the illustration presenting the exemplary wrist/ankle bracelet originally introduced in FIG. 20 being docked with the Opioids dispenser.
Figure 34:
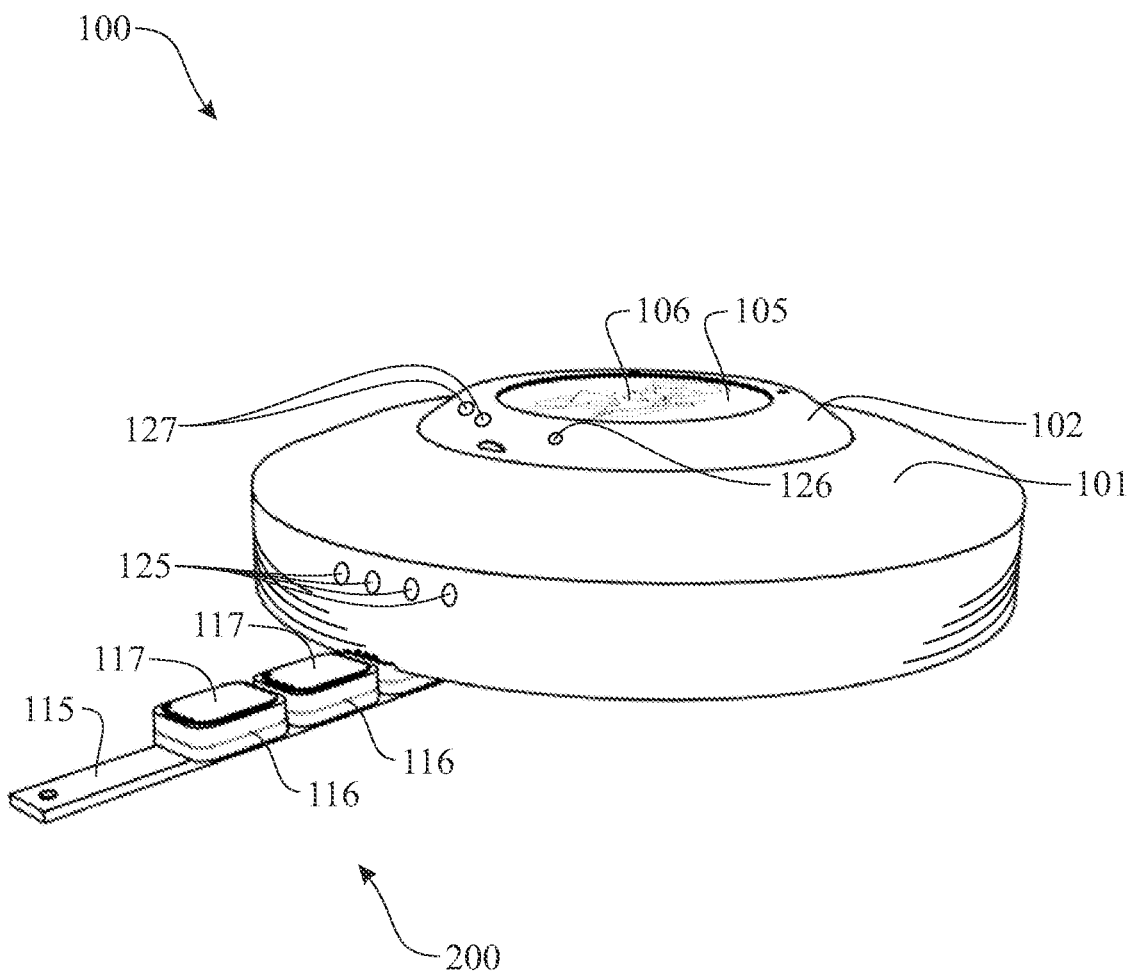
FIG. 34 shows a top, left side isometric view of the Opioids dispenser originally introduced in FIG. 1, the illustration presenting the exemplary wrist/ankle bracelet originally introduced in FIG. 20 being docked with the Opioids dispenser.
Figure 35:
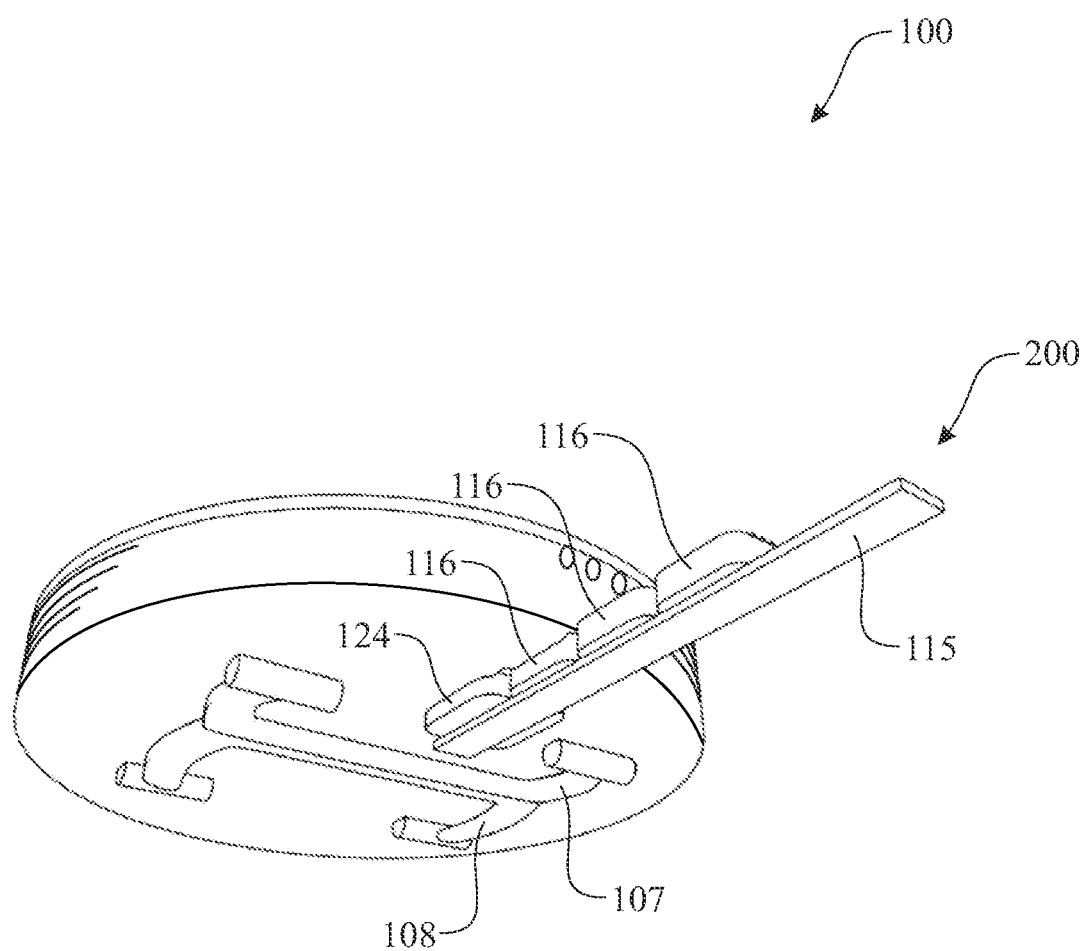
FIG. 35 shows a bottom, right side view of the Opioids dispenser originally introduced in FIG. 1, the illustration presenting the exemplary wrist/ankle bracelet originally introduced in FIG. 20 being docked with the Opioids dispenser.
Figure 36:
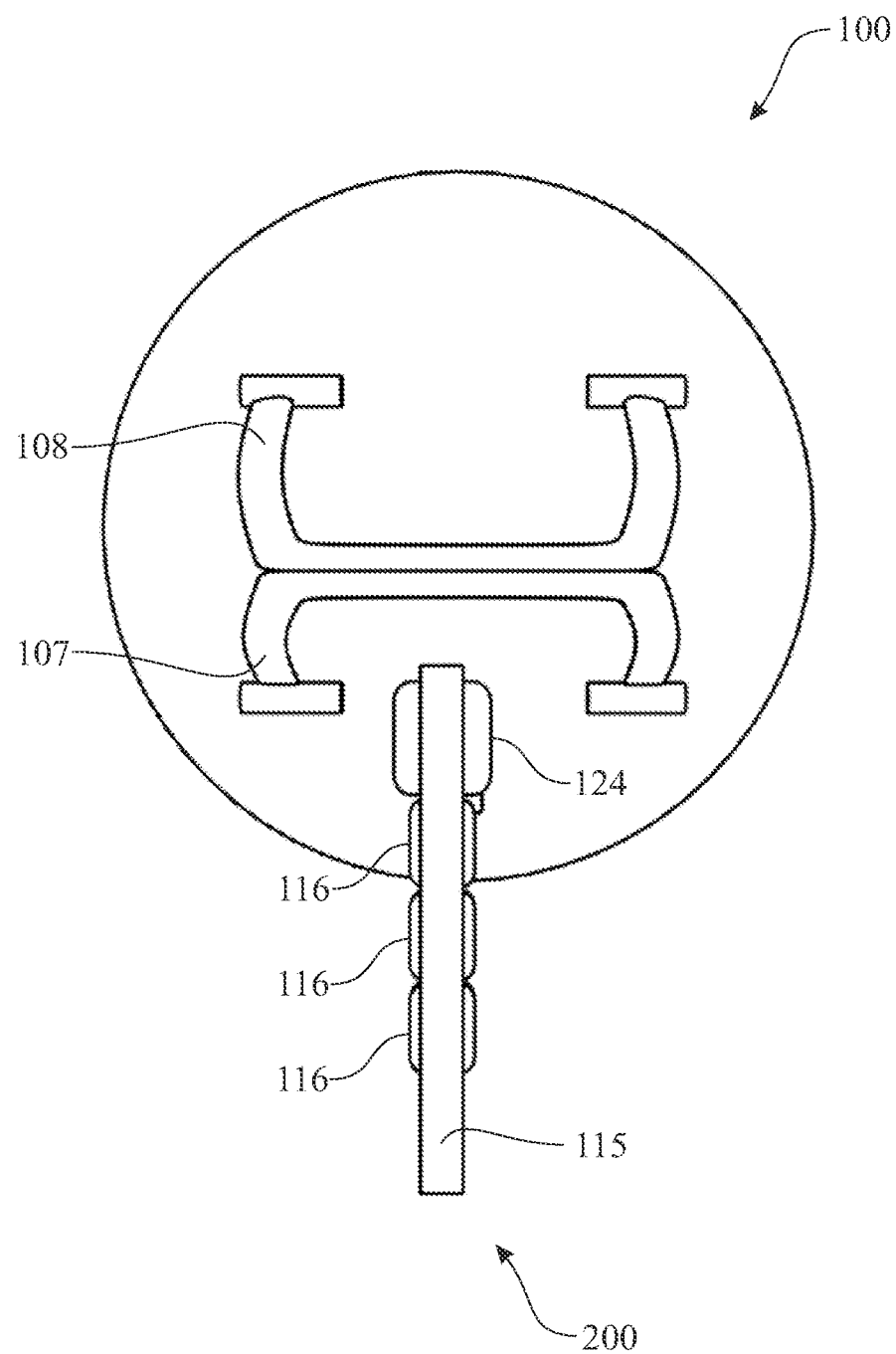
FIG. 36 presents a bottom view of the Opioids dispenser originally introduced in FIG. 1, the illustration presenting the exemplary wrist/ankle bracelet originally introduced in FIG. 20 being docked with the Opioids dispenser.

The secondary cover 102 may or may not have a port for microphone 126 and speaker 127 which is recessed respective to the top cover 101. The secondary cover 102 also houses a secondary tray cover locking harness 152 and a dual tray cover interconnected locking shaft 153 which is used to lock the device, preventing unauthorized access and tampering. The Secure Storage for Dispensing of Opioids (SSDO) apparatus 100 includes a display unit 105 used as a graphical user interface (GUI) for the various functions of the Secure Storage for Dispensing of Opioids (SSDO) apparatus 100 and can house a mobile computing device and an Avatar 106. The mobile computing device can be embedded into the current setup and may be a separate detachable unit. The Secure Storage for Dispensing of Opioids (SSDO) apparatus 100 can include a set of legs 107, one in the back and the other in the front. The Secure Storage for Dispensing of Opioids (SSDO) apparatus 100 can be charged through charging contacts 125. The charging contacts 125 can also provide a connection to the charging contacts 112 within each storage shelf 114 of a storage cart (docking station) 113 (FIG. 15).

Referring to FIGS. 3 through 8, when in use, the Secure Storage for Dispensing of Opioids (SSDO) apparatus 100, the top cover 101 securely covers the manually loaded medication as well as the sealed blister pack 109 medication placed in the primary medication tray 103. Meanwhile, the secondary mediation tray cover 102 securely covers the secondary medication tray 104 of the Secure Storage for Dispensing of Opioids (SSDO) apparatus 100 which contains manually loaded supplemental medications, vitamins and other pills 130. The top cover 104 further utilizes a tamper proof dual lock mechanism to securely lock access to medication in both the primary medication tray 103 as well as the secondary medication tray 104 wherein a motorized shaft securely anchors the access cover 102 of the inner rotary tray 104 and furthermore, a plurality of sliding shafts 151 extend out of the inner rotary tray access cover 102 and protrude into matching holes (not shown) within outer rotary tray access cover 101 to interlock and secure the two rotary access covers 101, 102. The secondary mediation tray cover 102 for secondary mediation tray 104 also comprises of an embedded touch display screen 105, a microphone 126 and a speaker 127 which allow the artificial intelligence avatar 106 (FIG. 8) as well as the remote operators and caregivers to interactively communicate with the user.

The primary medication tray 103 of the Secure Storage for Dispensing of Opioids (SSDO) apparatus 100, can hold both manually loaded pills 130 as well as a sealed blister pack 109 (described in FIGS. 9 through 14). The primary medication tray 103 comprises multiple medication compartments 128 containing Opioids and other medications for one or more time instances during a day such as morning, noon, afternoon and evening, as well as one or more days of the week. The primary medication tray 103 utilizes a motor 251 to rotate and present the medication stored in each medication compartment at the appropriate time and day of the week. Medication contained within the sealed blister pack 109 placed in the primary medication tray 103 can be dispensed utilizing a punch lever 111 and the supporting motor and electronic 253. A medication dispensing schedule for the primary medication tray 103, Blister pack 109 and the secondary supplemental medication tray 104 of the Secure Storage for Dispensing of Opioids (SSDO) apparatus 100 can be programmed locally by utilizing the artificial intelligence Avatar assistant 106 as well as by remote caregivers and physicians utilizing the wireless module 240. The artificial intelligence virtual assistant Avatar 106 further utilizes text to speech, speech to text and Natural Language Processing NLP 223 technology to interactively communicate with the user, triage the user and gather relevant information regarding user's health status.

The secondary medication tray 104 of Secure Storage for Dispensing of Opioids (SSDO) apparatus 100 contains manually loaded supplemental medications, vitamins, and other pills 130. The secondary medication tray 104 comprises of multiple medication compartments 129 containing vitamins, supplemental medication and new additions to regular medication contained in the primary medication try 103.

Dispensing of the medications contained in each of the secondary medication tray 104 compartment 129 can be programmed to dispense at:

a. Simultaneously, with the medication in the primary medication tray compartments at the scheduled time instance such as morning, noon, afternoon and evening, as well as the scheduled day of the week.

b. At a pre-programmed time interval prior to the dispensing of the medication in the primary medication tray compartments at the scheduled time instance such as morning, noon, afternoon and evening, as well as the scheduled day of the week.

c. At a pre-programmed time interval after the dispensing of the medication in the primary medication tray compartments at the scheduled time instance such as morning, noon, afternoon and evening, as well as the scheduled day of the week The secondary tray cover 102 for secondary mediation tray 104 further comprises an embedded touch display screen 105 or a mobile device 264, such as a mobile phone or a tablet, as well as a microphone 126 and speaker 127, wherein the microphone 126 and the speaker 127 allow the artificial intelligence Avatar assist 106 as well as the remote operators and caregivers to interactively communicate with the user.

The display unit 105 of the Secure Storage for Dispensing of Opioids (SSDO) apparatus 100 is utilized to schedule, edit and view medication to be dispensed, provide visual communication between the artificial intelligence Avatar assist 106 and the user and provide video communication between the user and remotely located operators and caregivers.

The artificial intelligence Avatar assistant 106 of the Secure Storage for Dispensing of Opioids (SSDO) apparatus 100 utilizes text to speech, speech to text and Natural Language Processing (NLP) 223 technology to interactively communicate with the user, triage the user and gather relevant information regarding user's health status.

The front supporting leg 107 of the Secure Storage for Dispensing of Opioids (SSDO) apparatus 100 that can be folded closed and snapped in place to allow the device to be carried around.

The rear supporting leg 108 of the Secure Storage for Dispensing of Opioids (SSDO) apparatus 100 that can be folded closed and snapped in place to allow the device to be carried around. The rear leg 108 can also folded fully open and snapped in place, to be used as a carrying handle for the device.

Figure 9:
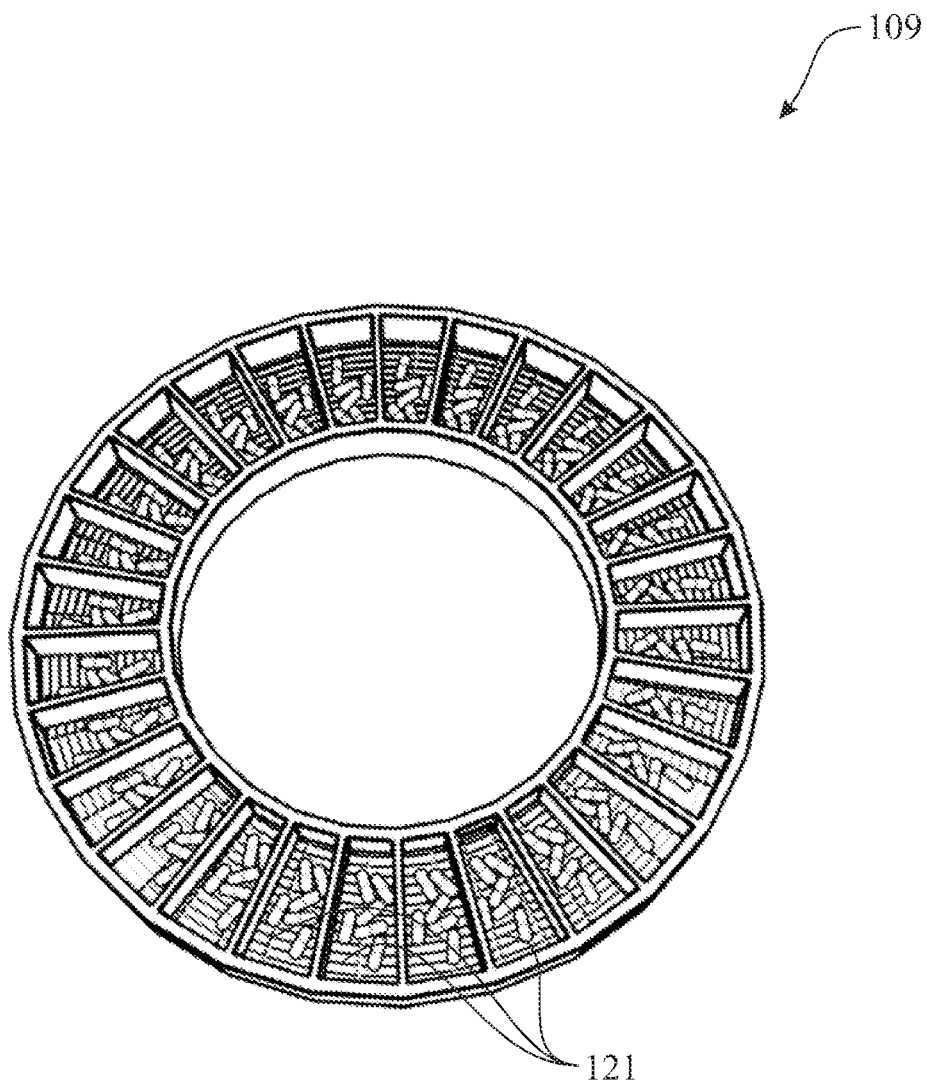
FIG. 9 presents a top isometric view of an exemplary sealed blister pack filled with pills.
Figure 10:
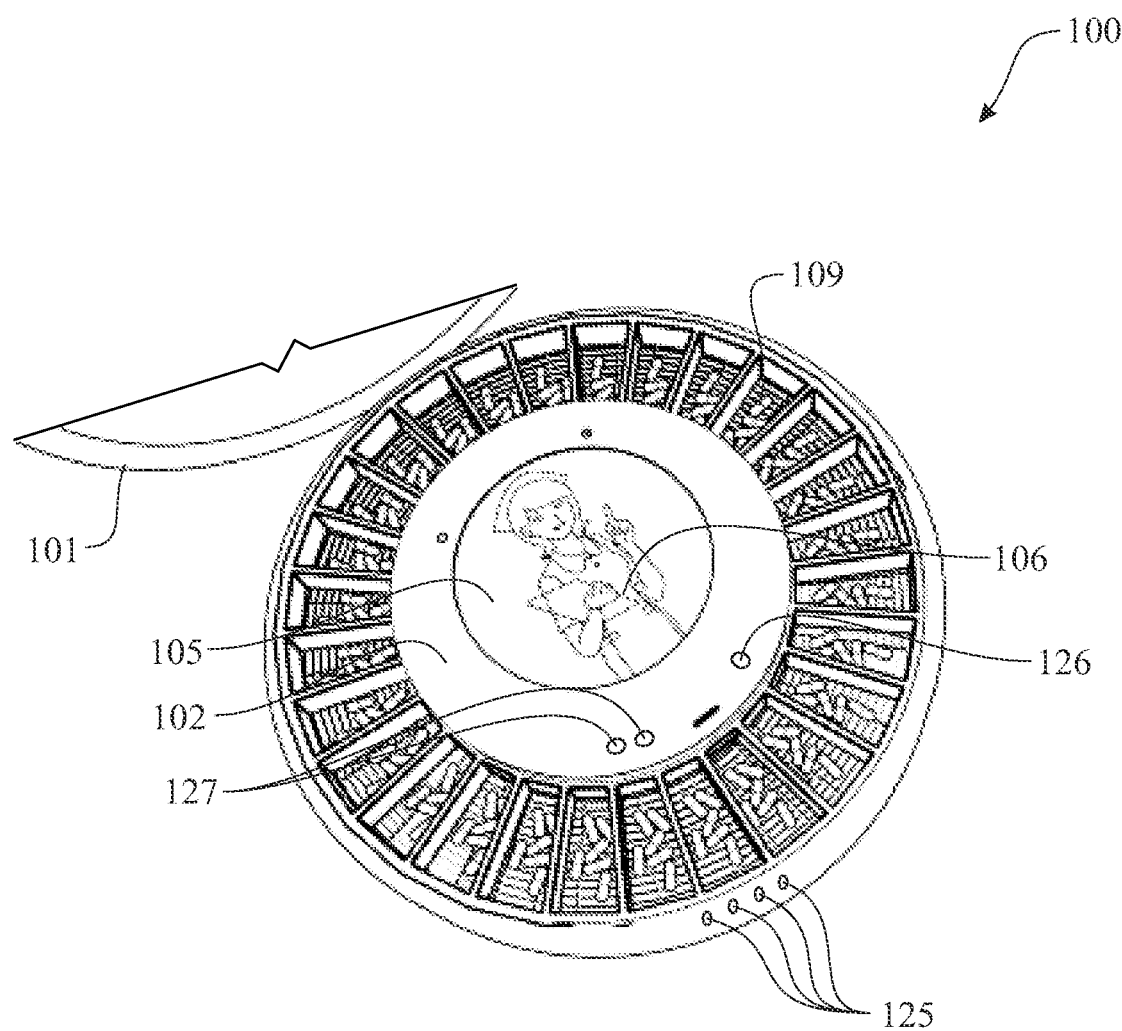
FIG. 10 presents a top, front, right side isometric view of the Opioid dispenser, the illustration presenting the sealed blister pack filled with pills inserted in to the primary tray of the Opioids dispenser.
Figure 11:
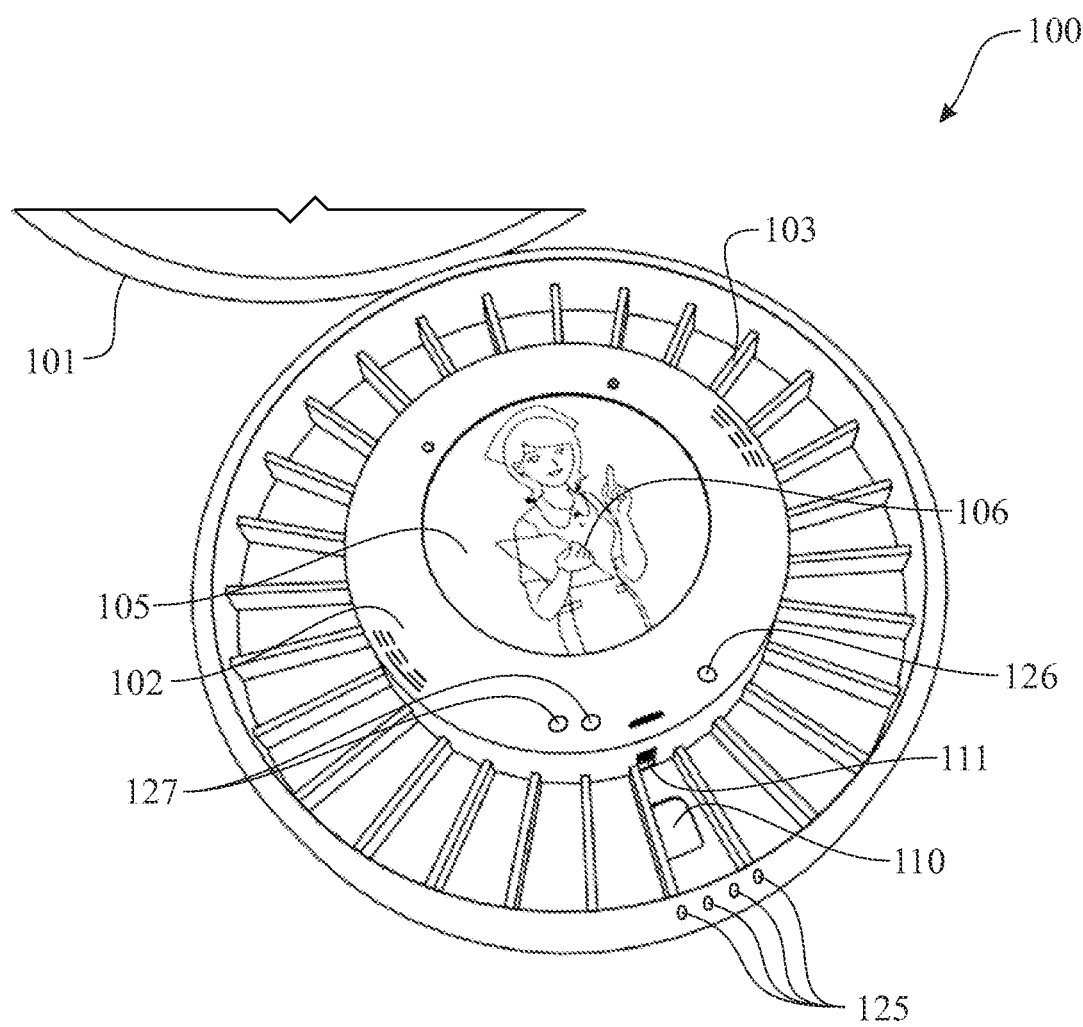
FIG. 11 presents a top, front, left side isometric view of the Opioid dispenser, the illustration introducing a punch lever, the punch lever being in a fully retracted position.
Figure 12:
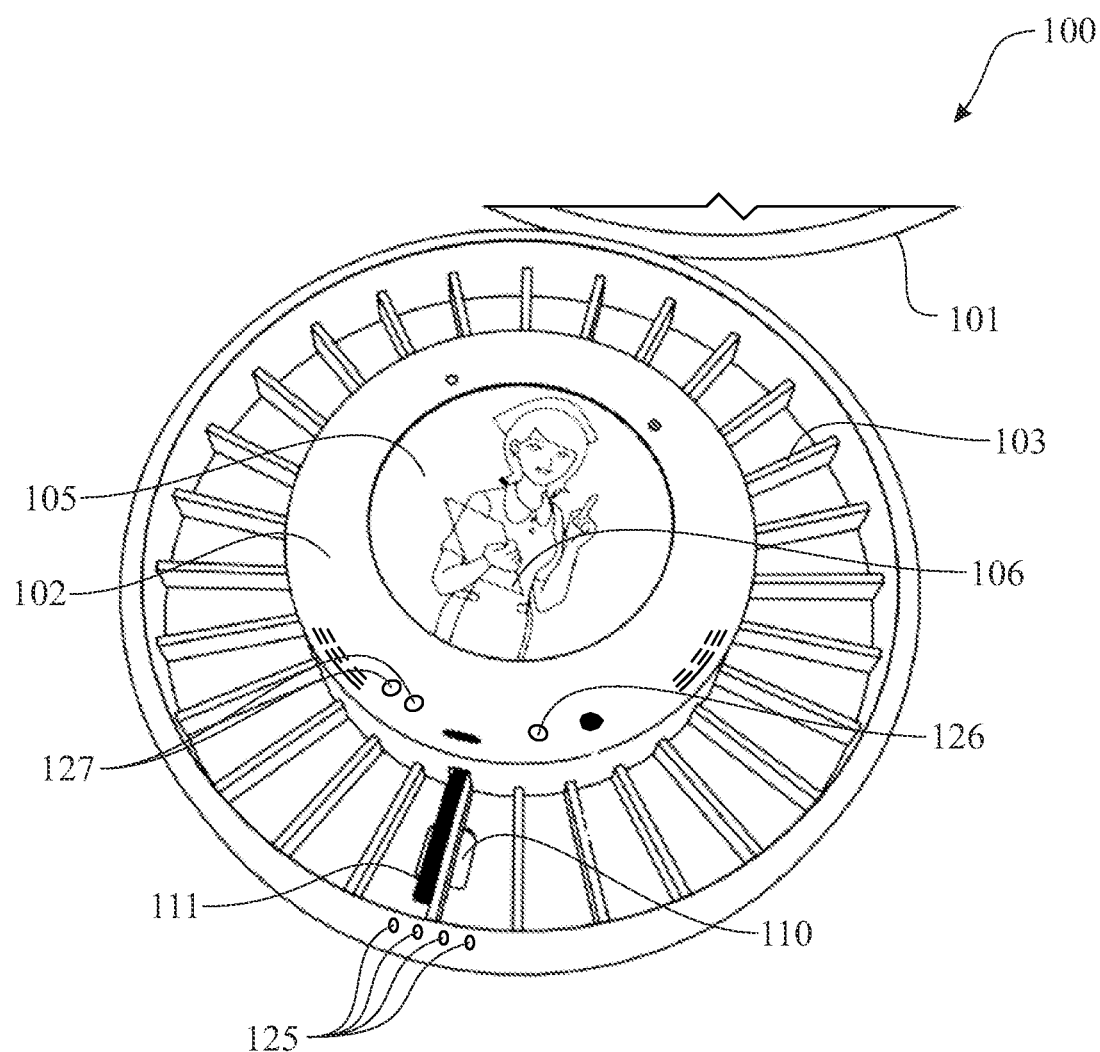
FIG. 12 presents a top, front, left side isometric view of the Opioid dispenser, the illustration presenting the punch lever in a fully extended position, where the extended punch lever would tear thru the blister seal along a straight linear line.
Figure 13:
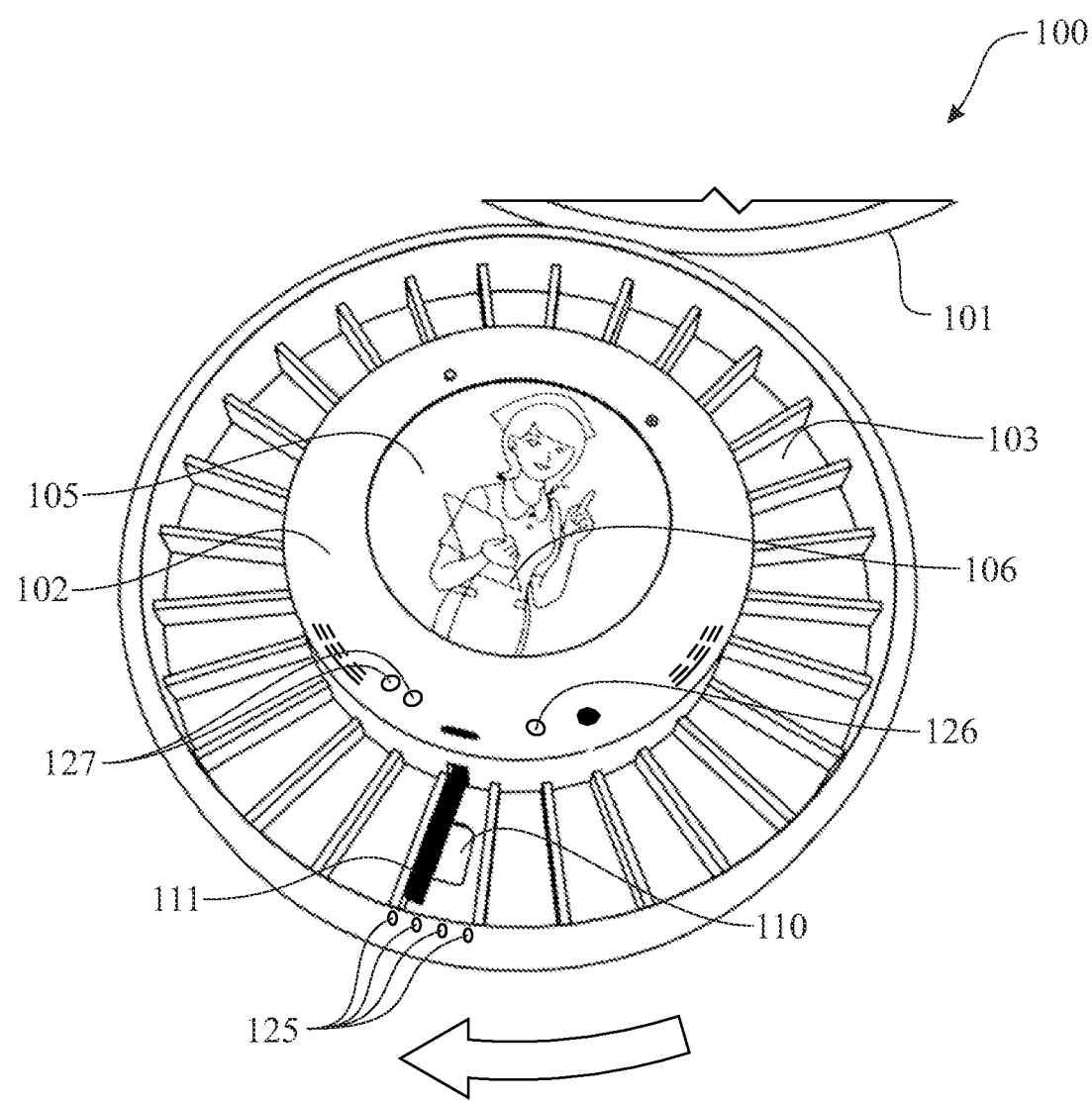
FIG. 13 presents a top, front, left side isometric view of the Opioid dispenser, the illustration presenting the punch lever position in a fully extended position, where the primary tray is rotated one compartment counter-clockwise to tear an entire blister foil area.
Figure 14:
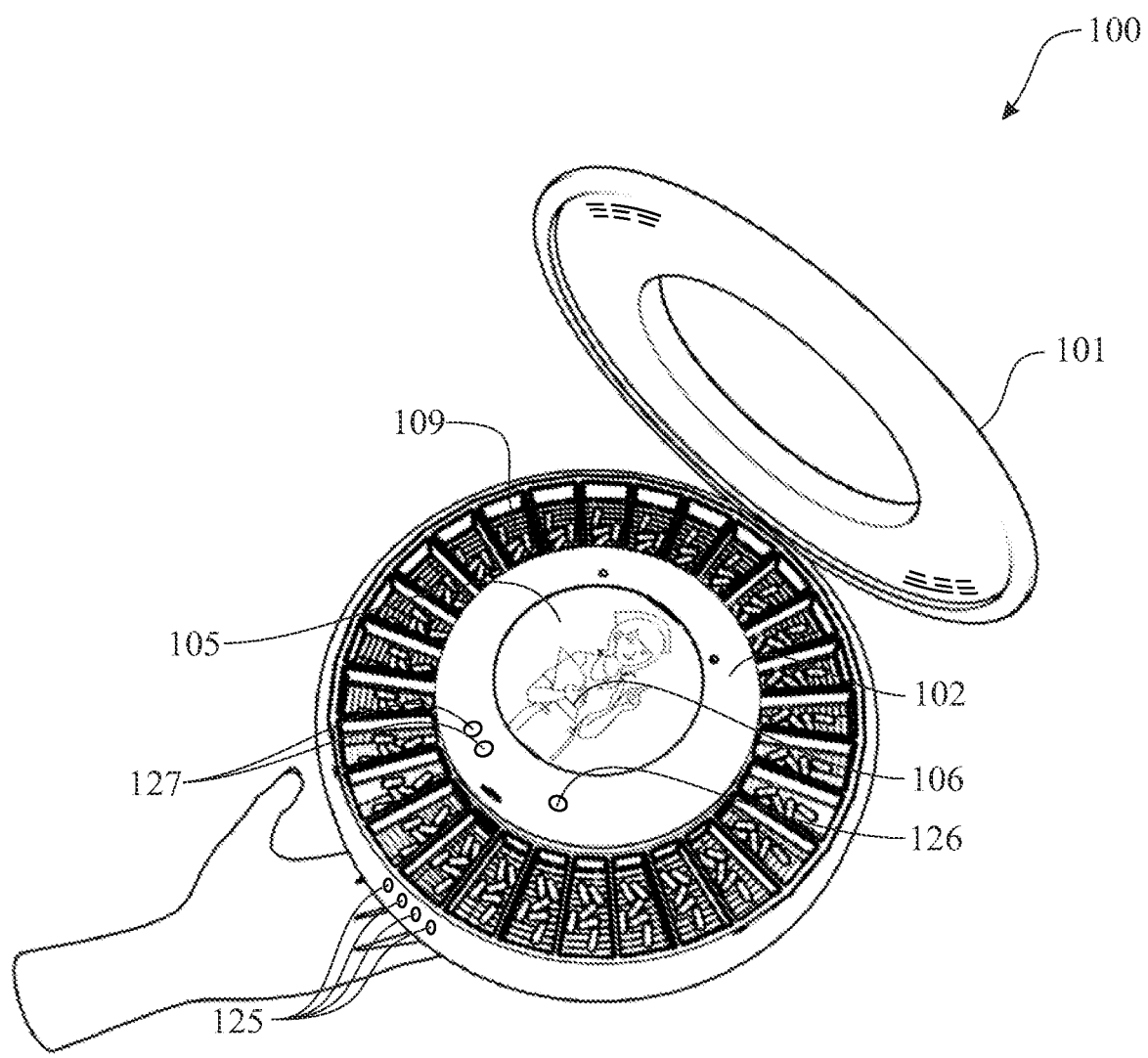
FIG. 14 presents a top, front, right side isometric view of the Opioid dispenser, the illustration presenting a dispensing of pills from the blister pack of pills located within the primary tray.

The sealed blister pack 109, as shown in FIGS. 9 and 10, contains a plurality of medication compartments 121. The sealed blister pack 109 is also filled and pre-sealed with medication and placed into the primary medication tray 103 of the Secure Storage for Dispensing of Opioids (SSDO) apparatus 100. A unique punching mechanism then punctures the sealed blister 109 allowing the pills contained in the blister pack 109 to be released at appropriate time scheduled.

In the dispense compartment, another benefit of the Secure Storage for Dispensing of Opioids (SSDO) apparatus 100, is an ability to simultaneously dispense pills that were (a) manually loaded in the primary medication tray 103, (b) pills contained in the sealed blister pack 109, and supplemental pills manually placed within the secondary medication tray 104, thru a common dispense compartment.

Another feature of the Secure Storage for Dispensing of Opioids (SSDO) apparatus 100 is a motorized punching mechanism 253 detailed in FIGS. 11 through 14. The punch lever 11 utilizes a dual cutting motion to puncture the sealed blister pack 109 and dispense the contained medication into the dispense compartment 110 at scheduled times. In its default normal mode of operation, the punch lever 111 in fully retracted inside the mechanism center core. To tear open the sealed blister pack 109 and release the contained medication, the punch lever 111 is first fully extended out along a straight path creating a straight linear tear in the sealed blister pack 109. Once the punch lever 111 is fully extend out, it will lock in that position while the primary medication compartment 103 then utilizes the primary medication tray motorized system 251 to make a rotary move to cover the entire width of one medication compartment 128 distance. As the result of the secondary rotary movement by the primary medication tray 103, the punch lever 111 will produce a full area tear of the blister pack 109 for the entire surface of one primary medication tray compartment 128.

The charging contacts 112 located within each storage shelf 114 of the storage cart 113 are arranged to create an electrical communication link with the Opioids dispenser charging contacts 125 to enable charging of the Secure Storage for Dispensing of Opioids (SSDO) apparatus 100 while the Secure Storage for Dispensing of Opioids (SSDO) apparatus 100 is docked. The charging contacts 112 within each storage shelf 114 further provide a connection circuitry for the storage cart 113 to access, log and report the ID, Configuration information on each Opioids dispenser, as well as the medication dispensed from the primary medication tray 103, the secondary medication tray 104 and the sealed blister pack 109.

Referring to the storage cart, the unique storage cart 113 is shown comprising one or more storage shelves 114 to place and dock the Secure Storage for Dispensing of Opioids (SSDO) apparatus 100. The storage cart further provides charging contacts for each storage shelf to allow charging the Secure Storage for Dispensing of Opioids (SSDO) apparatus 100 while being docked. While the Secure Storage for Dispensing of Opioids (SSDO) apparatus 100 are docked in the cart shelves 114, the storage cart further employs the charging contacts 112 to access, log and report the ID, configuration information on each Secure Storage for Dispensing of Opioids (SSDO) apparatus 100, as well as the medication dispensed from the primary medication tray 103, the secondary medication tray 104 and the sealed blister pack 109.

The storage/charging cart/station are illustrated in FIGS. 15 through 19. Each storage cart 113 comprises of one or more storage shelves 114 to place and dock the Secure Storage for Dispensing of Opioids (SSDO) apparatus 100. The charging contacts 112 within each storage shelf 114 of the storage cart 113 allow charging of the Secure Storage for Dispensing of Opioids (SSDO) apparatus 100 while being docked. The charging contacts 112 within each storage shelf 114 further provides the connection circuitry for the storage cart 113 to access, log and report the ID, configuration information on each Secure Storage for Dispensing of Opioids (SSDO) apparatus 100, as well as the medication dispensed from the primary medication tray 103, the secondary medication tray 104 and the sealed blister pack 109.

An ankle/wrist Opioid dispensing bracelet 200 is an alternate form of the Secure Storage for Dispensing of Opioids (SSDO) apparatus 100. The ankle/wrist Opioid dispensing bracelet 200 is provided in a form factor of a bracelet in order to provide mobile dispensing and monitoring of the Opioids usage and adherence. The Opioids dispensing bracelet 200 can be configured to be placed on the user's wrist as an Opioids dispensing bracelet 200. Alternatively, the Opioids dispensing bracelet 200 can be configured to be placed on the user's ankle.

Each Opioids dispensing bracelet 200 comprises of one or more medication compartments 116 which will contain the medication to be dispensed at scheduled time. Each medication compartment 116 of the Opioids dispensing bracelet 200 comprises of a compartment door 117, a compartment door motor 118, and motor controller circuitry 254 to securely open and close the respective compartment door 117.

Each medication compartment 116 of Opioids dispensing bracelet 200 comprises a compartment door 117, a motorized mechanism 254, and an actuating door motor 118.

The actuating door motor 118 and the associated supporting motor controller circuitry 254 are provided for each bracelet medication compartment door 117 to securely open and close the respective compartment door 117.

The bracelet band 115 is configured to support a main bracelet control unit 124 and a plurality of the bracelet medication compartments 116.

The bracelet docking magnets provide contact points between the Opioid dispensing bracelet 115 and the Secure Storage for Dispensing of Opioids (SSDO) apparatus 100.

The main bracelet control unit 124 comprises a touch display unit 122 which provides interactive communication between the Opioids dispensing bracelet 115) with the bracelet artificial intelligence Avatar assistant 123. The bracelet touch display 122 can also provide video communication between the user and the remote operators and caregivers.

The main bracelet control unit 124 comprises of a touch display unit 122 which provided interactive communication between the Opioids dispensing bracelet 200 with the bracelet artificial intelligence Avatar assistant 123. The artificial intelligence virtual Avatar assistant 123 of the current invention, Opioids bracelet 200 utilizes text to speech, speech to text and Natural Language Processing (NLP) 223 technology to interactively communicate with the user, triage the user and gather relevant information regarding user's health status.

The main bracelet control unit 124 comprises of a touch display unit 122 which provided interactive communication between the Opioids dispensing bracelet 200 with the bracelet artificial intelligence Avatar assistant 123.

The Opioids dispenser charging contacts 125, which are detailed in FIGS. 32 through 36, connects to the charging contacts 112 within each storage shelf 114 of the storage cart 113 to allow charging the Secure Storage for Dispensing of Opioids (SSDO) apparatus 100 while being docked. The charging contacts 125 further provide the storage cart 113 with access, log and report the ID, configuration information on each Secure Storage for Dispensing of Opioids (SSDO) apparatus 100, as well as the medication dispensed from the primary medication tray 103, the secondary medication tray 104 and the sealed blister pack 109.

The secondary mediation tray cover 102 further comprises of a microphone 126 which allows the artificial intelligence Avatar assistant 123 as well as the remote operators and caregivers to interactively communicate with the user. The secondary mediation tray cover 102 further comprising a speaker 127 which allows the artificial intelligence avatar assistant 123 as well as the remote operators and caregivers to interactively communicate with the user. The primary medication tray 103 comprises of multiple medication compartments 128 containing the Opioids and other medications for one or more time instances during a day such as morning, noon, afternoon and evening, as well as one or more days of the week. The secondary medication tray 104 comprises of multiple medication compartments 129 containing vitamins, supplemental medication and new additions to regular medication contained in the primary medication tray 103.

Figure 37:
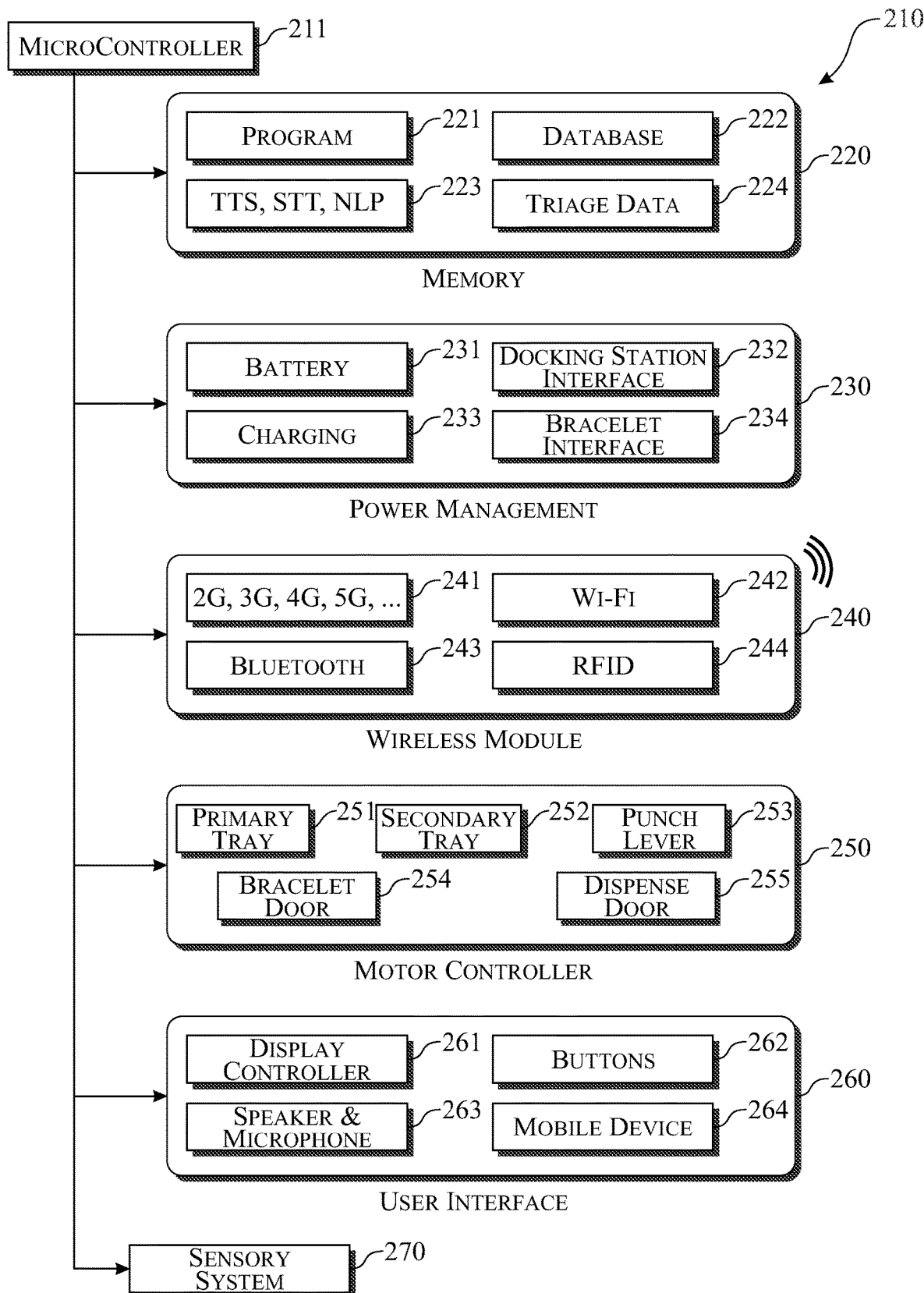
FIG. 37 presents a block diagram of elements of the present invention.

An electronic block diagram representative of the Secure Storage for Dispensing of Opioids (SSDO) 210 is presented in FIG. 37. The block diagram comprises of a microcontroller 211, a memory module 220, a power management system 230, a wireless module 240, a motor controller 250, a user interface 260 and a sensory system 270.

The memory module 220 includes a storage area for the program 221, a database 222, text to speech (TTS), speech to text (STT) and Natural Language Processing (NLP) 223 as well as storage area for triage data 224.

The power management module 230 includes a battery 231, a docking station interface 232, a charging circuitry 233 and a bracelet interface 234.

The wireless module 240 includes cellular transmission circuitry 241 for 2G, 3G, 4G and 5G, Wi-Fi circuitry 242, Bluetooth circuitry 243 and RFID circuitry 244.

The motor controller module 250 includes motor control circuitry for a primary tray 251, a secondary tray 252, a punch lever 253, a bracelet door 254 and a dispense door 255.

The user interface module 260 includes a display controller 261, buttons 262, a speaker and a microphone 263, and a mobile device 264.

The sensory system module 270 contains circuitry for various optical and mechanical sensors.

Figure 38:
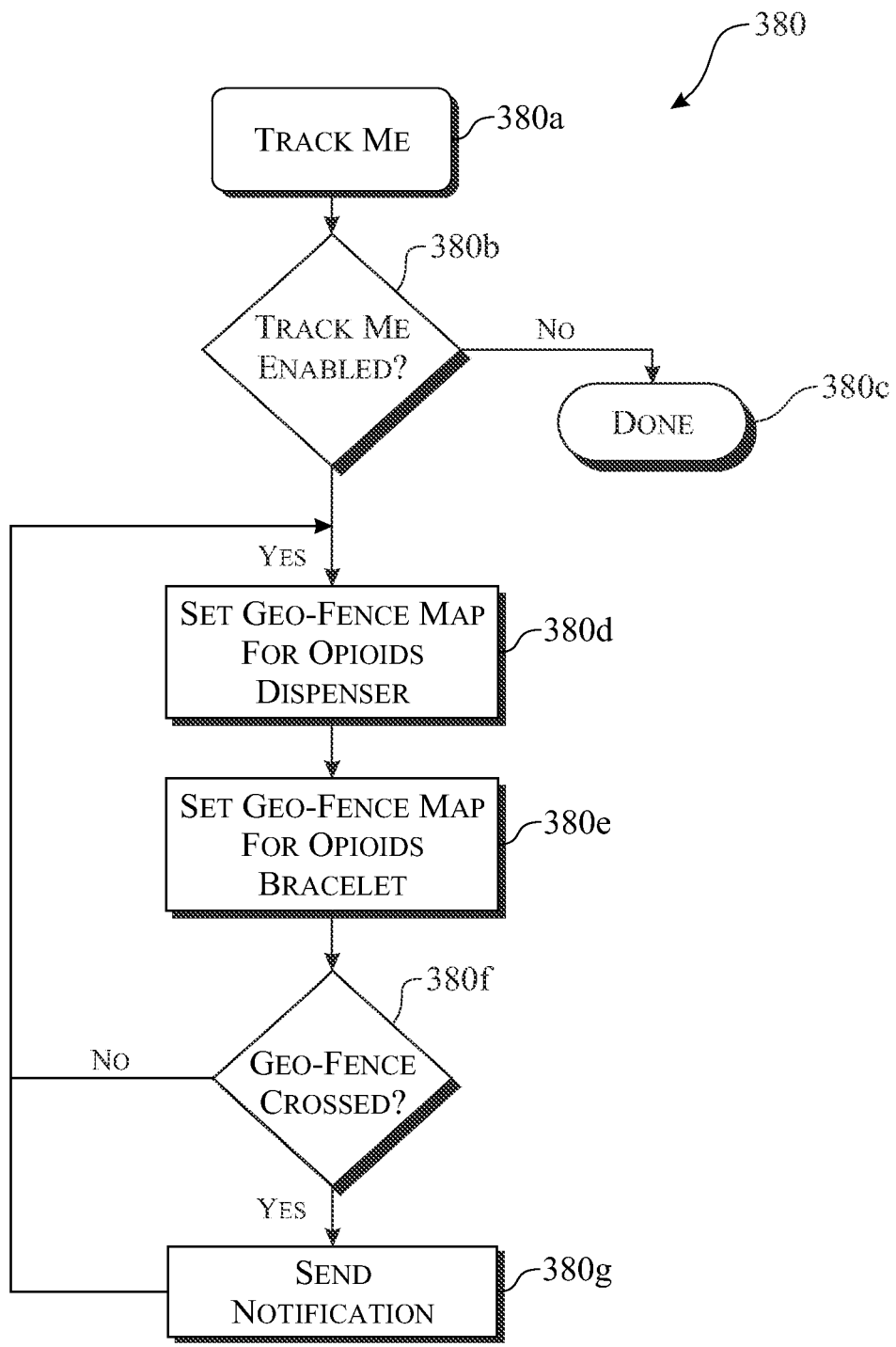
FIG. 38 presents an exemplary flow diagram detailing steps of a "Track Me" process.

A Track Me software flow diagram 380 for use in conjunction with the Secure Storage for Dispensing of Opioids (SSDO) apparatus 100 is presented in FIG. 38. The Track Me process 380 begins with a check as to whether the process is enabled 380b. If the Track Me process is not enabled, then the process is done 280c. If the Track Me process 380 is enabled, then the process continues within a continuous loop. A Geo-fence for the Secure Storage for Dispensing of Opioids (SSDO) apparatus 100 is established 380d, followed by a setting of a Geo-fence for the Opioids bracelet 200 380e. Next the Global Positioning System (GPS) locations are checked to see if the any of the Secure Storage for Dispensing of Opioids (SSDO) apparatus 100 or the Opioids dispensing bracelet 200 cross their respective geo-fences 380f. If geo-fence has not been crossed (decision step 380f), then the process loops back and continues setting the geo-fence area 380d, 380e and checking to see if either device has crossed the designated area 380f. In the event that geo-fence is crossed 380f, notifications are sent to remote operators and caregivers 380g. The process again, loops back and continues setting the geo-fence area 380d, 380e and checking to see if either device has crossed the designated area 380f.

Figure 39:
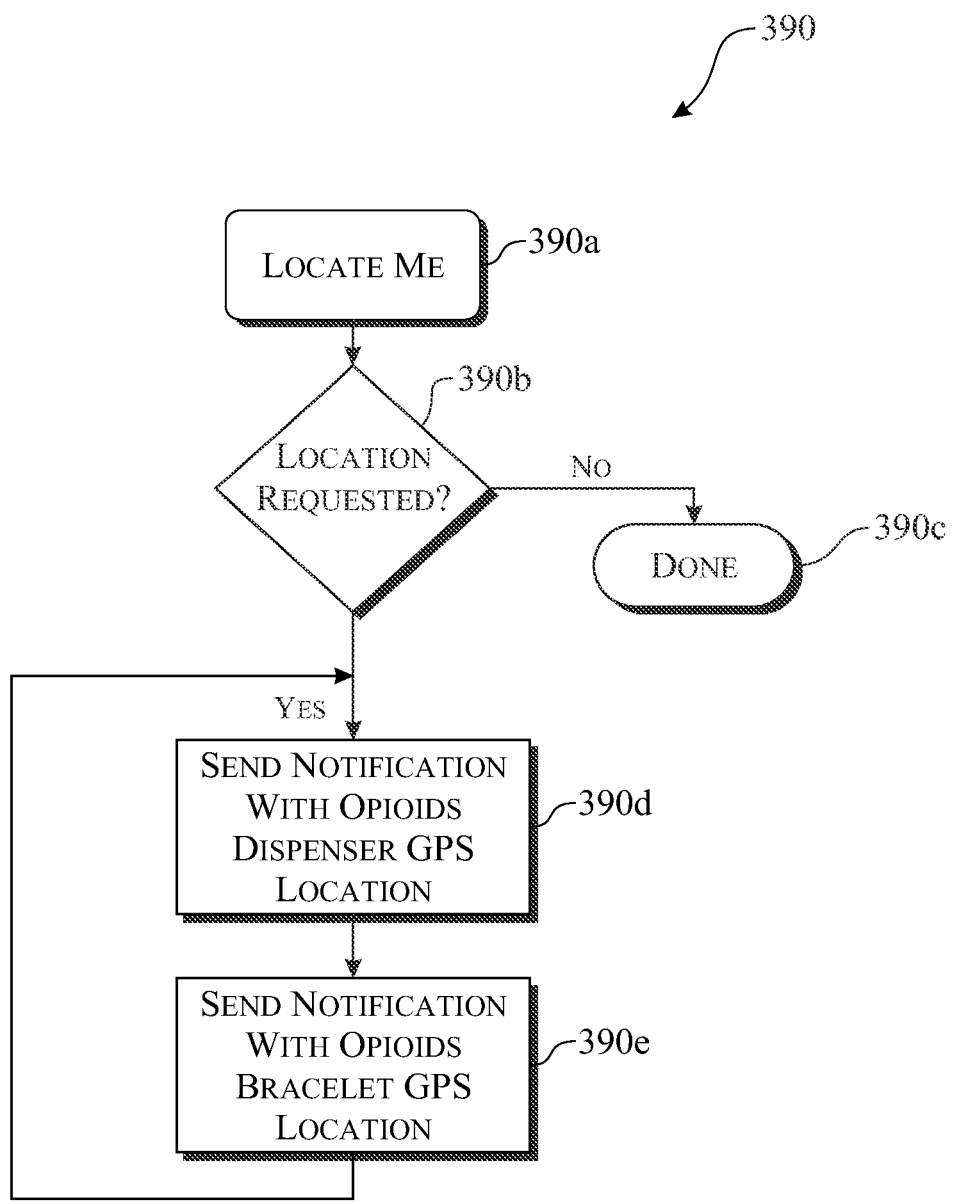
FIG. 39 presents an exemplary flow diagram detailing steps of a "Locate Me" process.

A Locate Me software flow diagram 390 for use in conjunction with the Secure Storage for Dispensing of Opioids (SSDO) apparatus 100 is presented in FIG. 39. The Locate Me software 390 begins with a check as to whether the process is enabled 390b. If the Locate Me software 390 is not enabled, then the process is done 390c. If the process is enabled, the Locate Me software 390 then enters a continuous loop which sends a notification of the Opioids Dispenser GPS location 390d. This is followed by a step of sending a notification of the Opioid Bracelet GPS location 390e.

Figure 40:
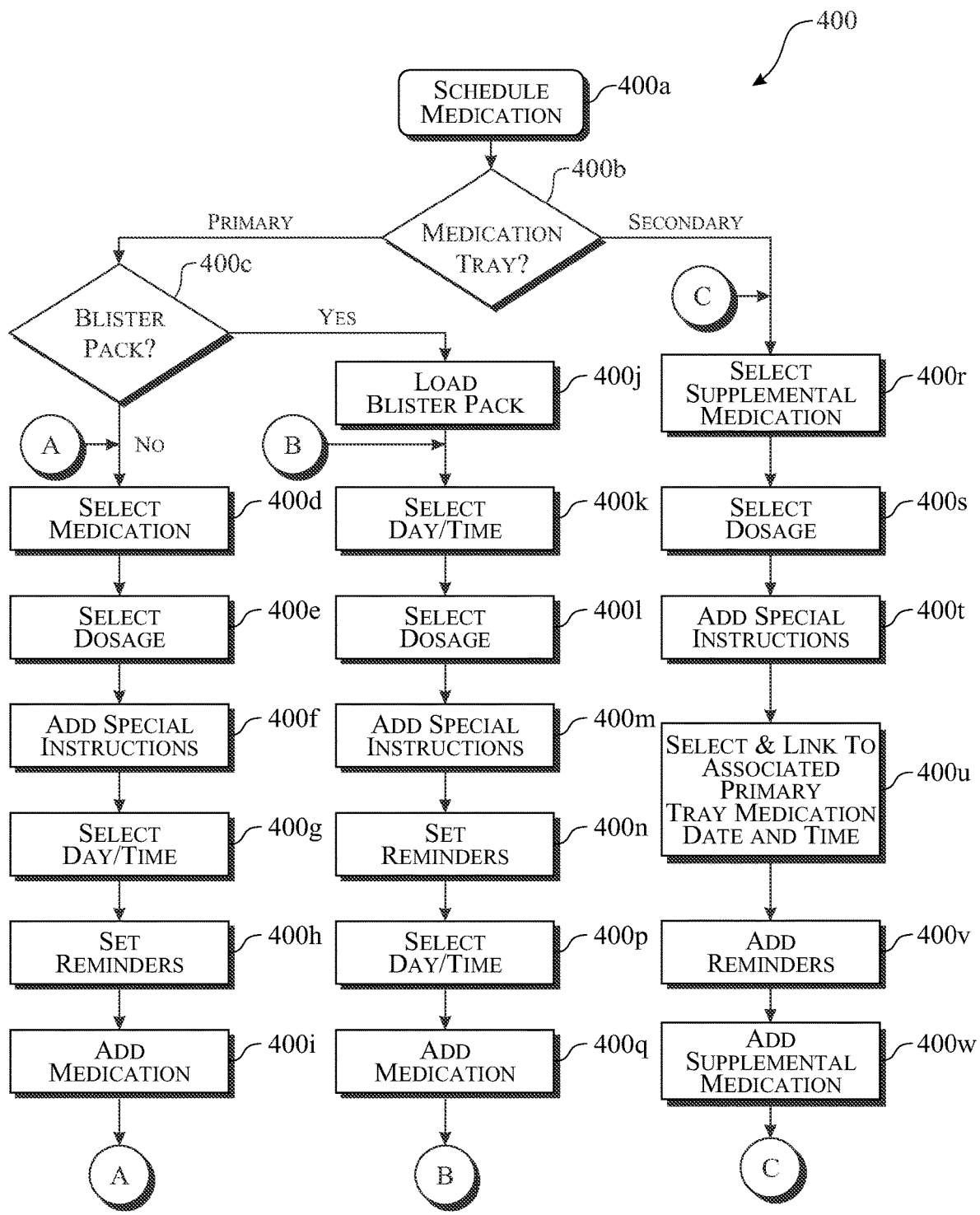
FIG. 40 presents an exemplary flow diagram detailing steps of a process for scheduling dispensing of medication.

A Schedule Medication software flow diagram 400 for use in conjunction with the Secure Storage for Dispensing of Opioids (SSDO) apparatus 100 is presented in FIG. 40. The Schedule Medication process 400 begins with an activation of the Schedule Medication interface 400a in a condition where the Schedule Medication process 400 is enabled. The Schedule Medication process 400 checks for the availability of a medication tray in the primary medication compartment and the secondary medication compartment.

The primary medication scheduling checks for a blister pack 109 (step 400c). If there is no blister pack 109, the primary medication scheduling process prompts a loading of a blister pack 400j. The primary medication scheduling process prompts for the selection of a date and a time for administration of the medication 400k. After selection date and time, the primary medication scheduling process then prompts for a dosage selection 400l. The primary medication scheduling process prompts for an addition of any special instructions 400m. The next prompt pops up, requesting entry to setting reminders as to when to take the medication 400n. The primary medication scheduling process then prompts for the selection of a date and a time 400p. The primary medication scheduling process then prompts for adding medication 400q.

If there is a blister pack 109 contained in the primary medication tray 103, the Schedule Medication process 400 will ask for a selection of the medication 400d. After that, the Schedule Medication process 400 will then prompts for entry of a dosage selection 400e. The Schedule Medication process 400 prompts for the addition of any special instructions 400f. Next, the Schedule Medication process 400 prompts for the selection of a date and a time for administration of the medication 400g. The next prompt is for setting reminders as to when to take the medication 400h. The Schedule Medication process 400 then presents a prompt for adding medication 400i.

The secondary medication scheduling portion involves selecting the supplemental medication 400r. After the supplemental medication has been set, the secondary medication scheduling portion prompts for a dosage selection 400s. After the dosage selection has been completed, the secondary medication scheduling portion prompts for the addition of any special instructions 400t. After entry of any special instructions has been completed, the secondary medication scheduling portion prompts the selection and linking to the associated primary tray medication date and time 400n. After that has been completed, the secondary medication scheduling portion prompts for the addition of reminders 400v. After that is done, the secondary medication scheduling portion prompts for the addition of supplemental medication 400w.

Figure 41:
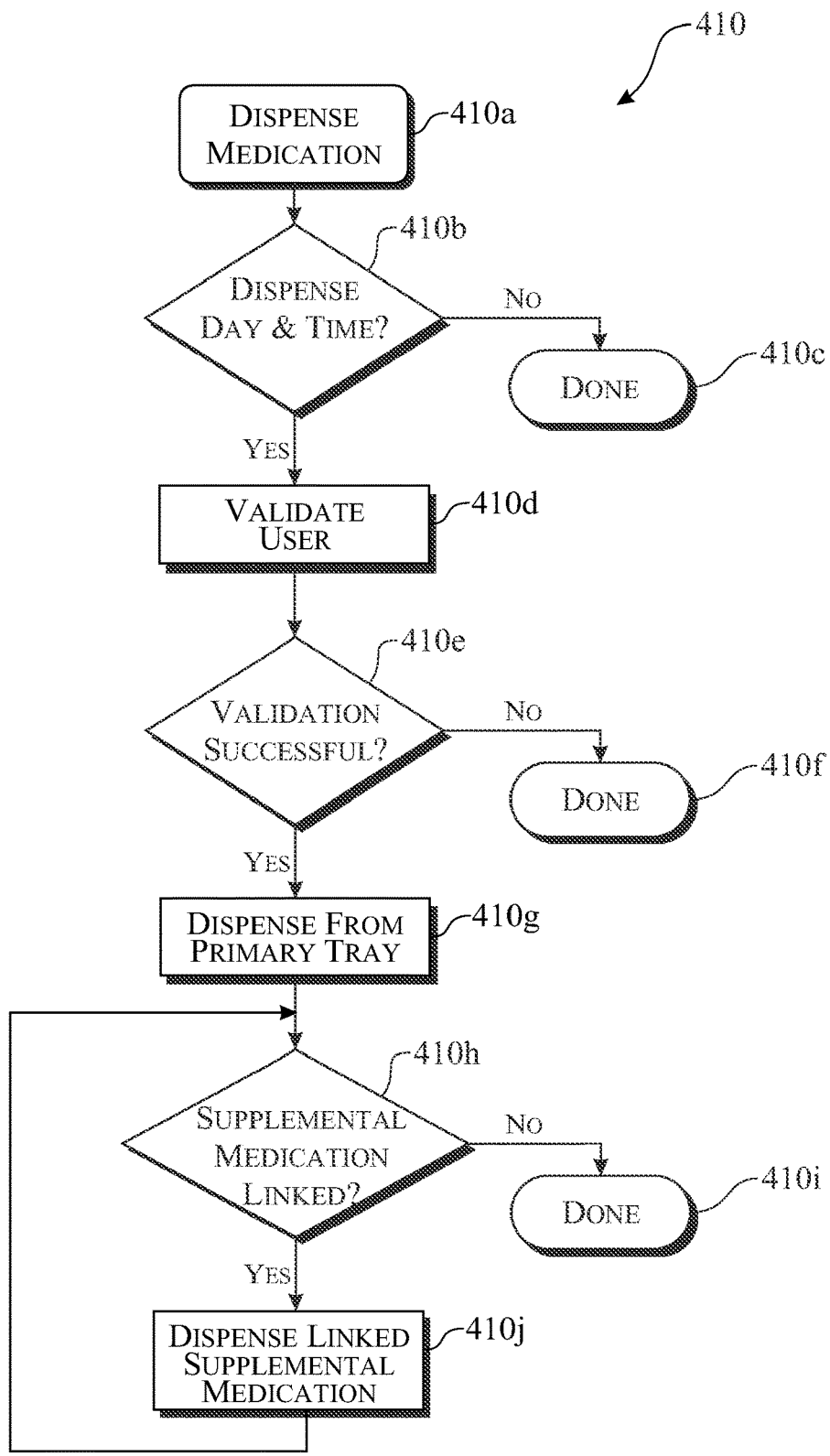
FIG. 41 presents an exemplary flow diagram detailing steps of a process for dispensing medication.

A Dispense Medication software flow diagram 410 for use in conjunction with the Secure Storage for Dispensing of Opioids (SSDO) 100 is presented in FIG. 41. In the dispense medication flow diagram 410, the process involves a step of determining the dispense day and time 410b, validation of the user 410d, dispensing from the primary tray 410g and finally linking supplemental medication 410g. The Dispense Medication process 410 begins with a check to determine whether the process is enabled 410a. If the process is enabled, then the Dispense Medication process 410 checks for the date and time 410b. If it is not time for administration of a medication then the process is done 401c. If Dispense Medication process 410 determines that it is time for the medication the Dispense Medication process 410 goes forward to validate the user taking the medication 410d. If the validation fails, the process us done and nothing happens 410f. If the validation is successful 410e the Dispense Medication process 410 dispenses medication from the primary tray 410g. After dispensing the medication from the primary tray 410g, the Dispense Medication process 410 checks if any Supplemental Medication is linked 410h. If no supplemental medication is linked, the process ends 410i. If any supplemental medication is linked, the Dispense Medication process 410 dispenses the supplemental medication 410j.

Figure 42:
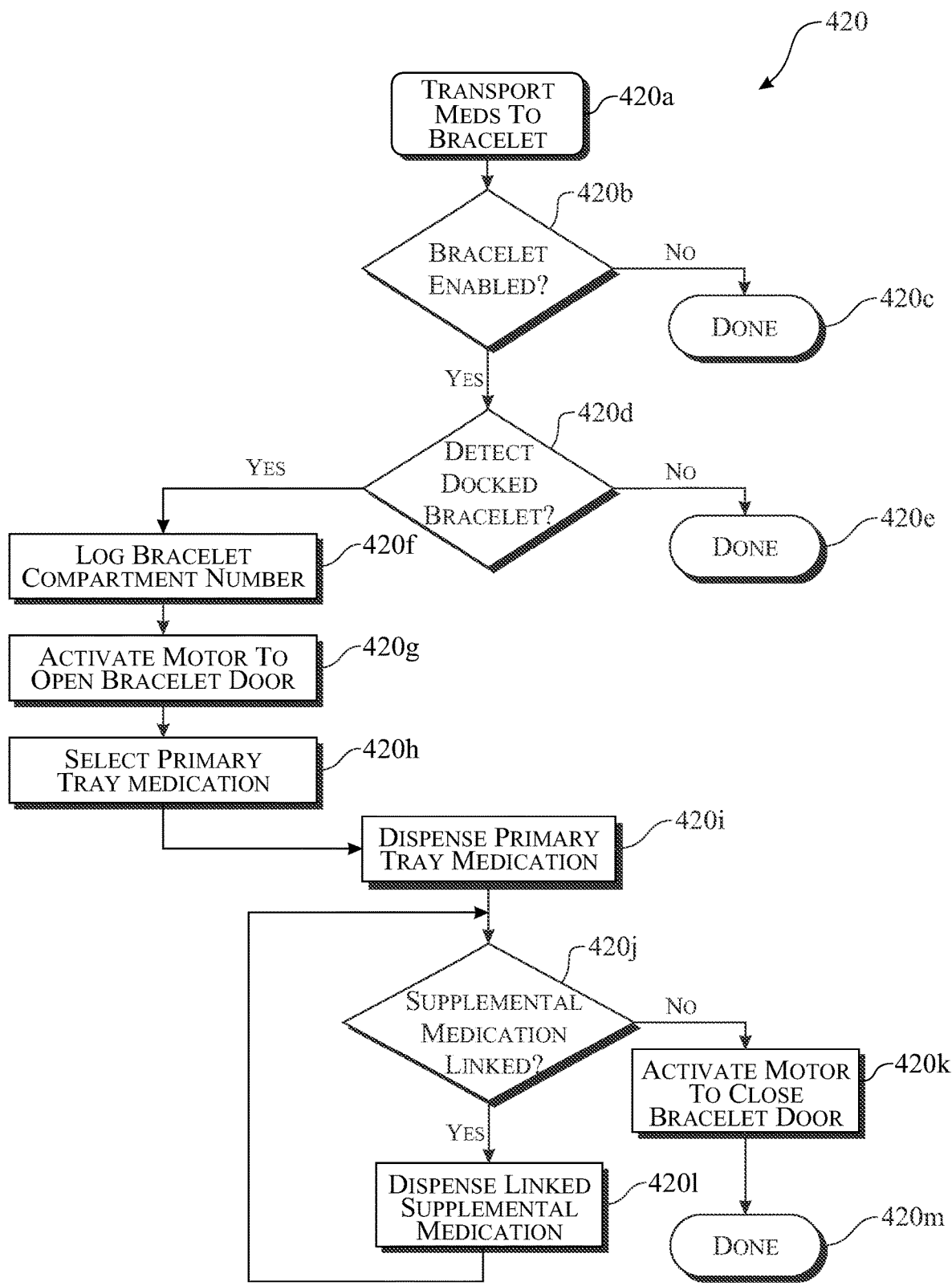
FIG. 42 presents an exemplary flow diagram detailing steps of a process for transferring medication to the bracelet.

Referring to FIG. 42 shows the present invention A Transport Meds to Bracelet software flow diagram 420 for use in conjunction with the Secure Storage for Dispensing of Opioids (SSDO) 100 is presented in FIG. 42. In the process, bracelet enable and detecting docked bracelet are determined prior to dispensing primary tray medication. The Transport Meds to Bracelet process 420 checks for authorization to transport medication if no authorization is indicated, the process is done 420c. If there is authorization, the Transport Meds to Bracelet software moves to detect a docked bracelet 420d. If there is no docked bracelet, then the process is done 420e. If a docked bracelet is detected the Transport Meds to Bracelet software logs the bracelet compartment number 420f. The Transport Meds to Bracelet software activates the motor to open the bracelet door 420g. Then, the primary medication tray 103 is selected 420h. Next, the primary medication tray 103 dispenses the medication into the bracelet 420i. Next, the Transport Meds to Bracelet software checks if supplemental medication is linked 420j. If no supplemental medication is linked, the Transport Meds to Bracelet software activates the motor to close the bracelet door 420k. Then the process is done 420m. If there is linked supplemental medication, the Transport Meds to Bracelet software dispenses the supplemental medication accordingly 420i.

Figure 43:
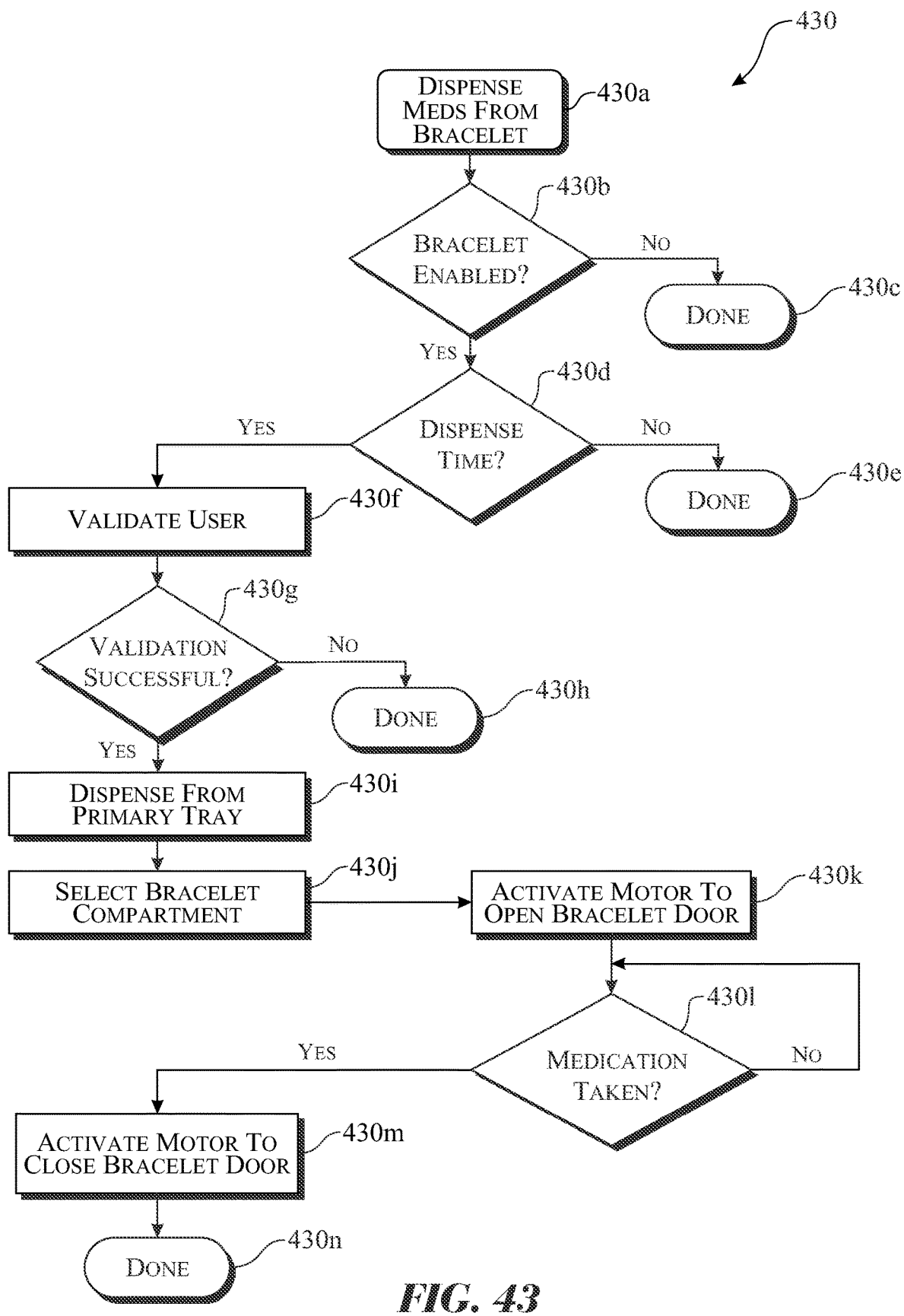
FIG. 43 presents an exemplary flow diagram detailing steps of a process for dispensing medication from the bracelet.

A Dispense Meds from bracelet software flow diagram 430 for use in conjunction with the Secure Storage for Dispensing of Opioids (SSDO) apparatus 100 is presented in FIG. 43. In the dispense meds from bracelet flow diagram 430, a bracelet enabled 430b is determined followed by determining the dispense time 430d. As soon as a user validation process is completed, the motor is activated to open the bracelet door and finally medication is taken prior to closing the bracelet door. The Dispense Meds from bracelet process 430 checks for the availability of medication 430a. The Dispense Meds from bracelet process 430 then checks to verify that the bracelet is enabled 430b. If the bracelet is not enabled, then the process is done 430c. If the bracelet is enabled, the Dispense Meds from bracelet process 430 checks for a dispensing time 430d. If the Dispense Meds from bracelet process 430 determines that it is not time for administration of the medication, then the process is done 430e. If the Dispense Meds from bracelet process 430 determines that it is time for dispensing the medication, the Dispense Meds from bracelet process 430 asks to validate the user 430f. The Dispense Meds from bracelet process 430 then determines whether the user is validated 430g. If the validation is unsuccessful, then the process is done 430h. If the validation is successful, the Dispense Meds from bracelet process 430 proceeds to dispense medication from the primary tray 430i. To accomplish the dispensing process, the Dispense Meds from bracelet process 430 asks to select the bracelet compartment 430j. The Dispense Meds from bracelet process 430 activates the motor to open the respective bracelet door 430k. The Dispense Meds from bracelet process 430 proceeds with a decision step to determine if the medication have been taken 430l. If no, the Dispense Meds from bracelet process 430 loops back to ensure the door to the respective bracelet compartment is open 430k. If the Dispense Meds from bracelet process 430 determines that the medication was taken, the Dispense Meds from bracelet process 430 activates the motor to close the bracelet door 430m. The process ends 430m.

What is claimed is:
1. A secure medication dispensing system comprising:
   a dispenser and a software for operating the dispenser, the dispenser comprising:
   a. a processor;
   b. memory in signal communication with the processor;
   c. software comprising a set of instructions that are executed by the processor, the software being stored in the memory;
   d. a wireless transceiver in signal communication with the processor;
   e. a first rotatable carousel tray, the first rotatable carousel tray comprising a plurality of first tray medication compartments, the first rotatable carousel tray being arranged to rotatably position each first tray medication compartment containing medication;
   f. a second rotatable carousel tray, the second rotatable carousel tray comprising a plurality of second tray medication compartments, the second rotatable carousel tray being arranged to rotatably position each second tray medication compartment containing medication, rotational positioning of the second rotatable carousel tray being controlled by the software;
   g. at least one closure, wherein the at least one closure provides access to and a secure seal to each of the first rotatable carousel tray and the second rotatable carousel tray;
   h. a user identification system in signal communication with the processor,
   i. a first tray operating control mechanism, wherein the first tray operating control mechanism rotational positions the first rotatable carousel tray, the first tray operating control mechanism being controlled by the software;

j. a second tray operating control mechanism, wherein the second tray operating control mechanism rotational positions the second rotatable carousel tray, the second tray operating control mechanism being controlled by the software;

k. at least one medication dispensing mechanism, the at least one medication dispensing mechanism being arranged to dispense medication from at least one of the first rotatable carousel tray and the second rotatable carousel tray, the medication being dispensed to a medication dispensing compartment;

l. a sensor in signal communication with the processor, the sensor being arranged to detect when medication has been dispensed; and m. a housing carrying the processor, the memory, the sensor mechanism, the first rotatable carousel tray, the second rotatable carousel tray, and the at least one medication dispensing mechanism, the software comprising steps of:
utilizing a dispensing schedule to identify when medication is to be dispensed; and
monitoring the dispensing schedule, and
notifying at least one of a local operator, a remote operator, and a caregiver in a condition where medication is not dispensed from the secure dispenser within the scheduled dispense time period.

2. The secure medication dispensing system as recited in claim 1, the software further comprising a step of dispensing medication from at least one second tray medication compartment of the plurality of second tray medication compartments independent of whether the first carousel tray dispenses medication.

3. The secure medication dispensing system as recited in claim 1, further comprising a tamper proof dual lock mechanism which secures the first rotary cover and the second rotary cover in a closed position.

4. The secure medication dispensing system as recited in claim 1, further comprising at least one of:
(a) an optical non-contact sensor and programming for detection of one of a user's hand or a container into which the dispenser releases medication, and
(b) a biometric sensing mechanism-to authenticate an authorized user prior to execution of a step of dispensing pills.

5. The secure medication dispensing system as recited in claim 1, further comprising a Global Positioning System (GPS) tracking device that reports a location of the secure dispenser to a remote operator.

6. The secure medication dispensing system as recited in claim 1, further comprising at least one blister pack, the at least one blister pack being located in at least one of the first rotatable carousel tray and the second rotatable carousel tray.

7. The secure medication dispensing system as recited in claim 6, further comprising a punch lever arranged to excise medication from the at least one blister pack via a combination of a radial motion of the punch lever in combination with a rotational motion of the respective one of the first rotatable carousel tray and the second rotatable carousel tray.

8. A secure narcotics dispensing system comprising:
a secure narcotics dispenser and a software for operating the dispenser, the dispenser comprising:
a. a processor;
b. memory in signal communication with the processor;
c. software comprising a set of instructions that are executed by the processor, the software being stored in the memory;
d. a wireless transceiver in signal communication with the processor;
e. a first rotatable carousel tray, the first rotatable carousel tray comprising a plurality of first tray medication compartments, the first rotatable carousel tray being arranged to rotatably position each first tray medication compartment containing narcotics;
f. a second rotatable carousel tray, the second rotatable carousel tray comprising a plurality of second tray medication compartments, the second rotatable carousel tray being arranged to rotatably position each second tray medication compartment containing medication, rotational positioning of the second rotatable carousel tray being controlled by the software;
g. at least one closure, wherein the at least one closure provides access to and a secure seal to each of the first rotatable carousel tray and the second rotatable carousel tray;
h. a user identification system in signal communication with the processor,
i. a first tray operating control mechanism, wherein the first tray operating control mechanism rotational positions the first rotatable carousel tray, the first tray operating control mechanism being controlled by the software;
j. a second tray operating control mechanism, wherein the second tray operating control mechanism rotational positions the second rotatable carousel tray, the second tray operating control mechanism being controlled by the software;
k. at least one medication dispensing mechanism, the at least one medication dispensing mechanism being arranged to dispense medication from at least one of the first rotatable carousel tray and the second rotatable carousel tray, the medication being dispensed to a medication dispensing compartment;
l. a sensor in signal communication with the processor, the sensor being arranged to detect when medication has been dispensed; and
m. a housing carrying the processor, the memory, the sensor mechanism, the first rotatable carousel tray, the second rotatable carousel tray, and the at least one medication dispensing mechanism, the software comprising steps of:
verifying that the recipient of the narcotic meets predetermined criteria for administration of the narcotic;
utilizing a dispensing schedule to identify when medication is to be dispensed; and
monitoring the dispensing schedule, and
notifying at least one of a local operator, a remote operator, and a caregiver in a condition where medication is not dispensed from the secure dispenser within the scheduled dispense time period.

9. The secure narcotics dispensing system as recited in claim 8, the software further comprising a step of dispensing medication from at least one second tray medication compartment of the plurality of second tray medication compartments, independent of whether the first carousel tray dispenses medication.

10. The secure narcotics dispensing system as recited in claim 8, further comprising a tamper proof dual lock mechanism which secures the first rotary cover and the second rotary cover in a closed position.

11. The secure narcotics dispensing system as recited in claim 8, further comprising at least one of:
(a) an optical, non-contact sensor and programming for detection of one of a user's hand or a container into which the dispenser releases medication, and (b) a biometric sensing mechanism-to authenticate an authorized user prior to execution of a step of dispensing pills.

12. The secure narcotics dispensing system as recited in claim 8, further comprising a Global Positioning System (GPS) tracking device that reports a location of the secure narcotics dispenser to a remote operator.

13. The secure narcotics dispensing system as recited in claim 8, further comprising at least one blister pack, the at least one blister pack being located in at least one of the first rotatable carousel tray and the second rotatable carousel tray.

14. The secure narcotics dispensing system as recited in claim 13, further comprising a punch lever arranged to excise medication from the at least one blister pack via a combination of a radial motion of the punch lever in combination with a rotational motion of the respective one of the first rotatable carousel tray and the second rotatable carousel tray.

15. A secure medication dispensing system comprising:
  a dispenser and a software for operating the dispenser, the dispenser comprising:
a. a processor;
b. memory in signal communication with the processor;
c. software comprising a set of instructions that are executed by the processor, the software being stored in the memory;
d. a wireless transceiver in signal communication with the processor;
e. a first rotatable carousel tray, the first rotatable carousel tray comprising a plurality of first tray medication compartments, the first rotatable carousel tray being arranged to rotatably position each first tray medication compartment containing medication;
f. a second rotatable carousel tray, the second rotatable carousel tray comprising a plurality of second tray medication compartments, the second rotatable carousel tray being arranged to rotatably position each second tray medication compartment containing medication, rotational positioning of the second rotatable carousel tray being controlled by the software;
g. at least one closure, wherein the at least one closure provides access to and a secure seal to each of the first rotatable carousel tray and the second rotatable carousel tray;
h. a display in signal communication with the processor;
i. a microphone in signal communication with the processor;
j. a speaker in signal communication with the processor;
k. a user identification system in signal communication with the processor,
l. a first tray operating control mechanism, wherein the first tray operating control mechanism rotational positions the first rotatable carousel tray, the first tray operating control mechanism being controlled by the software;
m. a second tray operating control mechanism, wherein the second tray operating control mechanism rotational positions the second rotatable carousel tray, the second tray operating control mechanism being controlled by the software;
n. at least one medication dispensing mechanism, the at least one medication dispensing mechanism being arranged to dispense medication from at least one of the first rotatable carousel tray and the second rotatable carousel tray, the medication being dispensed to a medication dispensing compartment;
o. a sensor in signal communication with the processor, the sensor being arranged to detect when medication has been dispensed; and
p. a housing carrying the processor, the memory, the sensor mechanism, the first rotatable carousel tray, the second rotatable carousel tray, the at least one medication dispensing mechanism, the display, the microphone, and the speaker,
  the software comprising steps of:
    interacting with a user via an interactive artificial intelligence virtual assistant, wherein the interactive artificial intelligence virtual assistant communicates with the user via the display, the speaker, and the microphone;
    utilizing a dispensing schedule to identify when medication is to be dispensed; and
    monitoring the dispensing schedule, and
    notifying at least one of a local operator, a remote operator, and a caregiver in a condition where medication is not dispensed from the secure dispenser within the scheduled dispense time period.

16. The secure medication dispensing system as recited in claim 15, the software further comprising a step of dispensing medication from at least one second tray medication compartment of the plurality of second tray medication compartments, independent of whether the first carousel tray dispenses medication.

17. The secure medication dispensing system as recited in claim 15, further comprising a tamper proof dual lock mechanism which secures the first rotary cover and the second rotary cover in a closed position.

18. The secure medication dispensing system as recited in claim 8, further comprising at least one of:
  (b) an optical, non-contact sensor and programming for detection of one of a user's hand or a container into which the dispenser releases medication, and
  (b) a biometric sensing mechanism-to authenticate an authorized user prior to execution of a step of dispensing pills.

19. The secure medication dispensing system as recited in claim 15, further comprising a Global Positioning System (GPS) tracking device that reports a location of the secure narcotics dispenser to a remote operator.

20. The secure medication dispensing system as recited in claim 15, further comprising at least one blister pack, the at least one blister pack being located in at least one of the first rotatable carousel tray and the second rotatable carousel tray.

21. The secure medication dispensing system as recited in claim 20, further comprising a punch lever arranged to excise medication from the at least one blister pack via a combination of a radial motion of the punch lever in combination with a rotational motion of the respective one of the first rotatable carousel tray and the second rotatable carousel tray.

22. A secure medication dispensing system comprising:
  a dispenser and a software for operating the dispenser, the dispenser comprising:
a. a processor;
b. memory in signal communication with the processor;
c. software comprising a set of instructions that are executed by the processor, the software being stored in the memory;
d. a wireless transceiver in signal communication with the processor;
e. a first rotatable carousel tray, the first rotatable carousel tray comprising a plurality of first tray medication compartments, the first rotatable carousel tray being arranged to rotatably position each first tray medication compartment containing medication;
f. a second rotatable carousel tray, the second rotatable carousel tray comprising a plurality of second tray medication compartments, the second rotatable carousel tray being arranged to rotatably position each second tray medication compartment containing medication, rotational positioning of the second rotatable carousel tray being controlled by the software;

g. at least one closure, wherein the at least one closure provides access to and a secure seal to each of the first rotatable carousel tray and the second rotatable carousel tray;

h. a display in signal communication with the processor;

i. a microphone in signal communication with the processor;

j. a speaker in signal communication with the processor;

k. a user identification system in signal communication with the processor, l. a first tray operating control mechanism, wherein the first tray operating control mechanism rotational positions the first rotatable carousel tray, the first tray operating control mechanism being controlled by the software;

m. a second tray operating control mechanism, wherein the second tray operating control mechanism rotational positions the second rotatable carousel tray, the second tray operating control mechanism being controlled by the software;

n. at least one medication dispensing mechanism, the at least one medication dispensing mechanism being arranged to dispense medication from at least one of the first rotatable carousel tray and the second rotatable carousel tray, the medication being dispensed to a medication dispensing compartment;

o. a sensor in signal communication with the processor, the sensor being arranged to detect when medication has been dispensed; and p. a housing carrying the processor, the memory, the sensor mechanism, the first rotatable carousel tray, the second rotatable carousel tray, the at least one medication dispensing mechanism, the display, the microphone, and the speaker, the software comprising steps of:

interacting with a user via an interactive artificial intelligence virtual assistant, wherein the interactive artificial intelligence virtual assistant communicates with the user via the display, the speaker, and the microphone;

verifying that the recipient of the narcotic meets predetermined criteria for administration of the narcotic;

utilizing a dispensing schedule to identify when medication is to be dispensed; and monitoring the dispensing schedule, and notifying at least one of a local operator, a remote operator, and a caregiver in a condition where medication is not dispensed from the secure narcotics dispenser within the scheduled dispense time period.

23. The secure medication dispensing system as recited in claim 22, the software further comprising a step of dispensing medication from at least one second tray medication compartment of the plurality of second tray medication compartments, independent of whether the first carousel tray dispenses medication.

24. The secure medication dispensing system as recited in claim 22, further comprising at least one of:

(c) an optical, non-contact sensor and programming for detection of one of a user's hand or a container into which the dispenser releases medication, and (b) a biometric sensing mechanism-to authenticate an authorized user prior to execution of a step of dispensing pills.

25. The secure medication dispensing system as recited in claim 22, further comprising a biometric sensing mechanism-to identify an authorized user prior to execution of a step of dispensing pills.

26. The secure medication dispensing system as recited in claim 22, further comprising a Global Positioning System (GPS) tracking device that reports a location of the secure narcotics dispenser to a remote operator.

27. The secure medication dispensing system as recited in claim 22, further comprising at least one blister pack, the at least one blister pack being located in at least one of the first rotatable carousel tray and the second rotatable carousel tray.

28. The secure medication dispensing system as recited in claim 27, further comprising a punch lever arranged to excise medication from the at least one blister pack via a combination of a radial motion of the punch lever in combination with a rotational motion of the respective one of the first rotatable carousel tray and the second rotatable carousel tray.

* * * * *